(12) United States Patent
Gertner et al.

(10) Patent No.: US 11,141,347 B2
(45) Date of Patent: Oct. 12, 2021

(54) THERAPEUTIC ULTRASOUND FOR EYE DISORDERS

(71) Applicant: Olympic Ophthalmics, Inc., Issaquah, WA (US)

(72) Inventors: Michael Eric Gertner, Menlo Park, CA (US); Jimin Zhang, Bellevue, WA (US)

(73) Assignee: Olympic Ophthalmics, Inc., Issaquah, WA (US)

( * ) Notice: Subject to any disclaimer, the term of this patent is extended or adjusted under 35 U.S.C. 154(b) by 0 days.

(21) Appl. No.: 16/802,346

(22) Filed: Feb. 26, 2020

(65) Prior Publication Data

US 2020/0222729 A1 Jul. 16, 2020

Related U.S. Application Data

(63) Continuation of application No. 16/250,571, filed on Jan. 17, 2019, now Pat. No. 10,952,923, which is a
(Continued)

(51) Int. Cl.
*A61H 23/02* (2006.01)
*A61N 7/00* (2006.01)
(Continued)

(52) U.S. Cl.
CPC ........... *A61H 23/0245* (2013.01); *A61N 7/00* (2013.01); *A61N 7/02* (2013.01);
(Continued)

(58) Field of Classification Search
CPC .... A61H 23/00; A61H 23/02; A61H 23/0218; A61H 23/0245; A61H 2205/02;
(Continued)

(56) References Cited

U.S. PATENT DOCUMENTS 7,976,573 B2   7/2011   Korb et al.
9,440,065 B2   9/2016   Ackermann et al.
(Continued)

FOREIGN PATENT DOCUMENTS

JP      2015077204 A     4/2015
WO   WO-2006129305 A2   12/2006
(Continued)

OTHER PUBLICATIONS

Dartt, DA., Neural regulation of lacrimal gland secretory processes: relevance in dry eye diseases. Prog Retin Eye Res. May 2009;28(3):155-77. doi: 10.1016/j.preteyeres.2009.04.003. Epub Apr. 17, 2009.
(Continued)

*Primary Examiner* — Colin W Stuart
*Assistant Examiner* — Douglas Y Sul
(74) *Attorney, Agent, or Firm* — Wilson Sonsini Goodrich & Rosati

(57) ABSTRACT

Methods and devices are described which allow sound waves to be safely be applied to the eyelid of an eye of a patient or through the eyelid to other structures in the eye or to or through structures in the facial region to effect changes to one or more structures in and around the eye or directly through the cornea or sclera to regions of the eye to treat one or more diseases of the eye.

13 Claims, 48 Drawing Sheets

Related U.S. Application Data continuation of application No. 15/783,872, filed on Oct. 13, 2017.

(60) Provisional application No. 62/521,362, filed on Jun. 16, 2017, provisional application No. 62/509,238, filed on May 24, 2017, provisional application No. 62/451,583, filed on Jan. 27, 2017, provisional application No. 62/422,627, filed on Nov. 16, 2016, provisional application No. 62/410,115, filed on Oct. 19, 2016, provisional application No. 62/408,651, filed on Oct. 14, 2016.

(51) Int. Cl.
*A61N 7/02* (2006.01)
*A61K 9/00* (2006.01)
*A61N 1/36* (2006.01)

(52) U.S. Cl.
CPC ............ *A61H 2201/0153* (2013.01); *A61H 2201/0157* (2013.01); *A61H 2201/0207* (2013.01); *A61H 2201/105* (2013.01); *A61H 2201/1207* (2013.01); *A61H 2201/1607* (2013.01); *A61H 2205/024* (2013.01); *A61H 2230/505* (2013.01); *A61K 9/0048* (2013.01); *A61N 1/36046* (2013.01); *A61N 2007/0026* (2013.01); *A61N 2007/0078* (2013.01)

(58) Field of Classification Search
CPC ........ A61H 2205/022; A61H 2205/023; A61H 2205/024; A61H 2205/025; A61H 2205/026; A61H 2201/1607; A61H 2201/0153; A61H 2201/1207; A61H 2201/1669; A61H 2201/169; A61H 2201/1692; A61H 2201/1695; A61N 2007/026

See application file for complete search history.

(56) References Cited

U.S. PATENT DOCUMENTS

| | | | | |
|---|---|---|---|---|
| 9,539,170 B1* | 1/2017 | Adaie | ............... | A61H 23/006 |
| 9,687,652 B2 | 6/2017 | Franke et al. | | |
| 9,737,712 B2 | 8/2017 | Franke et al. | | |
| 2003/0176898 A1 | 9/2003 | Gross et al. | | |
| 2004/0220644 A1* | 11/2004 | Shalev | ............... | A61N 1/0546 |
| | | | | 607/45 |
| 2007/0060988 A1* | 3/2007 | Grenon | ............... | A61F 9/00 |
| | | | | 607/96 |
| 2008/0249439 A1* | 10/2008 | Tracey | ............... | A61H 39/04 |
| | | | | 601/46 |
| 2008/0269648 A1 | 10/2008 | Bock | | |
| 2009/0306577 A1 | 12/2009 | Akridge et al. | | |
| 2011/0087138 A1* | 4/2011 | Kahook | ............... | A61H 23/02 |
| | | | | 601/89 |
| 2011/0190668 A1 | 8/2011 | Mishelevich | | |
| 2011/0319794 A1 | 12/2011 | Gertner | | |
| 2012/0157895 A1* | 6/2012 | Barlow | ............... | A61B 5/7203 |
| | | | | 601/46 |
| 2013/0274598 A1 | 10/2013 | Han | | |
| 2014/0031845 A1* | 1/2014 | Rynerson | ............... | A61F 13/38 |
| | | | | 606/162 |
| 2014/0207033 A1 | 7/2014 | Hillila | | |
| 2014/0316310 A1 | 10/2014 | Ackermann et al. | | |
| 2015/0100001 A1 | 4/2015 | Bujak et al. | | |
| 2015/0148711 A1 | 5/2015 | Bujak et al. | | |
| 2016/0158548 A1 | 6/2016 | Ackermann et al. | | |
| 2016/0367806 A1 | 12/2016 | Kahook | | |
| 2017/0014299 A1* | 1/2017 | Miller | ............... | A61H 23/02 |
| 2017/0181924 A1* | 6/2017 | Thorpe | ............... | A61H 7/002 |
| 2018/0104514 A1 | 4/2018 | Gertner et al. | | |
| 2018/0161579 A1 | 6/2018 | Franke et al. | | |
| 2019/0151604 A1* | 5/2019 | Harper | ............... | A61H 39/007 |

FOREIGN PATENT DOCUMENTS

| | | |
|---|---|---|
| WO | WO-2013003594 A2 | 1/2013 |
| WO | WO-2018071839 A1 | 4/2018 |

OTHER PUBLICATIONS

Han, et al., Anatomy of the External Nasal Nerve. Plastic and Reconstructive Surgery: Oct. 2004—vol. 114—Issue 5—p. 1055-1059.
Levi; et al., "Levi, et al., Stimulation of the Sphenopalatine Ganglion Induces Reperfusion and Blood-Brain Barrier Protection in the Photothrombotic Stroke Model. Plos One, Jun. 22, 2012;".
Office Action dated Jan. 16, 2020 for U.S. Appl. No. 16/250,571.
Office action dated Aug. 20, 2019 for U.S. Appl. No. 16/250,571.
Reher, et al., Ultrasound stimulates nitric oxide and prostaglandin E2 production by human osteoblasts. Bone. Jul. 2002;31(1):236-41.
Supplemental Search Report EP17861134 dated Feb. 7, 2020.
Office action dated May 28, 2020 for U.S. Appl. No. 16/791,983.
Sheppard et al. "Characterization of tearproduction in subjects with dry eye disease during intranasal tearneurostimulation: Results from two pivotal clinical trials." The OcularSurface 17 (2019), pp. 142-150. (Year: 2019).

\* cited by examiner

THERAPEUTIC ULTRASOUND FOR EYE DISORDERS

CROSS-REFERENCE TO RELATED APPLICATIONS

This application is a continuation of U.S. patent application Ser. No. 16/250,571, filed Jan. 17, 2019, which is a continuation of U.S. patent application Ser. No. 15/783,872, filed Oct. 13, 2017, which claims the benefit of U.S. Provisional Application No. 62/521,362, filed Jun. 16, 2017; U.S. Provisional Application No. 62/509,238, filed May 24, 2017; U.S. Provisional Application No. 62/451,583, filed Jan. 27, 2017; U.S. Provisional Application No. 62/422,627, filed Nov. 16, 2016; and U.S. Provisional Application No. 62/410,115, filed Oct. 19, 2016; and U.S. Provisional Application No. 62/408,651, filed Oct. 14, 2016, each of which are incorporated herein by reference.

BACKGROUND OF THE INVENTION

1. Field of the Invention

The present invention relates generally medical devices and methods. More particularly, the present invention relates to devices and methods for treating an eye.

Therapeutic sound and ultrasound have become an increasingly common modality in treating medical disorders. The ability to deliver both sound and ultrasound non-invasively is of increasing interest in the medical community. In ophthalmology, therapeutic sound and ultrasound are of particular interest because of its non-invasive nature and ability to easily reach all structures inside the eye and because ultrasound imaging can easily image all the structures in the eye.

The inventions contained herein all utilize therapeutic sound or ultrasound in the treatment of disorders involving the head and neck. Sound and ultrasound are also contained in the broad category of mechanical vibration.

2. Description of the Background Art

A device to create tearing to treat dry eye has recently been developed (U.S. Pat. No. 9,440,065) which utilizes an intranasal neurostimulator to activate nerves in the nasal mucosa. This device is placed inside the nostrils and two prongs grab onto the septum after which electrical current is applied across the septum. According to the company and research in the field, the electrical stimulation activates the interior branch of the anterior ethmoidal nerve. Within a few minutes, tears are generated. A randomized showed that the device, when placed intranasally, compared to sham, was highly effective in producing tears (product brochure; www.truetear.com), tears which contain the typical concentration of proteins and glycoproteins. The sham procedure was one in which the same neurostimulation device and parameters were applied to the skin on the outer nostril. The sham procedure on the outer skin of the nostril did not change the baseline amount of tearing from baseline and served as an outstanding control. The intranasal neurostimulator was uncomfortable for many patients and resulted in a great number of side effects including an epistaxis rate of over 5 percent. Most patients also reported that they would not perform the procedure in public although their symptoms were dramatically improved.

Another dry eye treatment involves a procedure in which a lens is placed over the cornea and a device then compresses the eyelid between the device and the cornea, applying both pressure and heat (e.g. U.S. Pat. No. 7,976,573, www.tearscience.com). The procedure is performed in an ophthalmologist office and the device has been shown to open the glands on the inside of the eye, called Meibomian Glands (and the disease is called Meibomian Gland Disease or MGD). This device also had been shown to be effective for dry eye in clinical trials but is also cumbersome and expensive for an ophthalmologist and patients, lasting about 30 min to an hour inside a physician's office.

See also US2016/0158548; US2015/0100001; US2011/0319794; and US2011/0190668.

While these devices represent advances in the treatment of dry-eye, new methods and devices are needed to treat dry eye and associated lack of ability to produce tears and maintain sufficient Meibomian gland secretions. The devices should also be designed with a low cost and form factor which encourages compliance and facilitates their utilization. At least some of these advantages will be met by the inventions described herein below.

SUMMARY OF THE INVENTION

In an exemplary first aspect, the present invention provides a method for stimulating tear production in a patient. The method comprises positioning a vibratory surface at a bony region on the patient's face communicating with a parasympathetic nerve which innervates the lacrimal gland. The vibratory surface is vibrated at a frequency and a displacement selected to stimulate the lacrimal nerve to produce tears. Typically, the vibratory surface will stimulate an afferent which communicates with a parasympathetic nerve which stimulates glands related to the tear film.

The vibratory surface may be vibrated at any frequency effective to stimulate the target nerves, typically being in a range from 10 Hz to 1000 Hz, 10 Hz to 500 Hz, 10 Hz to 400 Hz, 10 Hz to 300 Hz, 10 Hz to 200 Hz, 10 Hz to 100 Hz, 10 Hz to 50 Hz, 50 Hz to 1000 Hz, 50 Hz to 500 Hz, 50 Hz to 400 Hz, 50 Hz to 300 Hz, 50 Hz to 200 Hz, 50 Hz to 100 Hz, 200 Hz to 1000 Hz, 200 Hz to 500 Hz, 200 Hz to 400 Hz, 200 Hz to 300 Hz, 300 Hz to 1000 Hz, 300 Hz to 500 Hz, 300 Hz to 400 Hz, or 400 Hz to 1000. Similarly, the vibratory surface may be vibrated at any displacement effective to stimulate the target nerves, typically being in a range from 0.1 mm to 5 mm, 0.25 mm to 5 mm, 0.5 mm to 5 mm, 1 mm to 5 mm, 0.1 mm to 3 mm, 0.25 mm to 3 mm, 0.5 mm to 3 mm, 1 mm to 3 mm, 0.1 mm to 5 mm, 0.25 mm to 2 mm, 0.5 mm to 2 mm, 1 mm to 2 mm, or 2 mm to 3 mm.

The vibratory surface typically has a skin contact area in a range from 0.5 $mm^2$ to 20 $mm^2$, 0.5 $mm^2$ to 10 $mm^2$, 0.5 $mm^2$ to 5 $mm^2$, 0.5 $mm^2$ to 2 $mm^2$, 0.5 $mm^2$ to 1.5 $mm^2$, 0.5 $mm^2$ to 1 $mm^2$, 1 $mm^2$ to 20 $mm^2$, 1 $mm^2$ to 10 $mm^2$, 1 $mm^2$ to 5 $mm^2$, 1 $mm^2$ to 2 $mm^2$, 1 $mm^2$ to 1.5 $mm^2$, 1.5 $mm^2$ to 20 $mm^2$, 0.5 $mm^2$ to 10 $mm^2$, 1.5 $mm^2$ to 5 $mm^2$, 1.5 $mm^2$ to 2 $mm^2$, 2 $mm^2$ to 20 $mm^2$, 2 $mm^2$ to 10 $mm^2$, 2 $mm^2$ to 5 $mm^2$, 2.5 $mm^2$ to 20 $mm^2$, 2.5 $mm^2$ to 10 $mm^2$, 2.5 $mm^2$ to 5 $mm^2$, 5 $mm^2$ to 20 $mm^2$, or 5 $mm^2$ to 10 $mm^2$.

The vibratory surface typically has a hardness in a range from Shore A40 to Shore A80, Shore A50 to Shore A80, Shore A60 to Shore A80, Shore A70 to Shore A80, Shore A40 to Shore A70, Shore A50 to Shore A70, Shore A60 to Shore A70, Shore A40 to Shore A60, Shore A50 to Shore A60, or Shore A40 to Shore A50.

The vibratory surface is usually formed on a polymeric interface body and may have a thickness in a range from 1 mm to 10 mm, 2 mm to 10 mm, 3 mm to 10 mm, 4 mm to 01 mm, 5 mm to 10 mm, 6 mm to 10 mm, 7 mm to 10 mm, 8 mm to 10 mm, 9 mm to 10 mm, 1 mm to 5 mm, 2 mm to 5 mm, 3 mm to 5 mm, 4 mm to 5 mm, 1 mm to 4 mm, 2 mm to 4 mm, 3 mm to 4 mm, 1 mm to 3 mm, 2 mm to 3 mm, or 1 mm to 2 mm.

The polymeric interface body may have a rounded edge circumscribing at least a portion of the vibratory surface. Such a rounded edge may have a radius in a range from 0.5 mm to 5 mm, 1 mm to 5 mm, 2 mm to 5 mm, 3 mm to 5 mm, 4 mm to 5 mm, 0.5 mm to 4 mm, 1 mm to 4 mm, 2 mm to 4 mm, 3 mm to 4 mm, 0.5 mm to 3 mm, 1 mm to 3 mm, 2 mm to 3 mm, 0.5 mm to 2 mm, 1 mm to 2 mm, and 0.5 mm to 1 mm. Alternatively, the polymeric interface body may have a square edge circumscribing at least a portion of the vibratory surface. The edge may or may not have the same properties as a central portion of the vibratory surface. For example, the polymeric interface body may have a rigid edge circumscribing at least a portion of the vibratory surface. The method of any one of claim 1, wherein the vibratory surface is vibrated with a pulsed duty cycle or 90%, 75%, 50%, 25% or 10%.

In some embodiments, a peak displacement of the vibratory surface may be increased when the duty cycle is less than 100%.

In some embodiments, the vibratory surface may be positioned on the patient's face at a location where the patient's upper lateral nasal cartilage meets the patient's nasal bone. In such cases, the vibratory surface may be engaged against the patient's face with an upward directionality.

In some embodiments, the vibratory surface may be positioned at a location from 6.5 mm to 8.5 mm lateral to the patient's nasal midline at the region.

In some embodiments, the vibratory surface may be positioned proximate or over the parasympathetic nerve which innervates the lacrimal gland and travels through the sphenopalatine ganglia located close to the maxillary bone in the sphenopalatine fossa.

In some embodiments, the vibratory surface may be positioned by engaging the vibratory surface on a hand held device against the bony region. Usually, a patient engages the vibratory surface of the hand held device against the bony region.

In some embodiments, the vibratory surface moves in a substantially linear direction in one dimension. For example, the vibratory surface may be driven in a substantially linear direction with an excursion of 0.5 to 2 mm.

In some embodiments, the vibratory surface may be placed in a position to stimulate the external nasal nerve.

In an exemplary second aspect, the present invention provides a handheld device for stimulating tear production in a patient. The device comprises a housing having a vibratory surface configured to engage a bony region on the patient's face over an afferent nerve which communicates with a parasympathetic nerve which innervates glands related to the tear film. Circuitry within the housing is configured to vibrate the vibratory surface at a frequency and a displacement selected to stimulate the afferent nerve, the lacrimal nerve to produce tears, and the Meibomian glands to produce oils to maintain the tear film.

Exemplary frequencies, displacements, skin contact areas for the vibratory surfaces, and other design features of the vibratory surfaces and devices have been set forth above with respect to the first exemplary aspects of the present invention.

In other aspects of the methods and hand held device of the present invention, the device circuitry may be configured to vibrate vibratory surface with a pulsed duty cycle or 90%, 75%, 50%, 25% or 10%. In specific embodiments, the circuitry may be configured to increase a peak displacement of the vibratory surface when the duty cycle is less than 100%.

The hand held device may be configured to be positioned by the patient so that the vibratory surface engages the vibratory surface against the bony region.

The circuitry may be configured to allow adjustment of the vibrational frequency. For example, the hand held device may include a manual frequency adjustment interface.

In an exemplary third aspect, the present invention provides a method for stimulating tear production in a patient. The method comprising (a) retracting an eyelid and (b) engaging a vibratory surface against the retracted eyelid at a frequency and a displacement selected to stimulate tear production, Meibomian gland secretion, or both.

In this method, the retracted eyelid may be compressed between a retractor and a compression member, and a vibratory surface may be engaged against the retracted eyelid by energizing at least one transducer on at least one of the retractor and the compression member.

The at least one transducer will typically be an ultrasound transducer operating at a frequency in a range from 20 kHz to 30 MHz or from 3 MHz and 10 MHz, and the ultrasound vibration typically penetrates the eyelid and heats a tissue plane inside the lid such that a surface of the eyelid remains substantially at body temperature (38° C. to 40° C.) while the inner eyelid is heated to from (42° C. to 48° C.).

In an exemplary fourth aspect, the present invention provides a hand held device for stimulating tear production in a patient. The device comprises a retractor having an eyelid-engaging end and a handle end. A vibrational transducer is located on the eyelid-engaging end of the retractor and is configured to deliver vibrational energy into the eyelid when the eyelid is engaged by the eyelid-engaging end of the retractor.

The vibrational transducer of the hand held device is typically at least one ultrasonic vibrational transducer, usually operating at a frequency in a range from 20 kHz to 30 MHz or from 3 MHz and 10 MHz. The hand held device may further comprise at least one non-ultrasonic vibrational transducer, typically operating at a frequency in a range from 10 Hz to 1000 Hz, 10 Hz to 500 Hz, 10 Hz to 400 Hz, 10 Hz to 300 Hz, 10 Hz to 200 Hz, 10 Hz to 100 Hz, 10 Hz to 50 Hz, 50 Hz to 1000 Hz, 50 Hz to 500 Hz, 50 Hz to 400 Hz, 50 Hz to 300 Hz, 50 Hz to 200 Hz, 50 Hz to 100 Hz, 200 Hz to 1000 Hz, 200 Hz to 500 Hz, 200 Hz to 400 Hz, 200 Hz to 300 Hz, 300 Hz to 1000 Hz, 300 Hz to 500 Hz, 300 Hz to 400 Hz, or 400 Hz to 1000 Hz.

In an exemplary fifth aspect, the present invention provides method for stimulating tear production in a patient. The method comprising (a) retracting an eyelid and (b) engaging a vibratory surface against the retracted eyelid at a frequency and a displacement selected to open Meibomian glands in the patient.

These methods may further comprising any one or more of measuring the temperature of the inner and/or outer eyelid, compressing the eyelid while the vibratory surface is applied, placing the vibratory surface against the inner portion of the eyelid, placing the vibratory surface against the outer part of the eyelid.

In an exemplary sixth aspect, the present invention provides hand held device for stimulating tear production in a patient. The device comprises a retractor having an eyelid-engaging end and a handle end. A pushrod having a distal member is configured to slide on the handle end to capture a patient's eyelid between the retractor and the distal member. A vibrational transducer on the eyelid-engaging end of the retractor is configured to deliver vibrational energy into the eyelid when the eyelid captured between the retractor and the distal member.

In particular examples of the hand held device, the pushrod may be spring-biased to open and manually advanced to close over the eyelid. The hand held device may further comprise a force gauge to indicate a force being applied to the eyelid. The vibrational transducer may generate ultrasound at frequencies from 20 KHz to 30 MHz to heat the eyelid to disrupt inspissation in blocked ducts. Alternatively, the vibrational transducer may generates ultrasound at frequencies from 500 kHz and 3 MHz to heat the eyelid to disrupt inspissation in blocked ducts. The hand held device may further comprise a control system to maintain a temperature between 40° C. and 47° C.

In one embodiment, an ultrasound adjunct for placement inside an eyelid to augment the ability to apply heat to the inside of the eyelid while protecting the surface of the eye is described.

In one embodiment, therapeutic ultrasound is projected to the posterior vitreous to repair or prevent a macular hole by completing a posterior vitreal detachment.

In some embodiments, therapeutic ultrasound is utilized to improve (speed and quantity) of drug delivery to structures including the retina, eyelid and associated glands and structures, the optic nerve, the lens, the trabecular meshwork, the cornea, and the anterior chamber of the eye.

In some embodiments, therapeutic ultrasound is utilized to open water pores in the retina to deliver drugs, genes, or materials to the retina and/or choroid.

In some embodiments, therapeutic ultrasound is utilized to mix drugs in the posterior vitreous cavity.

In some embodiments, therapeutic ultrasound is utilized to propel bioactive agents to the posterior of the eye.

In some embodiments, therapeutic ultrasound is utilized to repair injured retinal cells with low intensity stimulation of the retina.

In some embodiments, therapeutic ultrasound is used to break up floating debris in the vitreous.

In some embodiments, therapeutic ultrasound is used to liquefy the posterior vitreous to treat floaters.

In some embodiments, therapeutic ultrasound is utilized to create localized regions of drug uptake within the retina or the optic nerve.

In some embodiments, therapeutic ultrasound is utilized to assist in emulsifying the lens.

In some embodiments, therapeutic ultrasound is utilized to open up trabeculae and allow drainage of aqueous humor to decrease intra-ocular pressure.

In some embodiments, therapeutic ultrasound is utilized to inhibit fluid production from the ciliary processes in the eye.

In some embodiments, the therapeutic ultrasound is focused.

In some embodiments, the therapeutic ultrasound is unfocused or softly focused on the posterior vitreous cavity or other ocular structure being treated.

In some embodiments, therapeutic ultrasound is coupled to an imaging modality such as Optical Coherence Tomography, Ultrasound imaging, CT, MRI, optical imaging, and fluorescein angiography.

In some embodiments, therapeutic ultrasound is coupled to a laser beam.

In some embodiments, therapeutic ultrasound is coupled to ophthalmic imaging.

In some embodiments, therapeutic ultrasound is coupled to optical coherence tomography.

In some embodiments, therapeutic ultrasound is utilized to break up blood clots within blood vessels in the eye.

In some embodiments, therapeutic ultrasound is coupled to administration of systemic pharmaceutical agents.

In some embodiments, therapeutic ultrasound to the retina is coupled to treatment with systemically administered lytic agents to enhance breakup of clots in the retina.

In some embodiments, therapeutic ultrasound is utilized in combination with ultrasound sensitizing agents to enhance the effect.

In some embodiments, therapeutic ultrasound is utilized in combination with microbubbles.

In some embodiments, therapeutic ultrasound is utilized in combination with genetically engineered viruses or proteins, the therapeutic ultrasound stimulating or enhancing uptake of the viruses or proteins.

In some embodiments, therapeutic ultrasound is utilized in combination with ultrasound sensitive proteins, nanoparticles, or other bioactive materials.

In some embodiments, high intensity focused therapeutic ultrasound is utilized to create histotripsy damage in structures of the eye.

In some embodiments, a frequency below 1 megahertz is utilized.

In some embodiments, a frequency greater than 1 megahertz is utilized.

In some embodiments, low intensity is utilized to create a therapeutic effect.

In some embodiments, frequency between 50 and 300 Hz is utilized.

In some embodiments, high intensity ultrasound is utilized to create a therapeutic effect.

In some embodiments, ionizing radiation is used in combination with therapeutic ultrasound.

In some embodiments, therapeutic ultrasound is utilized to break up fibrotic tissues in the retina and allow for improved drug access.

In some embodiments, therapeutic sound or ultrasound or mechanical vibrations is utilized to treat dry eye by stimulating the lacrimal glands or the nasolacrimal duct.

In some embodiments, therapeutic ultrasound is utilized to stimulate nerves which travel to the lacrimal gland in the eye.

In some embodiments, therapeutic ultrasound is utilized to open up Meibomian glands inside an eyelid.

In some embodiments, therapeutic ultrasound or sound is utilized to stimulate a lacrimal duct via the nose in a patient.

In some embodiments, therapeutic sound or ultrasound is utilized to stimulate secretion of tears.

In some embodiments, therapeutic sound or ultrasound or mechanical vibration is utilized to stimulate the external branch of the anterior ethmoidal nerve (external nasal nerve) to create tears or decongest the sinus or nasal cavities.

In some embodiments, therapeutic ultrasound sound or mechanical vibration is utilized to decrease outflow from ciliary processes to treat elevated intraocular pressure.

In some embodiments, therapeutic ultrasound is utilized to increase the pore size within the trabecular meshwork of the eye to allow increased outflow and decrease intraocular pressure.

In some embodiments, therapeutic ultrasound is utilized to enhance drug delivery to the aqueous humor in the front the eye.

In some embodiments, therapeutic ultrasound is utilized to enhance drug delivery to treat glaucoma.

In some embodiments, therapeutic sound or ultrasound or vibration is utilized to treat red-eye.

In some embodiments, therapeutic ultrasound is utilized to treat infected tissues in the eye.

In some embodiments, therapeutic sound, ultrasound, or mechanical vibration is utilized to treat macular degeneration.

In some embodiments, therapeutic sound, vibration, or ultrasound is utilized to treat or prevent dry macular degeneration.

In some embodiments, therapeutic ultrasound is utilized to treat or prevent the formation of pterygium.

In some embodiments, therapeutic sound, vibration, or ultrasound is utilized to enhance drug delivery to the eyelid.

In some embodiments, therapeutic ultrasound utilized to enhance drug delivery to the eyelashes to improve their appearance or enhance their growth.

In some embodiments, therapeutic ultrasound, vibration, or sound is utilized to enhance eyelash growth with or without the addition of pharmaceutical agents.

In some embodiments, therapeutic ultrasound is utilized to enhance drug uptake to improve healing after a surgical procedure to the cornea.

In some embodiments, therapeutic ultrasound is utilized to remove or tighten loose or wrinkled skin of the eye of around the eyelid.

In some embodiments, therapeutic ultrasound is utilized to aid in healing of the retina with or without drug delivery after a surgical procedure.

In some embodiments, therapeutic ultrasound is utilized to apply force to retina to push fluids into the retina or through Bruch's membrane, the choroid, or the choriocapillaris layer of the retina.

In any of the embodiments of this invention, therapeutic ultrasound is replaced with therapeutic sound such as with frequency below 1000 Hz or straight mechanical vibration without sound.

In any of the embodiments above, therapeutic ultrasound is replaced with therapeutic sound such as sound with a frequency below 500 Hz.

In some embodiments, therapeutic sound is coupled to skin covering bony structures and a frequency of sound is applied to the skin such that the bone underneath resonates in response to the sound and the resonation through the bone activates nerves in close proximity to the bone.

In some embodiments, therapeutic sound is delivered through end effectors which propagate the sound and transduce it to the bony structures of the head and neck with optimal safety and effectiveness.

In some embodiments, therapeutic sound is used to stimulate the sphenopalatine ganglia and associated nerves in the pterygopalatine fossa by transducing sound through the skin overlying the maxillary bone.

In some embodiments, therapeutic sound or ultrasound is used to stimulate the sphenopalatine ganglia and interfere with migraines, cluster headaches, or seizures.

In some embodiments, therapeutic sound, vibration, or ultrasound is used to stimulate saliva production.

In some embodiments, therapeutic sound, vibration, or ultrasound is utilized to stimulate the external branch of the anterior ethmoidal nerve (external nasal nerve) at the region of the nose where the nasal bone meets the lateral process of the septal nasal cartilage.

In some embodiments, therapeutic sound or ultrasound is utilized to stimulate the sphenopalatine ganglia to treat cold symptoms such as stuffed or congested nasal passageways.

In some embodiments, therapeutic sound, vibration, or ultrasound is utilized to inhibit the sphenopalatine ganglia.

In some embodiments, therapeutic sound, vibration, or ultrasound is utilized to treat or eliminate wrinkles or loose skin of the eyelids of an eye.

In some embodiments, external ultrasound and/or mechanical vibration are applied to a nerve of the facial region to treat headache, rhinitis, depression, Alzheimer's disease, stroke, Parkinson disease, Meniere's disease, tinnitus.

In some embodiments, external ultrasound and/or mechanical vibration are applied to the region where the nasal bone meets the nasal cartilage to stimulate the nerves related to the sphenopalatine ganglia or the ethmoidal nerves to increase tears and to treat dry eye.

The following numbered clauses represent other specific aspects of the present invention:

1. A method to treat a nerve of the facial region comprising:

a. Applying a handheld device with an applicator tip to the skin of a face of a patient, the skin covering a facial bony region immediately thereunder;

b. Depressing the applicatory tip on the skin toward the bone of the face of the patient such that further depression is prevented;

c. Delivering vibratory energy from the handheld device, through the applicator tip of the device, through the skin of the patient and through the bone of the patient to stimulate or inhibit a nerve of the head and neck region of the patient.

2. The method of clause 1 wherein the vibratory energy has a frequency from about 50 Hz to about 1 KHz.

3. The method of clause 1 wherein the vibratory energy has a frequency from about 100 Hz to about 500 Hz.

4. The method of clause 1 wherein the handheld device is applied to the side of a nose of patient and depressed against the nasal bone along the side of the nose at the region where the cartilage meets the bone to stimulate tears in the patient.

5. The method of clause 1 wherein the handheld device is applied to the side of a nose of the patient at the location where the nasal cartilage and the nasal bone meet.

6. The method of clause 1 wherein the handheld device is depressed along the side of the nose at the location where the nasal cartilage and the nasal bone meet; and, applying a finger to the contralateral side of the nose concomitantly.

7. The method of clause 1 wherein the handheld device is applied to both sides of the nose of the patient either simultaneously or sequentially during therapy.

8. The method of clause 1 wherein the handheld device delivers vibratory energy at a decibel level less than about 20 db.

9. The method of clause 1 where the handheld device delivers the vibratory energy at a decibel level less than about 10 db.

10. The method of clause 1 further comprising: stimulating a nerve of the head and neck region to create tearing from the eye.

11. The method of clause 1 further comprising: stimulating a sphenopalatine ganglia of the patient to generate tears from the lacrimal gland of the patient.

12. The method of clause 1 further comprising: stimulating the nasolacrimal duct to generate tears in the eye of the patient.

13. The method of clause 1 wherein the vibratory frequency is adjusted to optimize the stimulation or inhibition of the nerve.

14. The method of clause 1 wherein the vibratory amplitude is adjusted to optimize the stimulation or inhibition of the nerve.

15. The method of clause 1 further comprising: attaching the applicator tip to a finger tip and pressing the finger tip to the skin of the nose in the region where the nasal bone meets the nasal cartilage.

16. The method of clause 1 further comprising attaching the applicator tip to two fingers; and, applying the vibratory energy to the bone by pinching the region of the nose with the two fingers.

17. The method of clause 1 further comprising: holding the applicator to one side of the nose with a first hand while adjusting its pressure on the skin by pressing against the other side of the nose with a different finger of the same hand.

18. The method of clause 1 further comprising one of: adjusting the angle of application, the pressure against the skin, and the type of applicator tip based on feedback from the patient of a sensation of tearing.

19. The method of clause 1 further comprising touching the applicator tip to a region of the face to affect a change in a congestion condition such as one of: sinusitis, nasal congestion, and rhinitis.

20. A device to stimulate a nerve in the head and neck region of a patient comprising:
 a. an applicator with a connected applicator handle, an actuator coupled to the handheld applicator, and a body surface interface mechanically coupled to the actuator;
 b. wherein the actuator moves mechanically at a frequency driven by an electric current and voltage to generate vibrational energy;
 c. and, wherein the body surface interface is adapted to couple to a skin interface of the head and neck region of the patient to transmit vibrational energy to a bone through the skin, and to stimulate a nerve acoustically coupled to the bone through the skin.

21. The device of clause 20 wherein the actuator vibrates at a frequency of between 100 and 300 Hz.

22. The device of clause 20 wherein the actuator is coupled to a material such that the material moves with a planar excursion of about 500 microns and not more than about 1500 microns.

23. The device of clause 20 wherein the body surface interface is adapted to couple to a nasal bridge.

24. The device of clause 20 wherein the body surface interface is adapted to simultaneously couple to both sides of a nose.

25. The device of clause 20 wherein the body surface interface has the compliance of a pencil eraser.

26. The device of clause 20 wherein the handheld applicator is adapted to be worn on a wrist and the actuator is separated from the handheld actuator by a flexible wire.

27. The device of clause 26 wherein the handheld applicator further comprises a portable battery.

28. The device of clause 20 wherein the nerve is part of, or communicates with, a sphenopalatine ganglia.

29. The device of clause 20 wherein the vibrational energy is configured to resonate with the bone overlying the nerve to stimulate the nerve.

30. The device of clause 20 wherein the skin surface interface is adapted to be grasped between the fingers of the patient.

31. The device of clause 20 wherein the skin surface interface is connected to a pair of spectacles.

32. The device of clause 20 wherein the skin surface interface further comprises a combination of a rigid material and a malleable material.

33. The device of clause 32 wherein the skin surface interface further is adapted to direct the vibrational energy preferentially in one direction to couple the vibrational energy to the bone underlying the skin and the handheld applicator is isolated from the movement and vibration.

34. The device of clause 20 wherein the nerve is a branch of facial nerve.

35. The device of clause 20 wherein the nerve is a lacrimal nerve.

36. The device of clause 20 wherein the nerve is a nerve which innervates a parotid or salivary gland.

37. The device of clause 20 further comprising an adjustment control to vary the vibration frequency and/or the amplitude of the actuator.

38. The device of clause 20 wherein the applicator is handheld.

39. The device of clause 20 wherein the applicator is configured to be attached to a finger.

40. The device of clause 20 wherein the applicator is configured to be attached to two fingers such that the bridge of the nose can be pinched with two actuators to transmit vibration to the nerve of the head or neck region simultaneously.

41. The device of clause 20 wherein the applicator is configured to be attached to the wrist of the patient.

42. The device of clause 20 wherein the applicator is configured to be attached to a pair of spectacles.

43. The device of clause 20 wherein the applicator is configured to be applied to an eyelid appliance.

44. The device of clause 20 wherein the body surface interface is adapted to couple vibrations from the actuator to the bone underneath the skin.

45. The device of clause 20 wherein the body surface interface comprises a semi-rigid material.

46. The device of clause 20 wherein the body surface interface is adapted to couple to the finger of a user and wherein the body surface interface further comprises a second interface which couples to a second finger of a user.

47. The device of clause 20 wherein the body surface interface comprises a shape memory material to facilitate form fitting to the tissue of the outer region of a nose of a user.

48. The device of clause 20 further comprising a controller which enables modulation of the amplitude of the vibration of the body surface interface.

49. The device of clause 20 wherein the vibrational energy is adapted to activate a pressure sensitive nerve.

50. The device of clause 20 wherein the actuator imparts motion to the body surface interface in which the motion is linear and is adapted to apply to the skin surface so that the motion is approximately perpendicular to the skin surface.

51. The device of clause 20 wherein the actuator imparts motion to the body surface interface in which the motion is linear and is adapted to apply to the skin surface so that the motion is perpendicular to the skin surface and can be adjusted so that the motion is applicable at an angle to the skin surface.

52. The device of clause 20 wherein the actuator imparts motion to the body surface interface in which the motion is linear and is adapted to apply to the skin surface while vibrations to the hand of the user are minimized.

54. The device of clause 20 wherein the actuator is electrically connected to a controller in which the controller imparts an adjustable frequency control.

55. The device of clause 20 wherein the actuator is electrically connected to a controller in which the controller imparts an adjustable amplitude control.

57. The device of clause 20 wherein the actuator is a solenoid with an electromagnet to impart linear direction to the body surface interface.

59. The device of clause 20 wherein the actuator is a speaker or a voice activated coil.

60. The device of clause 20 wherein the actuator has a linear actuator component vibrations are isolated from the user of the device.

61. The device of clause 20 wherein the body surface interface is rigid with an edge of approximately 1-2 mm width and configured to fit in the ridge at the junction of the nasal bone and nasal cartilage.

62. The device of clause 20 wherein the body surface interface further comprises an edge adapted to at least partially retract an eyelid.

63. The device of clause 20 wherein the actuator is connected to cam and wherein the cam drives a piston to create a linear motion.

64. The device of clause 63 wherein the cam is attached to a rod which connects to a position offset from the central axis of the motor so as to create a linear motion of the piston, the excursion of which is proportional to the offset from the central axis.

65. The device of clause 64 wherein the offset results in a 1 mm excursion of the piston.

66. The device of clause 64 wherein the offset results in a 2 mm excursion of the piston.

67. The device of clause 64 wherein the offset results in a 0.5 mm excursion of the piston.

68. The device of clause 64 further comprising an electronic control circuit wherein the electronic control circuit outputs a programmable voltage which determines the revolutions per minute of the motor and therefore the excursion frequency of the piston.

69. The device of clause 63 wherein the linear motion applicator is adapted to apply a force of about 1N to 5N to a region of the face overlying a nerve to activate the nerve with periodic application of this force through the skin to reach the nerve underlying the skin to create a clinical effect in a patient.

70. A method to treat a patient with a headache comprising:
a. applying a handheld device to the skin overlying a nerve on the face which communicates with an autonomic nervous center, the handheld device configured to generate pressure waves;
b. activating the handheld device at the time of a headache to transmit the pressure waves through the skin and through the bone to activate the autonomic nervous system.

71. The method of clause 70 further comprising applying sound waves across the skin to activate the autonomic nervous system.

72. The method of clause 70 further comprising: placing the handheld device on the region along the skin along the side of the nose where the nasal bone and the nasal cartilage meet; firmly pressing into this region; and, applying vibratory energy from the handheld device with a frequency of about 100-300 Hz and an excursion of the device tip of about 0.5 mm to about 1.5 mm.

73. The method of clause 70 further comprising targeting the anterior ethmoidal nerve.

74. The method of clause 70 further comprising: setting the handheld device to generate ultrasound pressure waves with frequency of about 500 kHz to about 5 MHz.

75. The method of clause 70 further comprising activation the anterior ethmoidal nerve.

76. The method of clause 70 further comprising applying pressure to the handheld device along the skin of the patient so that the patient feels a sneezing or tearing sensation.

77. The method of clause 70 further comprising applying a range of frequencies of pressure waves to determine the optimal frequency and degree of pressure to achieve the effect of preventing the headache.

78. The method of 70 wherein a sphenopalatine ganglia is activated by applying the handheld device to the external nasal nerve.

79. A method to treat a nerve of the facial region comprising:
a. applying a handheld device with an applicator tip to the skin of a face of a patient, the skin covering a bony region of the face;
b. depressing the application tip on the skin toward the bone of the face of the patient;
c. delivering vibratory energy from the handheld device, through the applicator tip of the device, through the skin of the patient and through the bone of the patient to create a biologic effect in a mucosal region underlying the bone.

80. The method of clause 79 further comprising: delivering the vibratory energy via applicator tip with a frequency of approximately 100-300 Hz and an excursion of 0.5 m to 2.0 mm.

81. The method of clause 79 further comprising: delivering vibratory energy via applicator tip with a frequency of approximately 300 Hz to 50 kHz.

82. The method of clause 79 further comprising: delivering vibratory energy via applicator tip with a frequency of approximately 50 kHz to 10 MHz.

83. The method of clause 79 further comprising: delivery a bioactive agent before, during, or after the vibratory energy.

84. The method of clause 79 further comprising applying the vibratory energy to an implant.

85. The method of clause 79 further comprising applying the vibratory energy before, during, or after a surgical procedure.

86. The method of clause 79 further comprising applying at least two different modes of vibratory energy simultaneously to effect a change in the mucosa of the sinus.

87. A method to treat a nerve of the facial region comprising:
a. applying a handheld device with an applicator tip to the skin of a face of a patient, the skin covering a bony region of the face, the bony region coupled to an autonomic nerve;
b. depressing the application tip on the skin toward the bone of the face of the patient;
c. delivering vibratory energy from the handheld device, through the applicator tip of the device, through the skin of the patient and through the bone of the patient to create a biologic effect in a mucosal region underlying the bone.

88. The method of clause 87 wherein the mucosal region is a sinus cavity or a nasal passage.

89. The method of clause 87 wherein the vibratory energy has a frequency of between 50 Hz and 5 MHz.

90. The method of clause 87 wherein a bioactive agent is applied to the mucosa prior to application of the vibratory energy.

91. The method of clause 87 wherein the biologic effect is disruption of the biofilm layer in the mucosal region.

92. The method of clause 87 wherein the mucosal region contains a nerve.

93. The method of clause 87 further comprising: cycling the vibratory power with a duty cycle, a peak power, and an average power.

94. The method of clause 87 further comprising performing a surgical procedure prior to, during or after delivery of the vibrational energy.

95. The method of clause 87 further comprising locating a sinus or a region of congestion using an acoustic impulse.

96. The method of clause 87 further comprising: simultaneously utilizing multiple vibratory frequencies.

97. The method of clause 87 further comprising: applying one vibratory energy with a frequency between 50 and 300 Hz and a second vibratory energy of between about 1 MHz and 30 MHz.

98. The method of clause 87 further comprising: mapping the nerve anatomy of the nasal region prior to applying the vibratory energy.

99. The method of clause 87 further comprising: activating the activator tip to deliver vibratory energy with a frequency between 1 MHz and 10 MHz.

100. The method of clause 87 further comprising: activating the activator tip to deliver vibratory energy with a frequency between 0.5 MHz and 5 MHz.

101. The method of clause 87 further comprising: activating the activator tip to deliver a vibratory energy with a frequency between 50 Hz and 500 Hz.

102. The method of clause 87 further comprising: stimulating a parasympathetic nerve to create a tearing response.

103. The method of clause 87 further comprising: activating an implant to release a bioactive molecule into the mucosa.

104. The method of clause 87 further comprising: activating a polymer to release a bioactive molecule into the mucosa.

105. A method to treat patient with dry eye comprising:
a. applying a handheld device with an applicator tip to the skin of a face of a patient, the skin covering a bony region of the face;
b. depressing the applicator tip on the skin toward the bone of the face of the patient in the region where the nasal cartilage meets the nasal bone;
c. delivering vibratory energy from the handheld device with a frequency between 100 Hz and 400 Hz and an amplitude of the applicator tip greater than 500 microns to the region where the nasal cartilage meets the nasal bone to stimulate tears in the eyes of the patient.

106. The method of clause 105 further comprising: setting the frequency to a frequency between 150 and 200 Hz.

107. The method of clause 105 further comprising adding a bioactive agent to the wherein the feedback from the stimulation of the nerve is utilized to ensure the intended nerve has been treated 108. A method to treat a patient with nasal or sinus disease comprising:
a. applying a sound or ultrasound applicator to the skin surrounding the nasal sinuses;
b. setting an amplitude and a frequency of the applicator applied to the skin;
c. delivering sound or ultrasound energy from the applicator to the skin of the patient and through the skin of the patient to the nasal or sinus mucosa of the patient.

109. The method of clause 108 wherein the disease is an allergic disease and the sound or ultrasound overstimulates the nerves to inhibit their function in the allergic disease.

110. The method of clause 108 further comprising delivering the sound or ultrasound prior to, during, or after balloon sinuplasty.

111. The method of clause 108 wherein the sound or ultrasound comprises frequency between 50 Hz and 300 Hz.

112. The method of clause 108 further comprising delivering sound or ultrasound just prior to, during, or after a functional endoscopic sinus surgery procedure.

113. The method of clause 108 wherein the sound and ultrasound is delivered to the region of the external nasal nerve at the junction of the nasal cartilage and nasal bone.

114. The method of clause 108 further comprising delivering sound or ultrasound just prior to, during, or after delivery of a bioactive material into the nasal cavity.

115. A method of creating tears in a patient comprising:
a. gripping a device with one hand and applying it to provide for vibration at 100 to 300 Hz with an approximately linear excursion of the tip of the device of about 500 to 1500 microns;
b. applying the device to the region of the external part of the nose where the nasal cartilage meets the nasal bone;
c. activating the external nasal nerve.

116. The method of clause 115 further comprising applying a force of about 0.5N to about 3.0N to the external nasal nerve.

117. The method of clause 115 further comprising applying a force of about 0.5N to about 5.0N.

118. A device to apply vibrational energy to an eyelid of a patient comprising:
a. a handheld implement adapted to interface with an eyelid of an eye;
b. a retractor component connected to the handheld implement;
c. a sliding element adapted to slide along the retractor;
b. at least one piezoelectric element on at least a portion of the retractor element or the sliding element;
c. at least one temperature measuring element coupled to the retractor element, the sliding element, or both;
d. a processor configured to adjust temperature based on the temperature measuring element to maintain the temperature of the eyelid to about 39 C to 50 C.
e. a power supply.

119. The device of clause 118 wherein the handheld implement further comprises a linear resonant actuator configured to vibrate the interface of the retractor or the sliding element coupled with the eyelid at a frequency of between 100 Hz and 400 Hz.

120. The device of clause 119 wherein the linear resonant actuator, the piezoelectric element, and the pressure are applicable independently or together to treat dry eye.

121. The device of clause 118 wherein the processor is configured to supply a current to the piezoelectric element to oscillate the piezoelectric element at a frequency of between 1 MHz and 5 MHz 122. The device of clause 118 wherein the handheld implement further comprises a region on the implement through which manual pressure can be applied to the eyelid.

123. The device of clause 122 wherein the region is a compliant region.

124. The device of clause 118 wherein the processor is electrically coupled to the temperature measuring element.

125. The device of clause 118 wherein said distal end of said implement is adapted to retract an eyelid.

126. The device of clause 125 wherein said distal end of said implement is comprised of a hydrogel coating.

127. The device of clause 125 wherein said distal end of said implement is comprised of a biocompatible silicone coating.

128. The device of clause 118 wherein said distal end of said implement is comprised of a PTFE coating.

129. The device or clause 118 wherein said sliding element is coupled to a strain gauge operative to measure pressure applied to the eyelid when the sliding element is in its operative position against the eyelid.

130. The device of clause 118 wherein said sliding element is coupled to a strain gauge operative to measure pressure applied to the eyelid when the sliding element is in its operative position against the eyelid and to further signal to the user that the strain and pressure have reached a pre-specified limit.

131. The device of clause 118 further comprising a base control unit

132. The device of clause 118 wherein said distal end comprises at least one thermistor to contact the inner eyelid when said eyelid is retracted.

133. The device of clause 118 further comprising a control box, said control box comprising digital controls to set at least one of temperature range, amplitude, duty cycle of the ultrasound, and number of active piezoelectric elements.

134. The device of clause 118 wherein the power supply is rechargeable and incorporated within a hand grip, the hand grip operatively attached to the device.

135. The device of clause 118 wherein the distal end of said implement is further configured to allow for pressure to be applied to an eyelid through the implement, the pressure applied to the eyelid by pressure from the operator of the implement compressing the lid through a compliant portion of the implement.

136. The device of clause 135 wherein the compliant portion comprises a flexible membrane.

137. The device of clause 135 wherein the compliant portions comprises an elastomer.

138. The device of clause 135 wherein the compliant portion further comprises a pressure sensor.

139. The device of clause 135 wherein the temperature measurement element comprises an infrared sensor.

140. The device of clause 135 wherein the temperature measurement element comprises a thermistor.

141. The device of clause 118 wherein the temperature measurement element collects data used in a model to predict temperature within the eyelid.

142. The device of 141 wherein the temperature prediction is utilized to control the on-off timing of the implement.

143. The device of clause 118 wherein the implement further comprises a vibratory actuator with a preset or adjustable frequency and an amplitude.

144. The device of clause 118 wherein the implement is further adapted to be depressed against the skin of an outer eyelid.

145. The device of clause 118 wherein the piezoelectric element delivers ultrasound energy between 1 and 30 MHz 146. The device of clause 118 wherein the piezoelectric element delivers ultrasound energy to the eyelid between 2 and 10 MHz 147. The device of clause 118 wherein the piezoelectric element is configured to deliver ultrasound energy to the Meibomian Glands.

148. The device of clause 118 wherein the piezoelectric element is configured on the implement to deliver energy through the eyelid from outside the eyelid.

149. A device to apply heat to an eyelid comprising:
 a. a handheld implement adapted to interface with an eyelid of an eye;
 b. at least one piezoelectric element;
 c. at least one temperature measuring element; and
 d. a processor configured to adjust temperature based on the temperature measuring element and a model which predicts the temperature inside an eyelid based on the temperature measuring element to maintain the temperature of the eyelid within a safe range.

150. The device of clause 149 wherein the temperature measuring element is an infrared sensor.

151. The device of clause 149 wherein the temperature measuring element is an ultrasound detector.

152. The device of clause 149 wherein the temperature measuring element is a thermistor.

153. The device of clause 149 wherein a processor is adapted to receive an input from the temperature measuring element and provide feedback to the piezoelectric element to control temperature of the device.

154. The device of clause 149 further incorporating an integrated eyelid retractor.

155. A method to treat dry eye comprising:
 a. applying a vibrating implement to a region proximate an eyelid or nose of a patient;
 b. determining a set of test vibration parameters of the implement;
 c. determining a location and optimal range of vibration frequency and amplitude of the implement based on patient and operator feedback;
 d. setting the vibration frequency and amplitude of the implement based on the patient and/or operator feedback.

156. The method of clause 155 wherein the implement further comprises ultrasound with frequency between 1 MHz and 30 MHz and the optimal frequency is determined by the patient/user.

157. The method of clause 155 wherein the location is set to the region where the nasal bone meets the nasal cartilage.

158. The method of clause 157 wherein the user further depresses the skin on the side of the face opposite the side where the implement is being applied.

159. The method of clause 159 wherein the user depresses the skin on the nose on the side opposite the placement of the implement and depresses the implement simultaneously to transmit vibrations and activate nerves on both sides of the face.

160. The method of clause 155 wherein the location is proximate an infra-orbital nerve.

161. The method of clause 155 wherein the location is proximate to a sphenopalatine ganglia.

162. The method of clause 155 where the location is proximate an ethmoidal nerve.

163. The method of clause 155 wherein the location is a lacrimal gland.

164. The method of clause 155 wherein the location is an accessory lacrimal gland.

165. The device of clause 155 wherein the location is the skin of the eyelid and the amplitude and frequency are chosen to eliminate out wrinkles it the eyelid.

166. The method of clause 155 wherein the vibration frequency is chosen from a frequency between 50 Hz and 300 Hz; and the amplitude is chosen from about 0.1 mm to about 1.5 mm; and wherein the amplitude is sinusoidal; and wherein the implement moves with a substantially linear motion.

167. A device to apply pressure and energy to the lid of an eye comprising:
 a. a first shaft adapted to pull a lid away from the sclera and cornea of a patient by gripping the inside of the eyelid;
 b. a second shaft operatively connected to the first shaft adapted to apply pressure to the outside of the eyelid and compress the eyelid against the first shaft; and c. an energy source located on the device operative to transmit energy to or from the eyelid through at least one of the first shaft and second shaft.

168. The device of clause 167 further comprising a vibratory element mechanically coupled to at least the first shaft and/or the second shaft.

169. The device of clause 167 further comprising an ultrasound element on the first and/or second shaft.

170. The device of clause 167 comprising a mechanism to apply pressure to the eyelid between the first shaft and the second shaft; and, a device which transduces vibration to the first and/or second shaft and thence to the eyelid.

171. The device of clause 167 further comprising at least one ultrasound element which generates ultrasound within a frequency range of about 1 MHz to about 15 MHz 172. The device of clause 167 further comprising a temperature sensing element.

173. The device of clause 167 wherein the first shaft and the second shaft are connected by a member said member comprising an elastic material attached between the first shaft and second shaft, said elastic material creating tension on the first and second shaft as the shafts move relative to one another.

174. The device of clause 167 wherein a housing surrounds the first and second shaft said housing comprising a compartment for a portable battery.

175. The device of clause 167 wherein electrical connections are tunneled through the shaft to reach the region of the device which contact the eyelids of the patient.

176. The Device of clause 167 wherein the energy source is at least one light emitting diode.

177. The device of clause 167 wherein the energy source is at least one light emitting diode which generates radiation in the wavelength range greater than 500 nm.

178. The device of clause 167 wherein the energy source operates to transfer energy from the eyelid to cool the eyelid.

179. The device of clause 167 wherein the

180. The device of clause 167 further comprising at least one temperature sensor.

181. The device of clause 167 wherein the first shaft and the second shaft are operatively attached through an elastic connector.

182. The device of clause 167 wherein the first shaft and the second shaft are operatively attached through an elastic connector and the excursion of one shaft relative the other shaft is quantitated through with a sensor which detects strain or incremental movement.

183. The device of clause 167 further comprising

184. A device to apply energy to the inside of the eyelid comprising:
  i. a distal tip configured to retract the eyelid; and
  ii. an energy source attached to the distal tip.

185. The device of clause 184 wherein the distal tip comprises an ultrasound energy source.

186. The device of clause 184 wherein the distal tip comprises a vibratory energy source which vibrates at between 50 and 400 Hz and an amplitude of between 500 microns and 3 mm.

187. The device of clause 184 wherein the distal tip comprises a second distal tip, mechanically coupled to the first distal tip in which pressure can be applied to the eyelid.

188. The device of clause 184 wherein the distal tip further comprises a suction apparatus, said suction apparatus configured to retract the lid away from the sclera of the eye whenst said energy source can be applied.

189. The device of clause 184 wherein the distal tip further comprises a suction apparatus configured to pinch the skin of the eyelid and apply energy through the pinched skin.

190. The device of clause 184 wherein the distal tip comprises graspers through which energy is applied to the eyelid when the skin of the eyelid is pinched.

191. The device of clause 184 wherein the device comprises a distal tip and said distal tip is configured to have a retractor to mechanically retract the eyelid from the sclera of the eye.

192. The device of clause 184 wherein the distal tip is configured to have a retractor to mechanically retract the eyelid 193. The device of clause 184 wherein the distal tip is configured to have a retractor to mechanically retract the eyelid and the distal tip is further configured to have an ultrasound element on the mechanical portion which retracts the eyelid.

194. The device of clause 184 wherein the distal tip is configured

195. A method to create tears and secretions from Meibomian glands comprising:
  a. retracting an eyelid of a patient;
  b. visualizing the mucocutaneous junction of the eyelid;
  c. locating a device proximate to the eyelid; and
  d. activating the device to apply transmit mechanical vibration from the end effector of a device to the mucocutaneous junction.

196. A method to generate tears in a human subject comprising:
  a. applying an applicator to an external region of a nose of a subject, the region located where the external branch of the anterior ethmoidal nerve exits to the skin alongside the nose; and
  b. activating the applicator to generate mechanical vibration at a frequency of between 100 and 300 Hz, the vibration generating a force on the skin and underlying nerve sufficient to activate the nerve.

197. The method of clause 196 further comprising: actively mapping nerves in the skin distributions on the face of a subject to determine the optimum location for stimulation of the exterior anterior ethmoidal nerve.

198. The method of clause 197 wherein the active mapping comprises stimulating the nerves in the skin distributions on the face of the subject with a range of frequencies of between 50 Hz and 300 Hz, a range of amplitudes between 0.5 mm and 3.0 mm and a range of forces between 0.5 N and 3N.

199. The method of clause 197 wherein the active mapping further comprises monitoring the effect of the stimulation of the nerves.

200. The method of clause 199 wherein the active mapping comprises monitoring one of: tearing, sneezing, and itching.

201. The method of clause 197 further comprising determining one of: optimum frequency, position, force, amplitude, duration, power, and duty cycle 202. The method of clause 199 further comprising: positioning the applicator specifically along the mapped regions.

203. A method to generate tears in a human subject comprising:
  a. applying an applicator to an external region of a nose of a subject, the region located where the external branch of the anterior ethmoidal nerve exits to the skin alongside the nose;

b. activating the applicator to generate mechanical vibration at a frequency of between 50 Hz and 300 Hz; and c. applying a force over an area of about 1 mm$^2$ to about 5 mm$^2$ on the skin and underlying nerve of approximately 0.5N to about 2N to activate the nerve.

204. The method of clause 203 further comprising

205. A device configured to activate tears in a human patient comprising:

a. an end effector configured to interface with the external skin over the region of the nose where the external nasal nerve exits the nasal bone;

b. a main body configured to be handheld; and c. an actuation mechanism coupled to the end effector and configured produce mechanical vibration of the end effector.

206. The device of clause 205 wherein the end effector is configured to apply 0.5 N to 3.0 N force over an area of about 1 mm$^2$ to about 5 mm$^2$.

207. The device of clause 205 wherein the end effector comprises an edge with and edge radius of curvature of 0.5 mm to 2.0 mm.

208. The device of clause 205 wherein the end effector comprises a notch to fit in the region of the interface of the nasal cartilage and nasal bone.

209. The device of clause 205 wherein the end effector further comprises a biocompatible material with a durometer between 20 A and 60 A.

210. The device of clause 205 wherein the end effector is actuated to move a distance of between 5 mm and 30 mm.

211. The device of clause 210 wherein the end effector is actuated to move a distance of between 5 mm and 30 mm while maintaining relatively constant force of between 0.5N and 3.0N.

212. The device of clause 205 wherein the actuator comprises a linear resonance actuator.

213. The device of clause 205 wherein the actuator comprises an eccentrically weighted motor.

214. The device of clause 205 wherein the actuator comprises a voice coil.

215. The device of clause 205 wherein the actuator comprises an electromagnet.

216. The device of clause 205 wherein the actuator comprises a piezoelectric crystal.

217. The device of clause 205 wherein the actuator is configured to accelerate the end effector with a linear motion.

218. The device of clause 205 wherein the actuator is configured to accelerate the end effector in a circular motion.

219. The device of clause 205 wherein the actuator is configured to accelerate the end effector in a sinusoidal pattern.

220. The device of clause 205 wherein the actuator is configured to accelerate the end effector in a programmable pattern.

221. The device of clause 205 wherein the actuator is configured to accelerate the end effector in a pattern which is programmable with a smart phone application.

222. A method for treating rhinitis, comprising: delivering a vibratory stimulus via a probe to treat rhinitis in a patient in need thereof, wherein the probe is in contact with one or more tissues of the nose of the patient during delivery of the vibratory stimulus.

223. The method of clause 222, wherein the electrical stimulus is delivered in response to one or more symptoms of rhinitis.

224. The method of clause 223, wherein the one or more symptoms of rhinitis comprise one or more of itching, sneezing, congestion, runny nose, post-nasal drip, mouth breathing, coughing, fatigue, headache, anosmia, phlegm, throat irritation, periorbital puffiness, watery eyes, ear pain, and fullness sensation.

225. The method of clause 222, wherein the vibratory stimulus is delivered more than once per day on a scheduled basis.

226. The method of clause 222, wherein the one or more tissues of the nose is the nasal mucosa.

227. The method of clause 222 wherein the one or more tissues of the nose is skin on the outside of the nose.

228. The method of clause 222, wherein the one or more nasal tissues is the mucosa adjacent to the nasal septum.

229. The method of clause 222, wherein the vibratory stimulus is a linear motion with an oscillation frequency of about 100 to 300 Hz.

230. A method of treating rhinitis, comprising: delivering a vibratory stimulus to a nasal tissue of a subject to improve rhinitis of the subject, wherein the vibratory stimulus is delivered via probe comprising a control subsystem to control the vibratory stimulus.

231. The method of clause 230, wherein the vibratory stimulus is delivered in response to one or more symptoms of rhinitis.

232. The method of clause 231, wherein the one or more symptoms of rhinitis comprise one or more of itching, sneezing, congestion, runny nose, post-nasal drip, mouth breathing, coughing, fatigue, headache, anosmia, phlegm, throat irritation, periorbital puffiness, watery eyes, ear pain, and fullness sensation.

233. The method of clause 232, wherein the vibratory stimulus is delivered at least once daily during a treatment period.

234. The method of clause 232, wherein the vibratory stimulus is delivered on a scheduled basis during the treatment period.

235. A method for treating ocular allergy, comprising: delivering a vibratory stimulus via probe to treat ocular allergy in a patient in need thereof, wherein the probe is in contact with nasal tissue of the patient during delivery of the vibratory stimulus.

236. The method of clause 235, wherein the vibratory stimulus is delivered in response to one or more symptoms of ocular allergy.

237. The method of clause 235, wherein the one or more symptoms of ocular allergy comprise one or more of swelling, puffiness, itching, tearing, and discharge.

238. The method of clause 235, wherein the nasal tissue is nasal mucosa.

239. The method of clause 235, wherein the nasal tissue is the external skin of the nose.

240. The method of clause 235, wherein the vibratory stimulus is a linear motion at approximately 100 Hz to 300 Hz.

241. A method of treating ocular allergy, comprising: delivering a vibratory stimulus to a nasal tissue of a subject to improve ocular allergy of the subject, wherein the vibratory stimulus is delivered by a probe of a stimulator comprising a control subsystem to control the vibratory stimulus.

242. The method of clause 235, wherein the electrical stimulus is delivered in response to one or more symptoms of ocular allergy.

243. The method of clause 236, wherein the one or more symptoms of ocular allergy comprise one or more of swelling, puffiness, itching, tearing, and discharge.

244. A method to treat narcolepsy comprising:

a. Positioning a vibratory surface at a bony region on the patient's face communicating with a parasympathetic nerve;

b. Vibrating the vibratory surface at a frequency and a displacement selected to stimulate the external nasal nerve.

245. A method to treat epilepsy comprising:
 a. Positioning a vibratory surface at a bony region on the patient's face communicating with a parasympathetic nerve;
 b. Vibrating the vibratory surface at a frequency and a displacement selected to stimulate the external nasal nerve.

246. A method to treat headaches comprising:
 a. Positioning a vibratory surface at a bony region on the patient's face communicating with a parasympathetic nerve;
 b. Vibrating the vibratory surface at a frequency and a displacement selected to stimulate the external nasal nerve.

247. A method to treat sinusitis comprising:
 a. Positioning a vibratory surface at a bony region on the patient's face communicating with a parasympathetic nerve;
 b. Vibrating the vibratory surface at a frequency and a displacement selected to stimulate the external nasal nerve.

248. A method to treat rhinitis comprising:
 a. Positioning a vibratory surface at a bony region on the patient's face communicating with a parasympathetic nerve;
 b. Vibrating the vibratory surface at a frequency and a displacement selected to stimulate the external nasal nerve.

INCORPORATION BY REFERENCE AND PRIORITY CLAUSES

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended clauses. A better understanding of the features and advantages of the present invention will be obtained by reference to the following detailed description that sets forth illustrative embodiments, in which the principles of the invention are utilized, and the accompanying drawings of which.

DETAILED DESCRIPTION OF THE INVENTION

Figure 1:
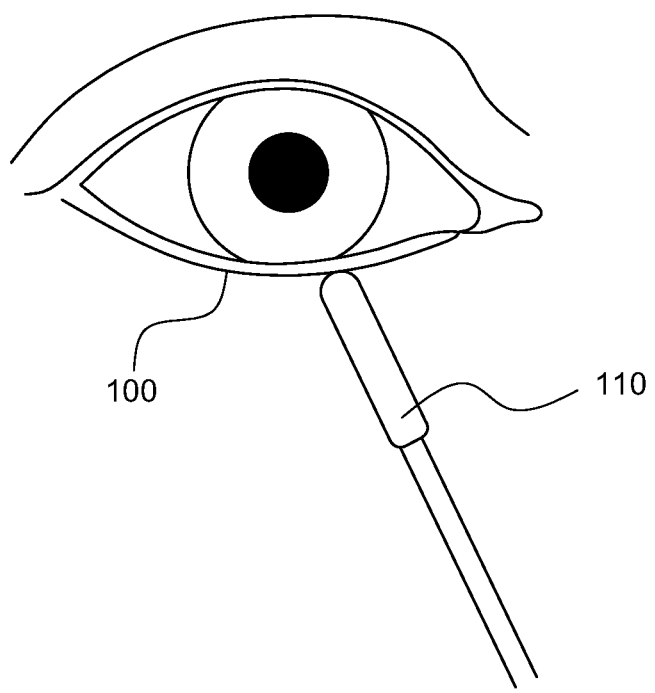
FIG. 1 depicts and ultrasound probe in proximity to an eyelid.

The inventions contained herein all pertain to utilizing mechanical force to treat disorders of the eye including disorders of the front of the eye and the back of the eye.

Sound and Ultrasound and vibration are utilized interchangeably in this invention description. Mechanical vibration at audible frequencies (20 to 20,000 Hz) may or may not actually transmit audible sound waves but may transmit force to a surface and is included in the broad definition of sound and ultrasound. Vibration, or mechanical vibration, is the broadest term and encompasses all sound or ultrasound regardless of whether pressure waves are created. Sound is simply mechanical vibration which transmits pressure waves through a medium which is then processed and "heard." Vibration as a category encompasses ultrasound and sound as well as mechanical vibration which may not result in sound. For example, mechanical vibration may be delivered by a probe with a linear motion, a planar motion, or motion in all three axes. The important aspect of mechanical vibration is the motion and a frequency of at least a few Hertz (Hz). The underlying mechanism of purposeful vibration (as opposed to unwanted vibration created incidentally to another mechanism such as a running motor) is to and from motion intentionally created by a moving mechanism along with transduction to another medium, for example, a body tissue of a human subject. The motion of the vibration can be created by a number of different mechanisms including motors with a gear and camshaft to create an offset, an eccentric motor, a linear resonant actuator, a voice coil, and a piezoelectric mechanism. In this respect, mechanical vibration is easier to create than sound.

The frequency of the sound waves may range from the low frequency sub audible range to the higher frequency inaudible ultrasound range. One device of the current invention preferentially reflects ultrasound at the inner surface of the eyelid to direct the heat to the inner portion of the eyelid while substantially preventing the heat from conducting to the eyeball. Another device is a retractor for the eyelid to pull the eyelid from the surface of the eye while applying the heat through the retractor. One method further enhances opening of the glands within the eyelid by combining the therapy with bioactive materials or gene delivery molecules on the inside of the gland. In other embodiments, therapeutic ultrasound is utilized to open the blood retinal barrier and allow gene and drug therapy with large molecules. In other embodiments, therapeutic ultrasound is utilized to create changes to the anterior portion of the eye. Methods and devices are also described which allow heat to safely be applied to the eyelid of an eye utilizing ultrasound passed through the eyelid. One device preferentially reflects ultrasound at its surface to direct the heat to the inner portion of the eyelid while substantially preventing the heat from contacting the eyeball. Another device retracts the eyelid from the surface of the eye while applying the heat and optionally applies a controlled amount of pressure, ultrasound, and mechanical vibrations. Another device applies cavitating ultrasound through the eyelid to enhance opening of the glands within the eyelid. One method further enhances opening of the glands within the eyelid by combining the therapy with bioactive materials on the inside of the gland.

Other devices treat dry eye by increasing the amount of tears in the eye. These devices act synergistically with devices which improve the quality of the tear film. These devices create tears by activating the sphenopalatine ganglion (indirectly or directly) and/or facial nerve branches, and/or ethmoidal nerves with ultrasound or sound or mechanical vibration externally applied through the skin of the nose. An example of a direct stimulation of the sphenopalatine ganglia is through stimulation of the ganglia itself. An example of indirect stimulation of the sphenopalatine ganglia is through activation of a sensory pathway which then communicates via reflex neural circuit to the sphenopalatine ganglia to increase output or tears. Another embodiment can treat a variety of disorders utilizing sound and/or ultrasound and/or vibration which is externally applied to the skin of the head and neck and activates nerves or nerve ganglia under the skin. Another embodiment applies vibratory energy to the mucosa inside of the nose or to the mucosa on the inside of the eyelids to treat dry eye.

The retinal blood vessels communicate with the cerebral blood vessels; access to the cerebral blood vessels also provides access to the blood vessels of the retina. According to one embodiment of this invention, a method and apparatus are provided to enhance delivery of therapeutic molecules across the blood brain barrier by stimulation of the sphenopalatine ganglia (SPG) and/or its outgoing parasympathetic tracts and/or another parasympathetic center; stimulation of the SPG has been shown to control the several important blood brain barrier effects [e.g. see Levi et. al. Stimulation of the Sphenopalatine Ganglion Induces Reperfusion and Blood-brain Barrier Protection in the Photothrombotic Stroke Model; PLoS One 2012; 7(6)]. Importantly, the method and apparatus stimulate the SPG through an external device, activating nerves close to the skin of nasal region which are connected biologically through a neural network or can be directly activated with vibration through the skin. The apparatus typically stimulates the parasympathetic nerve fibers of the SPG directly or indirectly, thereby inducing the middle and anterior cerebral arteries to dilate, and also causing the walls of these cerebral arteries walls to become more permeable to large molecules. In this manner, the movement of large pharmaceutical molecules from within blood vessels to the cerebral tissue is substantially increased. Preferably, therefore, this method can serve as a neurological drug delivery facilitator, without the sacrifices in molecular weight required by techniques of the prior art. In general, it is believed that substantially all pharmacological treatments aimed at cerebral cells for neurological and psychiatric disorders are amenable for use with these embodiments of the present invention. In particular, these embodiments may be adapted for use in the treatment of disorders such as brain tumors, epilepsy, Parkinson's disease, Alzheimer's disease, multiple sclerosis, schizophrenia, depression, stress, anxiety, and any other CNS disorders that are directly or indirectly affected by changes in cerebral blood flow or by BBB permeability changes.

In other embodiments, the SPG is stimulated as an acute treatment for migraines, cluster headaches, epilepsy, Parkinson's disease, Alzheimer's disease, multiple sclerosis, schizophrenia, depression, stress, anxiety, obsessive compulsive disorder, tremor, sinusitis, vasomotor rhinitis, allergic rhinitis, common (viral) cold, allergic conjunctivitis, glaucoma, xerostomia (dry mouth), and nasal polyposis.

The nasolacrimal apparatus is the physiological system containing the orbital structures for tear production and drainage. It consists of the lacrimal gland, the lacrimal canaliculi, and the nasolacrimal duct which communicates with the cavity of the nose. The innervation of the lacrimal apparatus involves both the sympathetic supply through the carotid plexus of nerves around the internal carotid artery, and parasympathetically from the lacrimal nucleus of the facial nerve in the brainstem. Signals travel from sensory (afferent) fibers around the face to the area of the salivary nucleus in the brainstem to activate the parasympathetic fibers which travel back to the sphenopalatine ganglia to synapse and then send terminal nerve fibers to innervate the lacrimal gland.

In one embodiment (FIG. 1), a device 110 is presented in which vibration or sound or ultrasound is applied directly to an eyelid 100 of a patient. The applied ultrasound may be in the low frequency range or higher frequency range; typically, low frequency ultrasound begins at about 20,000 Hz and higher frequency ultrasound begins around 500,000 Hz and up to even 100 MHz. In some embodiments, audible sound is also capable of delivering energy to the eyelid and for some applications, is preferred. Therefore, the range of sound delivered to the eyelid is from about 50 Hz to about 100 MHz. In some embodiments, it's direct mechanical movement of an interface which stimulates tear production. In some embodiments, different frequencies are used alone or in combination with one another. In some embodiments, higher frequencies are used in imaging and lower frequencies for therapy, each independently or in combination. Ultrasound can be applied by the device to the inner eyelid 100 and the ultrasound energy can travel through the inner eyelid 100. In some embodiments, vibration is utilized in combination with stimulation with electrical current.

As the ultrasound travels through the eyelid, in some embodiments, the ultrasonic waves vibrate structures such as tear ducts and Meibomian glands 130 (FIGS. 2-3), specifically tear ducts which may contain inspissated oils, or are otherwise blocked with material 135 (FIG. 3) preventing tears or tear components (e.g. oils, lipids, etc.) from being excreted into the tear film 160 of the eye. In one example, a disease which is treated is dry eye.

In another embodiment, eyelash growth is stimulated with mechanical vibration. For example, it has been shown in previous models in bone tissue that ultrasound delivered at 50 kHz and 1 MHz stimulates prostaglandin release (Bone 2002 Jul. 31; 236-41). Prostaglandin release has been considered the main mechanism of action for the pharmaceutical agent bimatoprost, an FDA approved agent to stimulate eye lash growth. Therefore, in one embodiment, a vibratory stimuli is utilized to upregulate prostaglandin synthesis and increase thickness of eyelashes in a subject. Indeed, any of the embodiments herein may be combined with pharmaceuticals.

Device 110 may be applied to the upper eyelid or the lower eyelid in some embodiments. In some embodiments, ultrasound devices are applied to both lids simultaneously. As described herein, device 110 may generate ultrasound, sound, or predominantly vibrate at high amplitude at lower inaudible frequencies (e.g. 100-300 Hz). Vibration may occur at Device 110 in some embodiments has a programmable frequency and in some embodiments, a programmable amplitude. Device 110 in some embodiments has a wettable (e.g. hydrogel) end in which a contact with the skin of the eyelid is facilitated (skin interface). In some embodiments, a silicone, or rubber skin interface is used. In some embodiments, microbubble or pharmaceutical adjuncts are added to the eyelid to facilitate disruption of the inspissated material and ultrasound can facilitate the distribution of the pharmaceuticals into the glands and lids. For example, a steroid or detergent can be introduced into the glands to facilitate break up of inspissated ducts and vibration applied to further enhance the effect of the pharmaceutical or chemical agents.

Figure 2:
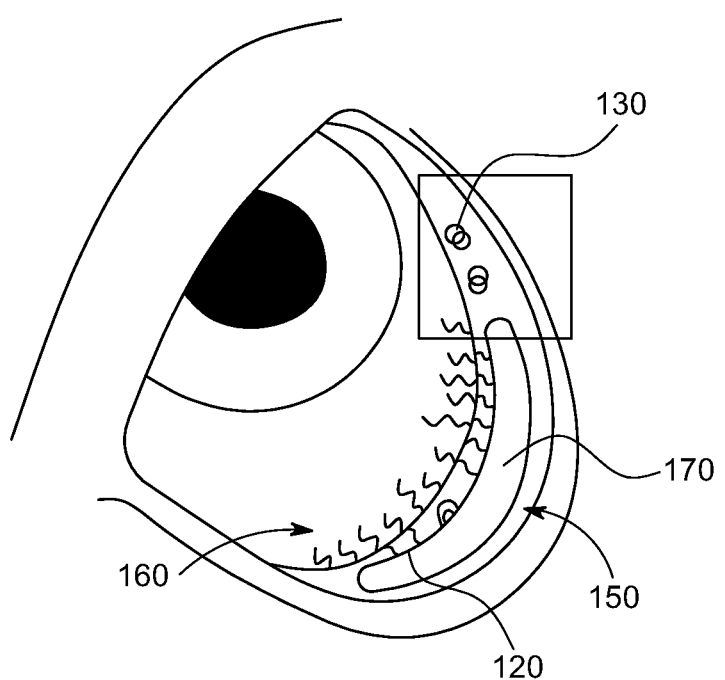
FIG. 2 depicts an ultrasound adjunct inside an eyelid.
Figure 3:
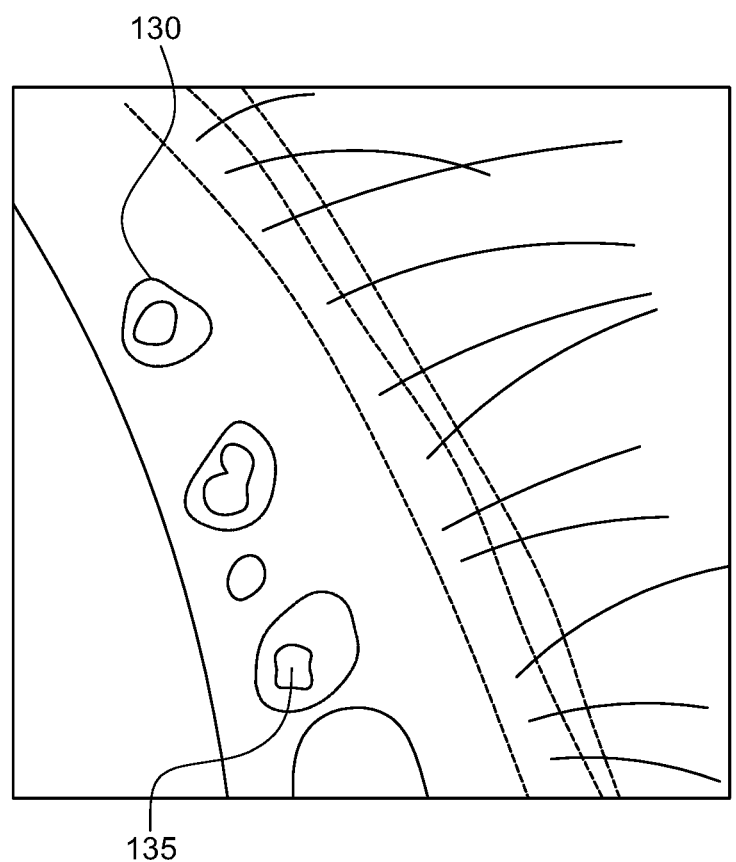
FIG. 3 depicts a tear duct with inspissated material.

FIG. 2 depicts an inner lid 150 and a Meibomian gland 130 with material 135 blocking the duct (FIG. 3). Ultrasound, sound, or vibration can be used to heat and/or vibrate the material 135 to remove it from the duct 130 (FIG. 3). Preferably, the ultrasound frequency chosen is one which resonates at the interface of the duct and the inspissated material to dislodge or heat the material in the duct so that the secretions from the duct can reach the eye and prevent dry eye. For example, early work has shown that sound frequencies in the 100 Hz to 500 Hz range will lead to break up of the material in the inspissated ducts. When combined with higher frequency ultrasound energy (e.g. 1 MHz to 3 MHz), the material can be heated to improve the efficiency of the unblocking of the ducts. In some preferred embodiments, temperature measurement is utilized to facilitate the safety and efficacy of the treatment; a temperature range of between 40 and 48 Celsius is the preferred temperature. The temperature can be controlled with closed loop control in which a thermistor is utilized to measure temperature and then the feedback through a control circuit is utilized to control the power output so as to maintain the temperature in a pre-specified range. In one embodiment, an ultrasound adjunct 170 (FIG. 2) is utilized to augment the ability of the ultrasound to heat the inner portion of the eyelid and protect the eye. In one embodiment, the adjunct 170 contains an interface which reflects ultrasound heat at the region of the interface between the adjunct and the inner portion of the eyelid 150. In one embodiment, this adjunct is stainless steel or other metal and is good reflector of ultrasound so that heat is generated at the interface with the glands and not at the surface of the cornea. The adjunct can be any material with an interface which reflects ultrasound such as a balloon with a gas inside. Ultrasound is reflected at interfaces and the interface created at the region of the adjunct is transmitted to the inner portion of the eyelid while the eye is protected. Heating will occur at the interface of the adjunct 170 and the eyelid. The adjunct in some embodiments contains an air interface which is particularly adept at reflecting ultrasound away from the sclera and to the inner portion of the lid 130. In another embodiment, the adjunct contains microbubbles which cavitate and can generate miniature shockwaves to dislodge the inspissated material.

Figure 4:
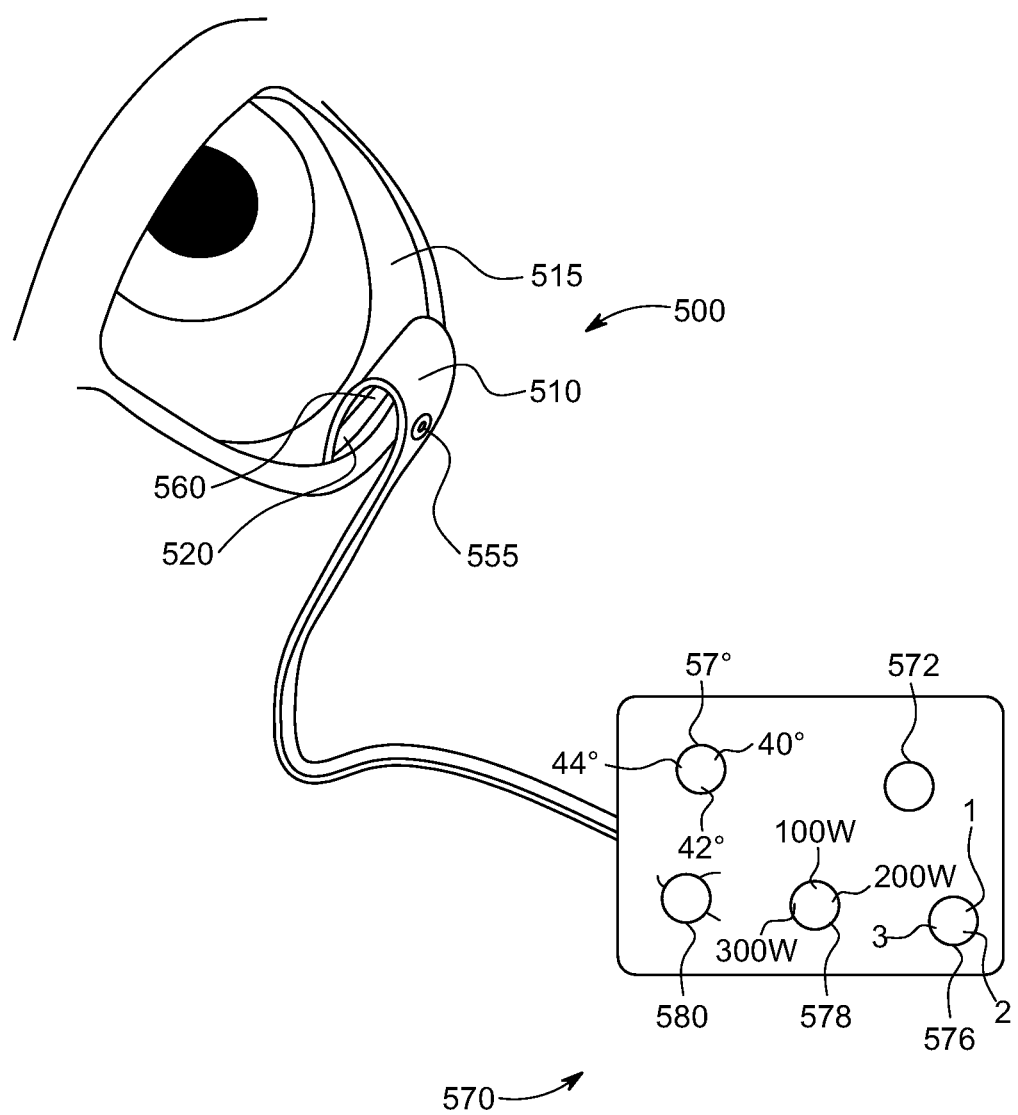
FIG. 4 depicts a retractor inside an eyelid.
Figure 5:
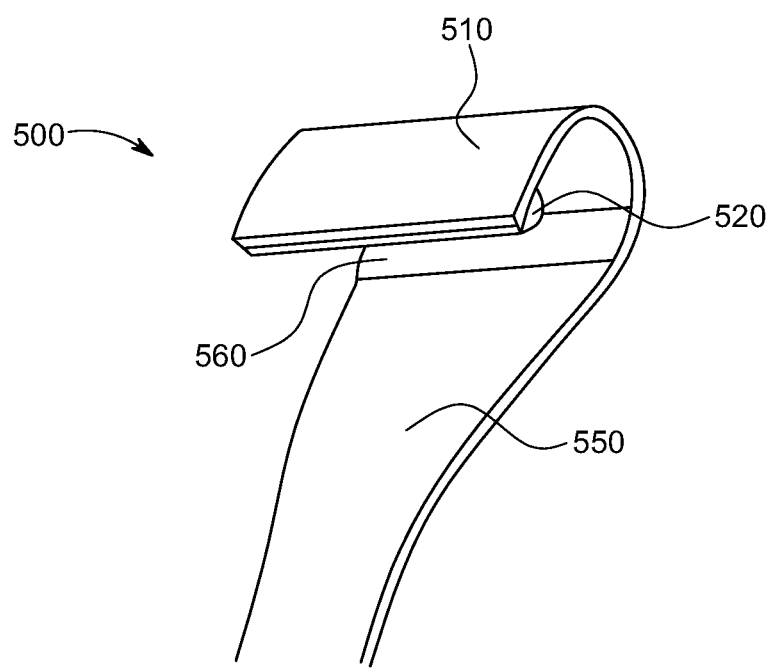
FIG. 5 depicts a retractor with heating elements on it and a control box

In one embodiment, a method is described in which the lower eyelid is retracted inferiorly by a retractor 500 like device (FIGS. 4-5). The retractor 510 serves three or four purposes in this embodiment: the first is that of a retractor to hold the eyelid back to prevent contact with the eyeball; the second can be to act as a backstop to create pressure; the third can be to simultaneously deliver sound, ultrasound, and/or or vibratory waves 560 to the lid; and the fourth can be to act as the adjunct 520 for ultrasound. In this method, the vibration can be delivered through the retracting device 510 and then through the eyelid 515 to the inspissated ducts. In another embodiment, the retractor contains heating and/or vibratory elements thereon 555; for example, piezoelectric devices 560 can be directly attached to one the inner portion of the retractor 510 (FIGS. 4-5). In this embodiment, one or more thermistors 555 can also be added which measure temperature and a control loop can be utilized to maintain the temperature constant between about 40 and 45 degrees C. to both facilitate treatment and maintain a safe zone for safety. In another embodiment, the temperature is maintained between 38 C and 48 C, or in a narrower range between 42 C and 44 C. In some embodiments, element 555 is a compliant material which enables the user of the device to apply manual pressure to the eyelid. For example, element element 555 is a gel, balloon, or other soft and compliant material which is depressed by the operator of the device. The device 500 has a handle 550 with a curve which enables the user to apply the device to the eye comfortably from a distance.

In another embodiment, cooling is employed to change the profile of the inspissated lipids to then facilitate change in phase and removal. For example, the inspissated lipid can be cooled or frozen so that it retracts in the ducts and are easily broken up by pressure, vibration, sound, or ultrasound. A cooling element 555, 560 might be a thermoelectric type cooling element or a peltier effect cooler. Cooling may be combined with sound and ultrasound.

Control box 570 contains software and hardware or software controls to control temperature as well as to allow user facilitated parameter control. For example, the temperature 574 can be adjusted, duty cycle of power on and off 572, maximum power 578, and activation of one or more piezoelectric elements 576 on the retractor 510. Retractor device 510 can incorporate both vibratory, lower frequency, and higher frequency ultrasound with different controls for each to be applied independently or simultaneously. For example, in one embodiment, element 520 delivers ultrasound at between 1 and 30 MHz while a vibratory frequency is applied to the retractor at between 50 and 500 Hz, both mechanical vibrations and ultrasound acting synergistically to dispel oils and unblock inspissated glands. These modes may be combined with electrical stimulation to enhance their effects. Electrical stimulation would preferably be performed with a bipolar electrode on the portion of the device which contacts the inside of the eyelid.

In one preferred embodiment, the device 500 is completely self-contained. That is, the power supply, the ultrasound, the electronics, etc. are all contained within a handheld device and there is no separate or external control box to control the individual elements. A control loop between the ultrasound transducer and the skin or the conjunctiva is utilized to maintain the temperature within a constant range of about 40 C to 46 C.

In one preferred embodiment, a compliant region 555 is added to the retractor such that the compliant material can be depressed against the inner part of the retractor to apply direct pressure to the outside of the lid. The compliant region allows the user of the retractor to simultaneously apply mechanical pressure to the eyelid while heat and vibratory energy are being applied. The compliant regions in one embodiment takes the form of silicone inside a protective membrane. In another embodiment, the compliant region is a balloon fillable with fluid or air. The goal of the compliant portion of the retractor is to enable application of about 5 to 25 psi to the eyelid before, during, or after treatment with the energy. Therefore, in one preferred embodiment, retractor 510 contains ultrasound, mechanical vibration, and mechanical pressure elements to facilitate clearing of the ducts inside an eyelid. The pressure is preferably quantified in preferred embodiments of device 500.

Figure 6:
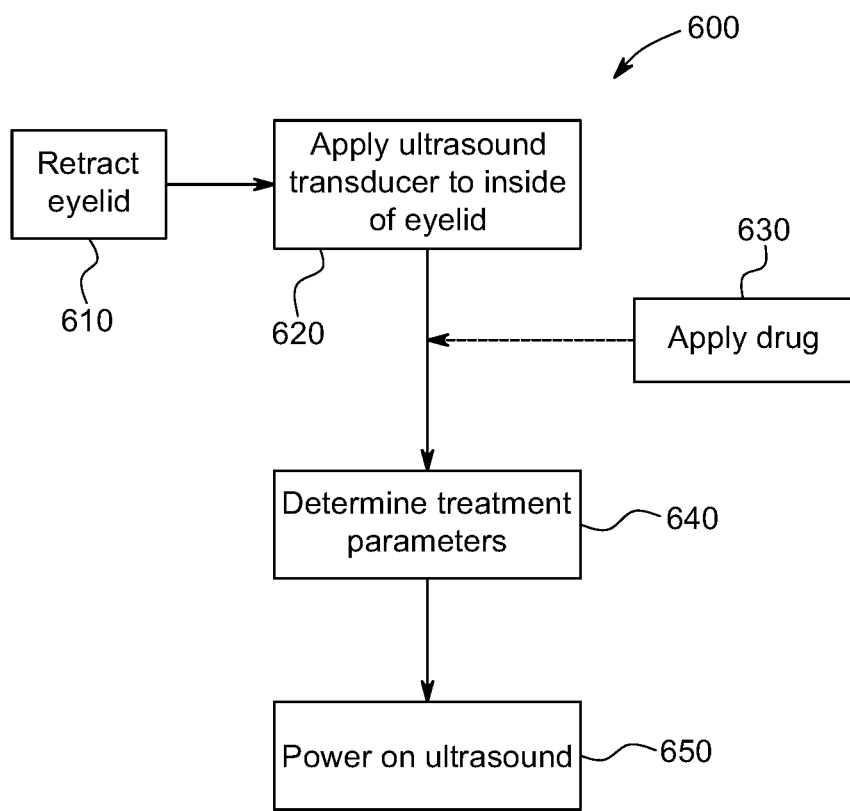
FIG. 6 depicts a method to treat eyelids with ultrasound

FIG. 6 depicts a method 600 to apply ultrasound to the inner portion of the eyelid to clear inspissated ducts on the inner portion of the lid. The lid is first retracted manually 610 or with a provided device 620. Another portion of the retractor is then applied to the outer portion of the eyelid to create pressure against the eyelid. Ultrasound is applied via transducer 620 to the inside of the eyelid with the outer device applying pressure. In this embodiment, the ultrasound is transmitted directly from the transducer to the ducts of the inner eyelid. Optionally, a pharmaceutical or bioactive formulation is applied 630 to enhance the ultrasound effect or vice-versa. Optionally an elastic recoil mechanism is included, both to measure the force or pressure applied to the lids during ultrasound and heat application. Treatment parameters 640 including time, energy level, sound frequency and duty cycle are applied to the transducer. The transducer is then powered on 650 and the energy applied to the eyelid. In another embodiment of the device, the ultrasound transducers are placed on the outside of the of the retractor (e.g. FIGS. 26-27) such that the ultrasound travels through the eyelid from outside to inside. The method of treatment is substantially the same; however, when the transducers contact the outer skin of the lid, the design of the inner portion of the retractor which contacts the inner lid is freed up to maximize comfort for the patient and ease of use ability for the user of the system.

In another embodiment, the eyelid is not retracted and the device 620 is applied over the eyelid to deliver the acoustic energy to the eye, either the inner or the outer eye. The energy travels through the eyelid and into the anterior chamber of the eye and should the power be enough and the attenuation low, to the retina and back of the eye. Other diseases treatable with the retractor with this method include conjunctivitis, bacterial conjunctivitis, glaucoma, macular degeneration, and pterygia. For example, in one embodiment, an ultrasound probe is applied over the eye to deliver vibratory energy to the anterior chamber of the eye to open the trabeculae and allow improved outflow of intraocular fluid to lower pressure. Experimentation predicts that sound waves between 20 and 400 Hz leads to a lower intraocular pressure. Ultrasound at higher frequencies, for example, between 1 MHz and 3 MHz will heat the ciliary bodies and decrease the production of intraocular fluid. Therefore, combining the two energy levels of vibratory energy (e.g. 200 Hz and 3 MHz) will act synergistically to improve intra-ocular pressure.

Figure 7:
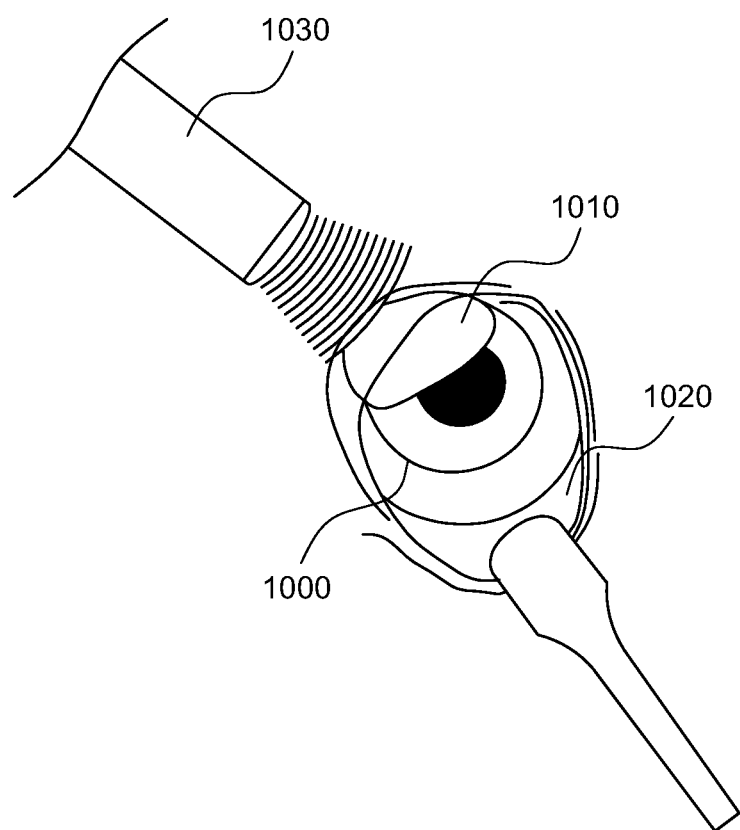
FIG. 7 depicts another embodiment of a transducer and ultrasound adjunct coupled together.

In another embodiment (FIG. 7), an insulator (reflector of ultrasound to protect eye) 1010 is placed inside the eyelid 1020 or on the eye 1000 to protect or facilitate energy delivery via ultrasound 1030 during the treatment. For example, a device adjunct might be a material that is placed on the inner part of the eyelid or on the lid, the device adjunct 1000 possessing the ability to prevent further propagation of ultrasonic waves from the ultrasonic probe 1030 to enhance delivery of heat to the inner portion of the eyelid and protect the conjunctiva and sclera of the eye from the ultrasound and heat.

In one example, the device adjunct 1010 might consist of an outer portion and an inner portion, the two portions separated by a gas. Ultrasound does not travel through air well and therefore the ultrasound will be reflected from the device adjunct 1010, therefore effectively blocking the ultrasound from reaching the eye yet directing heat to the inner portion of the eyelid.

Furthermore, the interface at the point of internal reflections within the adjunct will begin to heat up as the ultrasonic waves are continually reflected from and within the device adjunct. In this method of treatment, the device adjunct is applied to the inner surface of the eyelid and the ultrasound 1030 applied to the outer portion of the eyelid, the waves then transmitting through the eyelid to the Meibomian glands to break up the inspissation in the ducts.

Figure 8:
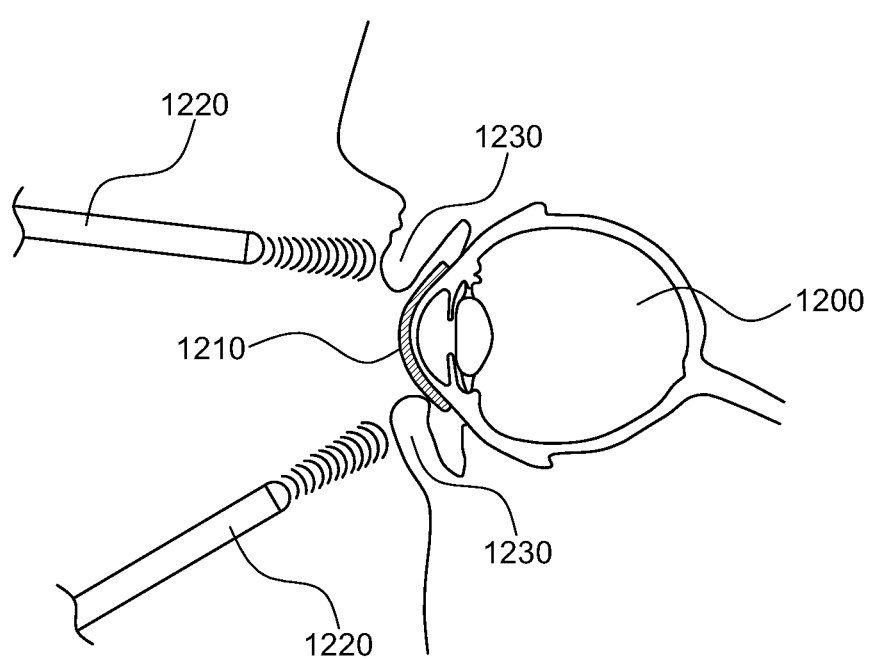
FIG. 8 depicts simultaneous ultrasound probes applying ultrasound to the ocular tissues.

In another embodiment depicted in FIG. 8, ultrasound transducer probes 1220 are shown applying ultrasound to eyelids 1230 with a contact lens 1210 underneath the eyelids 1230. The eye 1200 is protected by the contact lens 1210 as well as additional ultrasound reflective layers on the contact lens as described above and below.

Figure 9:
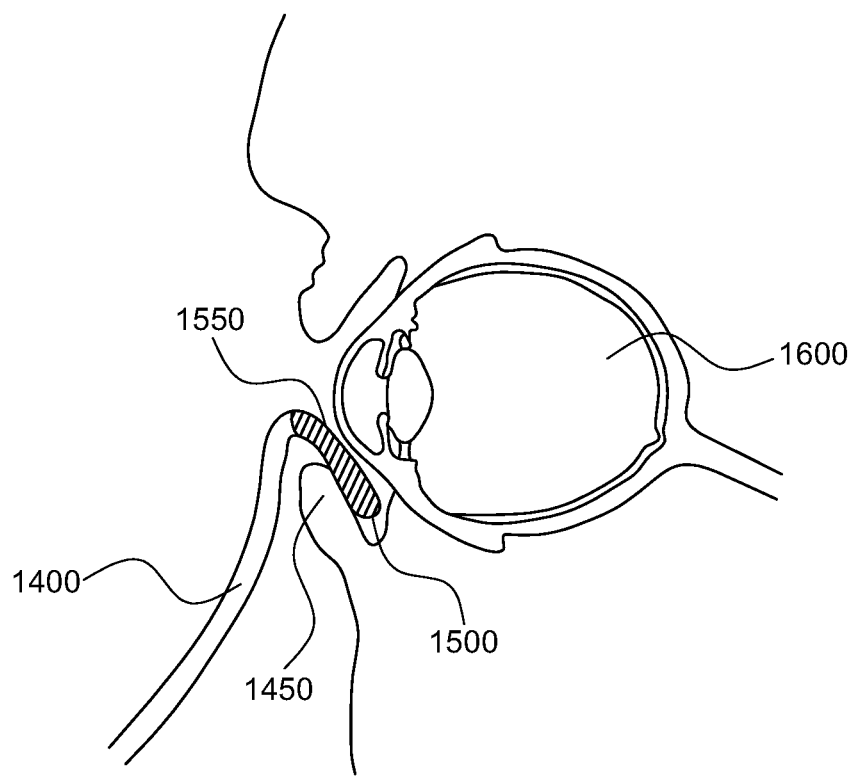
FIG. 9 depicts a retractor for the eyelid with an ultrasound element present on the tip in contact with the lower eyelid.

In another embodiment, depicted in FIG. 9, the ultrasound transducer 1400 and the ultrasound adjunct 1500 are coupled around the eyelid 1450. A reflective material or composite of materials 1550 can be further included in the coupled transducer-ultrasound adjunct. As in previous embodiments, the coupled transducer-adjunct surrounds the eyelid 1450 and protects the eye 1600.

Figure 10:
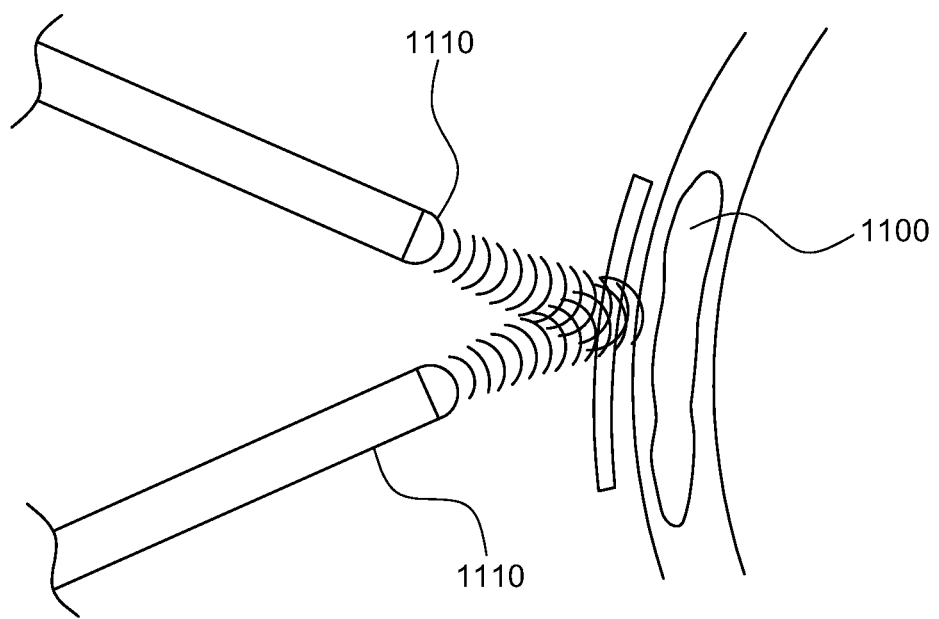
FIG. 10 depicts a contact lens which responds to the therapeutic ultrasound.

In another embodiment, a contact lens 1100 (FIG. 10) is applied to the eye and an ultrasonic energy probe 1110 is applied to the upper and lower eyelids while the eye is closed over the lens 1100. The lens protects the cornea and can be produced such that the ultrasound energy is reflected back to the inner portion of the lid to heat and/or mechanically vibrate the inspissation out of the eyelid.

In another embodiment, ultrasound 1110 is utilized to deliver pharmaceuticals to the eyelids to treat dry eye syndrome. Ultrasound can enhance the delivery of many pharmaceuticals by enhancing their uptake into the cell membranes. In this method, in one embodiment, pharmaceuticals are applied to the inner eyelid of the upper or lower eyelid and subsequently ultrasound is applied to the eyelid to enhance the delivery of the pharmaceutical to the eyelid.

For example, steroids or other anti-inflammatory medications, microbubble formulations, or other bioactive materials can be applied to the inner lid, to a lid retractor, or to the ultrasound adjunct placed inside the lid. The bioactive material might further be incorporated into the ultrasound adjunct to, for example, slowly elute from the adjunct to the inner portion of the lid, the ultrasound further augmenting its ability to interact with the glands within the eyelid. In another embodiment, an anti-inflammatory is applied to the lid or surface of the eye and ultrasound utilized to enhance the uptake of the anti-inflammatory into the epithelial layers on the ocular surface.

In some embodiments, ultrasound is utilized to make alterations in the tissues of the eye. Tissues of the eye can include the eyelid, the eyebrow, the eyelashes, glands (for example lacrimal glands within and around the eye) including Meibomian and lacrimal glands, any part of the sclera, the iris, the trabecular meshwork, the ciliary processes, Schlemm's canal, the retina and its different layer of cells, the choroid, the vitreous, the lens, the lens capsule, the zonules, the aqueous humor of the anterior chamber, the optic nerve, the macula, the fovea, nerves which stimulate or inhibit processes in the eye (e.g. sphenopalatine ganglia, lacrimal nerve, trigeminal ganglia, facial nerve, ethmoidal nerves) and the retinal blood vessels including the retinal vein and artery and any branches.

Typical ultrasound (e.g. diagnostic imaging) is low intensity and utilizes reflections from tissues for imaging. If the power is increased, then focused or unfocused therapeutic applications arise. For example, it is known that high intensity focused ultrasound can produce highly focal heating and lower intensity focal ultrasound can induce tissue regeneration. Low intensity and/or low frequency (e.g. 20 kHz to 500 kHz) focused ultrasound can also be used for drug delivery by opening up cell membranes and allowing molecules to be transported into the cells and tissues. Low intensity ultrasound applied to the ocular tissues can result in a number of beneficial clinical results including healing of tissues such as the retina and drug and gene delivery to any structure of the eye.

Figure 11:
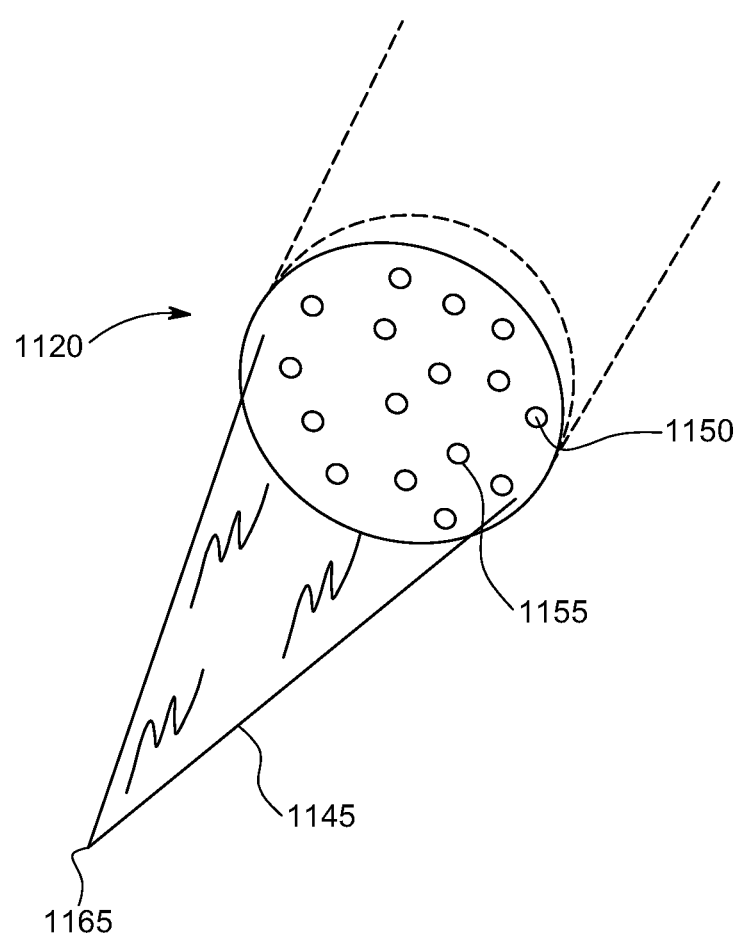
FIG. 11 depicts a multi-element array at the end of an ultrasound probe.

Ultrasound waves are created by resonating elements which produce pressure waves at frequencies determined by the properties of the elements. In some applications, a single element is utilized and a curved shape of this element naturally focuses the ultrasound at a focal point. In another design 1120, for example FIG. 11, multiple elements 1150, 1155 may be linked together, each with a phase control which allows for focusing 1145 at a point distal 1165 from the array. Depending on the phase control, the focus point can be moved (electronic phasing). In some embodiments, the focused ultrasound is coupled to an imaging device which simultaneously images structures in the eye and transmits coordinates to the therapeutic ultrasound device to direct the treatment. In some embodiments, the ultrasound waves remain unfocused or softly focused.

Referring to FIG. 8, a pair of ultrasound transducers 1220 are depicted in two different physical positions on the eye. Typically, the ultrasound would be applied with the eye closed but in some embodiments, the ultrasound is applied with the eye open with the ultrasound probe contacting the conjunctiva. Each of the transducers is directed into the eye 1200 from different angles. In this embodiment, a pair of transducers is depicted but the system may include a single transducer or more than two transducers depending on the application.

In some embodiments, it is preferred that the transducers are angled to avoid the lens such that minimal or no ultrasound energy reaches the lens because the lens can be very sensitive to heating and mechanical forces. In this embodiment, the ultrasound beams overlap at a position posterior to the lens. The exact position depends on the energy level, frequency, and the specific application of the ultrasound. Another reason that in some embodiments the transducers are offset from the lens is that the central visual pathway of the eye may be utilized for imaging of the intra-ocular structures such as, for example, if OCT were couple to ultrasound or optical ophthalmic imaging (e.g. using a slit lamp).

Each of the transducers 1220 can create frequencies of ultrasound from 10 kHz to 2 MHz depending on the application. In some embodiments, "ultrasound" isn't used and "sound" or "vibration" is used with frequencies ranging from 10 Hz to 10 kHz. In this embodiment, an amplitude and frequency is specified. Each of the transducers can have a membrane or other acoustic coupling interface for the sclera or skin of the eye. The membrane 115 can be composed of a hydrogel or similar material so it doesn't scratch or injure the scleral surface. In the embodiment where the ultrasound applicator is applied to the eyelid, then a membrane is not required and typical skin methods and materials for the ultrasound probe interface can be utilized. In some embodiments, the ultrasound transducers are configured into a patch or otherwise a device which can be attached to the skin of a patient.

In one embodiment, the ultrasound transducers 1220 are placed on the surface of the eye and coupled to one another to deliver focused ultrasound to the retina. By coupling the ultrasound transducers together, each of them can be made smaller in size. This arrangement is equivalent to having multiple elements yet the multiple elements are separate in space so as to avoid sensitive structures such as the lens. The transducers 1220 can be coupled using optical coupling or electromagnetic coupling or they can be coupled to each other mechanically or physically in space.

In some embodiments, a single ultrasound transducer can be used either directed at an angle to the lens (pars plana) or directed straight through the cornea and lens to the posterior of the eye. In this embodiment, the objective may be to softly focus the ultrasound or not focus the ultrasound at all so that the retina or vitreous is exposed to a broad ultrasound field.

In some embodiments when a single transducer is used, the ultrasound is either not focused or is focused softly or not focused at all. In an embodiment where the ultrasound is softly focused or not focused, the focused ultrasound can have a maximum where a −6 dB radius around the center is within 2 mm, 4 mm, 6 mm, or 1 cm. If unfocused, the ultrasound focus extends to infinity and therapy occurs via a broad ultrasound field.

In some embodiments, ultrasound is applied to the posterior segment of the eye to loosen or break up fibrotic or avascular zones or lesions to promote drug delivery, healing, or both. Drug delivery to these lesions might include steroids, anti-angiogenic factors, or growth stimulants, and the like. Gene producing vectors may also be introduced in the posterior of the eye this way. The ultrasound to the posterior segment may be focused, softly focused, or unfocused depending on the desired intensity and application and/or specificity of location. In some embodiments, the ultrasound is targeted at drusen, calcified lesions in the retina, which can cause dry AMD or wet AMD in time.

"Floaters" are particulate matter in the vitreous portion in the posterior chamber of the eye; they are typically composed of blood clots, congealed collagen, or other debris that break loose and cause visual distortions. In some embodiments, unfocused ultrasound can be utilized to break up this debris and improve vision. In this application, the ultrasound probe is configured to apply a continuous or pulsed wave of unfocused ultrasound at a frequency (e.g. in the 10 Hz to 800 kHz range) or the (100 kHz to 1 MHz) range so as to take advantage of the interface between the vitreous and the floater. In some embodiments, the vitreous is a gel and in this case, the viscous gel can be broken up or liquefied to allow more free flow in the posterior vitreous.

Clots can form in retinal veins or arteries just as they can in any blood vessel in the body. In some embodiments, focused or unfocused ultrasound is used to break up these clots alone or in combination with thrombolytic agents or by itself without thrombolytic agents. In some embodiments, ultrasound sensitive microbubbles are delivered to the patient intravenously and to the eye via circulation; ultrasound is applied to the retina in either a focused or an unfocused manner toward the retinal occlusion. Short bursts are delivered in some embodiments and longer pulses are applied in other embodiments. In some embodiments, 1 MHz ultrasound is utilized and in other embodiments, a range up to 30 MHz is utilized depending on the desired penetration through the eye.

In another embodiment, a partial posterior vitreous detachment can be completed using focused or unfocused ultrasound. The vitreous of the posterior cavity is typically tacked down to the retina. However, with age, the vitreous begins to separate. When it is only partially detached, it creates traction on the macula or other portion of the retina and there is both a need and a procedure to release the membrane from the retina. However, these are dangerous procedures because of their invasiveness. Ultrasound can be non-invasively delivered. Macular holes or retina detachments can then form. Therefore, the vitreous should be either completely detached or completely attached to the retina. Currently available treatments include treatment with an enzyme which chemically disrupts the partial detachment to create a full detachment and relieve the stress on the retina or a vitrectomy (removal of the posterior vitreous and replacement with a similar liquid). The use of a non-invasive technology to relieve the distortion is likely preferable and may be more effective than the standard treatment modality of either liquefaction or vitrectomy. Such non-invasive technology is also amenable to repeat treatments as well. In one embodiment, unfocused ultrasound is applied to the eye through the eyelid or through conduction via the bony structures of the face.

Figure 12:
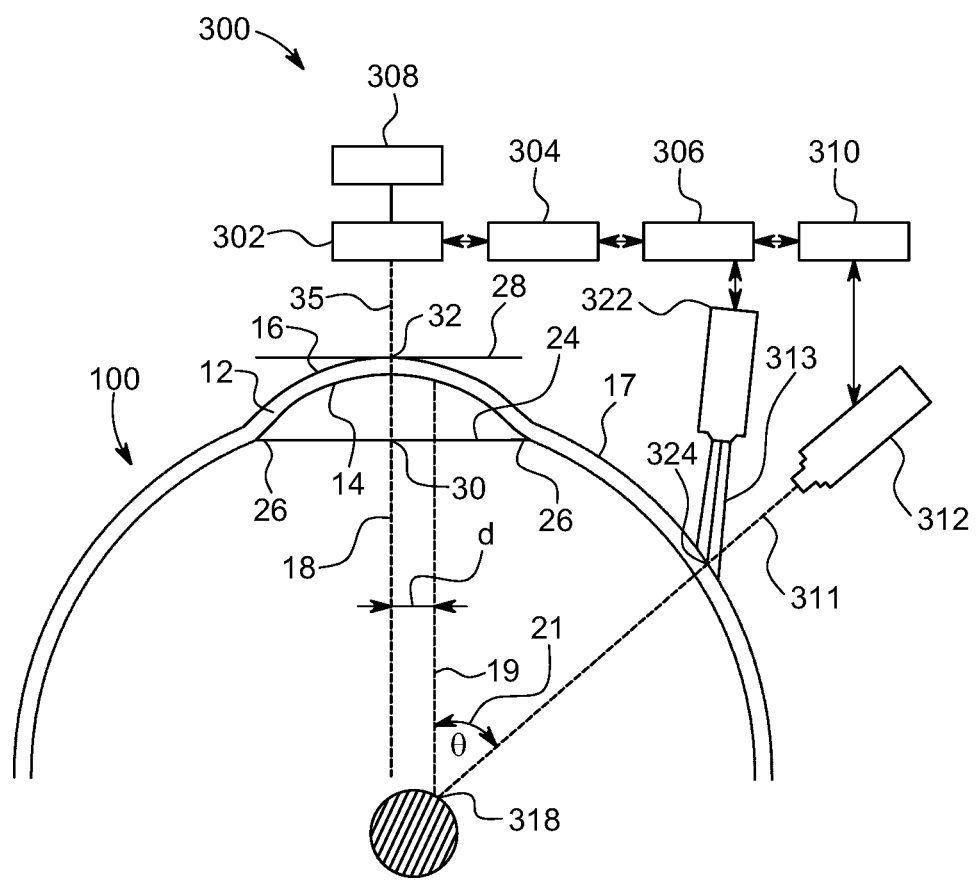
FIG. 12 depicts a set up of ultrasound transducer to deliver focused ultrasound energy to the back of the eye.

FIG. 12 depicts a system 300 which generates ultrasound to deep structures within the eye 100. Ultrasound transducers 312, 322 are configured to deliver ultrasound energy 18, 35, 311, 313 to structures of the eye, e.g., the sclera 17, the surfaces of the cornea 14, 16, the iris 24, and an angle of the eye 26. One or more power amplifiers 306, 310, 302 drive the ultrasound transducers to deliver the calculated therapeutic energy to the eye. In some embodiments, the ultrasound transducer 322 may serve as an imaging device which directs the ultrasound from other ultrasound elements on the same transducer or elements on another transducer 312. CPU 308 directs the therapy. Processor 304 integrates signals from various components to create a treatment plan for an eye. Treatment region 318 is shown on the retina but can in fact be anywhere in the eye; for example, the treatment can be applied to the optic nerve, the sclera, the iris, the pupil, the lens, the trabecular meshwork, the cornea, lens capsule, the conjunctiva, the eyelids, Meibomian glands, eyelashes, orbital bones, blood vessel such as the retinal artery and veins, etc. The treatment region 318 can result from focused ultrasound being applied from different directions into the eye or can result from a single propagating ultrasound wave. The treatment region is defined by perpendicular line 32 which traverses the front of the eye as and its perpendicular line 28 which can be used to direct the external therapy e.g. through reflections.

Treatment line 30 is a line directly down the center of the eye, or just off the center 19 of the eye and can serve as a reference point for the treatment; in some embodiments, the ultrasound is delivered along this center line of the eye to the retina or along a line parallel to it; d represents an offset from the center line. In some embodiments, angle theta 21 is used to guide the position and orientation of therapeutic transducers 312, 322. Angle theta represents an angle to the center line of the eye. If the center line of the eye is known and the distance from the front of the eye to back is known, then the angle determines the position along the sclera to deliver the ultrasound energy to the retina region.

In another embodiment, ultrasound is applied to an eye simultaneously or in sequence with ionizing radiation therapy to enhance the treatment of the retina with the ionizing radiation.

In another embodiment, a tracking system for the eye is utilized for the treatment with the ultrasound. In the tracking system, a fiducial is not utilized by the system. A three dimensional image of the eyeball is utilized, the image utilized to place the entire eye into a three dimensional coordinate reference frame. In another embodiment, a two dimensional B-mode image of the retina is utilized for tracking. For example, speckles on the retina ultrasound image can be used to track movement of the retina and update a location on the retina for treatment with therapeutic ultrasound.

In another embodiment, micropores are created using focused ultrasound. Micropores result from specific energy intensity being applied to the retina. Research suggests that the blood retina and the retina vitreous barrier can be transiently interrupted using focused ultrasound. This interruption can be utilized to allow for enhanced drug delivery. In another embodiment, the stimulating effect of ultrasound is utilized to enhance delivery of pharmaceuticals or gene delivery vectors. In one example, when a sub-retinal injection of a gene delivery emulsion is delivered to the retina, ultrasound is utilized to enhance the delivery after the injection.

In another embodiment, bubbles or microspheres are used to open pores in the retina for drug and gene delivery. The microbubbles create a small cavitation region which can transiently open cells to enhance delivery of bioactive agents to the region.

In another embodiment of the system to deliver ultrasound to the structures of the eye, a treatment device in the form of an eye mask is utilized which covers both eyes and contains ultrasound transducers pointed toward the retina of the patient. The mask has a series of ultrasound transducers directed to the eye. The transducers may be arranged around the mask in a ring or on the edges of the mask to deliver the ultrasound energy at an angle 21 to the lens. The mask may contain a single transducer for each eye or multiple transducers per eye. The size of each transducers might be under a millimeter (mm) or greater than one mm and up to one cm.

The electronic control circuit which turns the transducers on and off might alternate power to one or more of the transducers to enable high power to be delivered to each of the transducers in an alternating manner so as to maximize the power leaving each transducer at a given time.

In another embodiment, ultrasound is used to stimulate tear production by a lacrimal gland in the eye. For example, ultrasound waves 1030 are applied to the conjunctival region above the eyelid (FIG. 7) to stimulate the lacrimal gland to secrete tears. An ultrasound probe 1030 is applied to the eyelid through which ultrasound is applied to the lacrimal gland. Unfocused ultrasound is utilized to stimulate the lacrimal gland through the eyelid. The energy level of the ultrasound at the point the waves interact with the lacrimal gland is 1 mW/cm2 to 10 W/cm2 at sonic frequencies 50 kHz to 30 MHz. In some instances, the ultrasound is focused and in others, the ultrasound is unfocused. The probe is in the form of a wand which is held on the eyelid in the region of the lacrimal gland. When ultrasound is applied the stimulating effect of the ultrasound stimulates the tear duct to release tears. In some embodiments, sound waves are used in place of ultrasound. Vibrating sound waves at (for example 50-300 Hz) can penetrate bone and stimulate normal tissue by activating nerves.

It has also been determined that lower frequency (not sound) vibrations can stimulate tear production. For example, vibration at a frequency of 100 Hz or 300 Hz and up to 1 KHz can stimulate the anterior ethmoidal nerve, the sphenopalatine ganglia, the lacrimal nerve, the facial nerves and more internal nerves and ganglia otherwise accessible only by invasive methods. For example, the lacrimal nerves or nerves proximal to the lacrimal nerve such as the sphenopalatine ganglia, the ethmoidal nerves, the vidian nerve, and the infraorbital nerves can be stimulated directly through the application of vibratory energy through the skin and bones. The energy travels through the skin and meets the bone, at which point the bone resonates to produce stimulation of the nerves. Therefore, in one embodiment, a probe 1030 is applied to the upper eyelid and the probe delivers vibratory energy to the lacrimal gland, inducing immediate tear production.

In another embodiment, ultrasound transducers are applied to bony regions of the face and in a preferred embodiment on the orbit region to transmit ultrasound to the posterior or anterior of the eye. The ultrasound is transmitted across the bones to the retina region by conduction through the bones. Therefore, in this method, vibration is utilized to stimulate the retina via vibration of the bony structures of the orbit and resultant resonant transmission to the retina.

In another embodiment, ultrasound is applied to the skin surface of the face to facilitate exit of infection from the Eustachian tube in otitis media. In this example, the resonance of the bone agitates the infected fluid inside the Eustachian tube to assist in its expulsion. In another embodiment, the device is utilized to maintain uniform pressure in the eustachian tube, for example, during aircraft travel, during SCUBA diving, or in the case of sinusitis or a cold.

Figure 13:
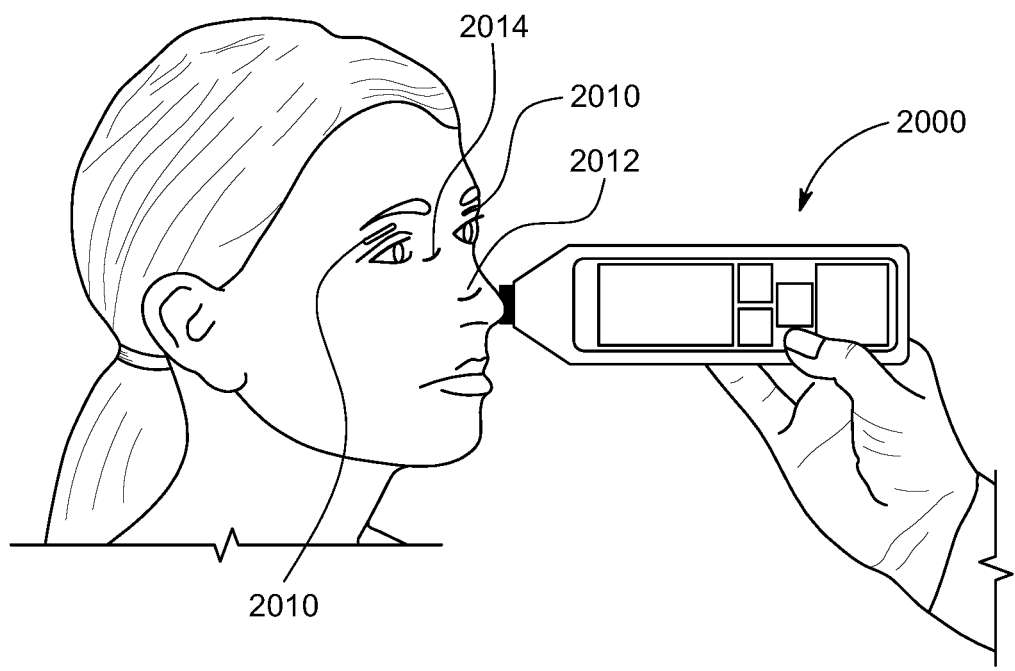
FIG. 13 depicts a device to deliver vibrational energy to the nasal turbinates and nerves inside the nasal cavity via contact through the skin and bony structures of the nose.

FIG. 13 depicts an embodiment of a device to stimulate the lacrimal gland or other nerves or ganglia transcutaneously through the skin to the nerves and ganglia. Regions 2012, 2014, and 2010 have been shown experimentally to produce the greatest amount of nerve stimulation by way of vibration of the facial bones which in turn stimulate the nerves such as sphenopalatine ganglia, lacrimal nerve, external nasal nerve, infratrochlear nerve, supratraochlear nerve, infraorbital nerve, supraorbital nerve etc. For example, region 2012, when exposed to direct skin vibration at approximately 100 Hz-300 Hz vibration produces copious bilateral tear formation bilaterally when just a single side is stimulated. In some embodiments, vibrations from about 50 Hz to about 500 Hz are utilized to stimulate the bones of the face to in turn transmit vibrations to the nerves which stimulate tear production. The treatment works best at the resonant frequency of the bone so that the vibration of the bone is maximal and affects the nerve maximally due the greatest amount of mechanical movement of the nerve and subsequent stimulation. The resonant frequency of the bone is to some extent individualized per patient. This frequency has been experimentally determined and subsequently proven to be in the range of about 100-300 Hz.

Region 2014 (FIG. 13) includes the bottom eyelid (inner and outer eyelid), the medial canthus of the eye along the nasolacrimal duct. External stimulation along these regions in some embodiments stimulates the nerves through bony resonance and in some embodiments, stimulates the glands in the lower eyelid region directly.

Figure 14:
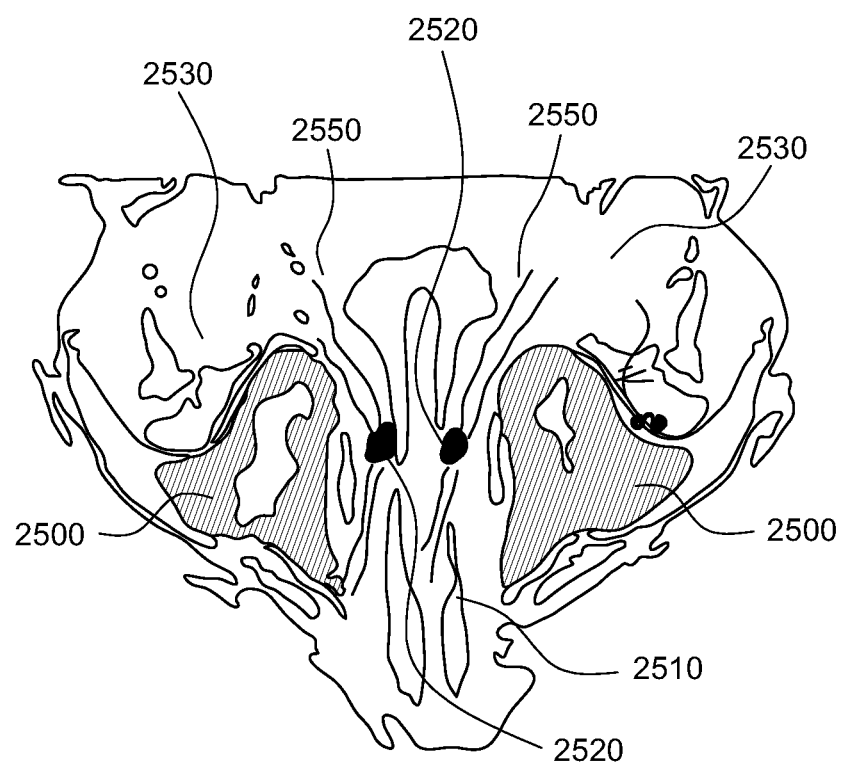
FIG. 14 depicts a coronal section through the sinuses

FIG. 14 depicts neural pathways involved in the transduction of vibration from the skin to the lacrimal gland when vibrations are applied through the preferred external location 2012 in FIG. 13. Ganglia 2520 projects nerves to the lacrimal nerve 2550 which courses to the orbit to stimulate the main lacrimal gland in the superior portion of the orbit. Bone 2530 transmits vibrations to the lacrimal nerve 2550 and around the maxillary sinus 2500 via the sphenopalatine ganglia. The sphenopalatine ganglia 2520 is covered by mucosa and sits between the turbinates which are accessible transnasally through the external nasal passageways 2510. The external nasal nerve is a terminal branch of the ophthalmic branch of the trigeminal nerve and is directly stimulated with vibration as it is compressed against its exit from underneath the nasal bone at the junction of the nasal bone and the anterior lateral nasal cartilage. In another embodiment, an ultrasound or sound producing probe is inserted through the external nasal passageways 2510 and applied to the mucosa in proximity to the sphenopalatine ganglia 2520 to stimulate tear production through direct stimulation or via the nasolacrimal reflex. In another embodiment, a vibratory probe with vibration at approximately 100-300 Hz is inserted into the nasal passage to directly stimulate the sphenopalatine ganglia and/or the interior anterior ethmoidal nerves on the interior of the nasal passage. In another embodiment, electrical stimulation of the external nasal nerve accomplishes tearing by activating the lacrimal nucleus in the pons and subsequently pregangliotic fibers within the maxillary nerve which synapse in the sphenopalatine ganglia and then stimulate the lacrimal nerve to produce tears.

In one embodiment, a method to stimulate neural pathways through the application of sound or ultrasound energy transcutaneously is described. An applicator is disposed to the face of the patient, the applicator comprising one or more vibratory elements capable of generating vibrations from about 50 Hz to about 50 kHz. The vibration is applied to a region close to a nerve under the skin or to a region with a bony prominence which communicates via bone structure with a nerve region located close to the skin. For example, an applicator 2000 disposed to the region 2010, 2012 (FIG. 13) or 2014 (FIGS. 13, 15) will transmit the vibratory energy to the lacrimal glands and produce tears. The resonant frequency is different for each person as is the exact location and direction of the vibration. In one embodiment, the individual resonant frequency is determined and the device adjusted to this frequency for each person. An interface between the device and the patient's skin is similarly adjustable so that the vibrations are transmitted to the nerves in the head and neck region to be stimulated. For example, the parasympathetic nerve which innervates the lacrimal gland travels within the maxillary bone and the through the sphenopalatine ganglia is located close to the maxillary bone in the sphenopalatine fossa. At a resonant frequency of the maxillary bone, it has been discovered that the ganglia can be stimulated and tears produced. The resonant frequency is achieved through a combination of material, vibration frequency, and amplitude. For example, a material with a durometer between Shore A40 and Shore A60 vibrating over a surface area of between 5 mm2 and 20 mm2 with an amplitude of about 0.5 to 5 mm and frequency of between 50 Hz and 400 Hz results in copious tears. With a directionality upward and at a location approximately along the nasal bone where it meets the cartilage, tears can be produced without discomfort or sneezing or other nasal symptoms. The total force applied over the surface area in some embodiments is about 1N (Newton). In other embodiments, the total force is from about 0.5N to bout 2N. In other embodiments, the force is about 0.25N to about 4N.

Figure 30:
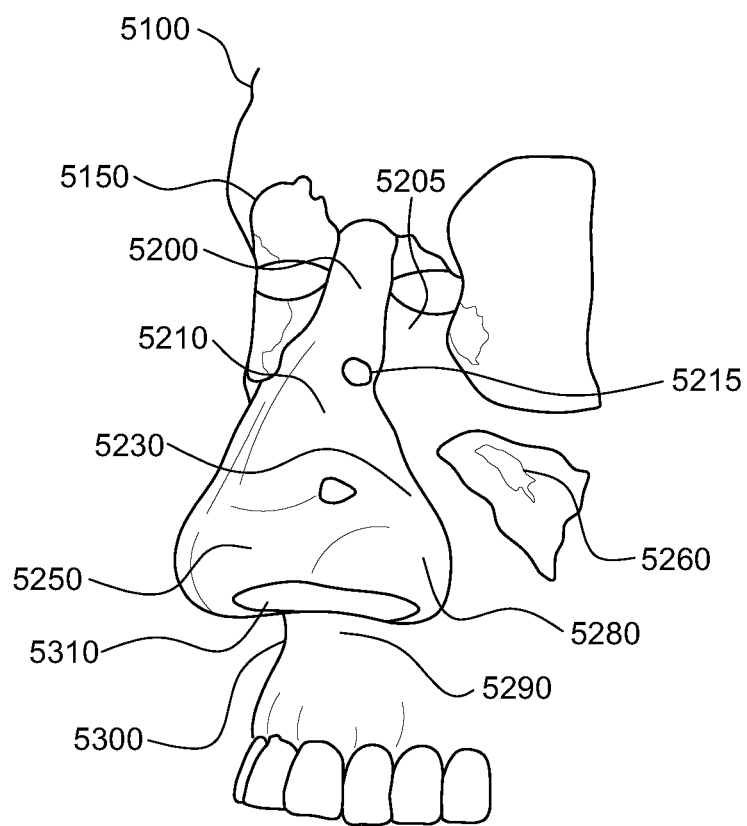
FIG. 30 depicts the boney and soft tissue structures in and around the nose.
Figure 31:
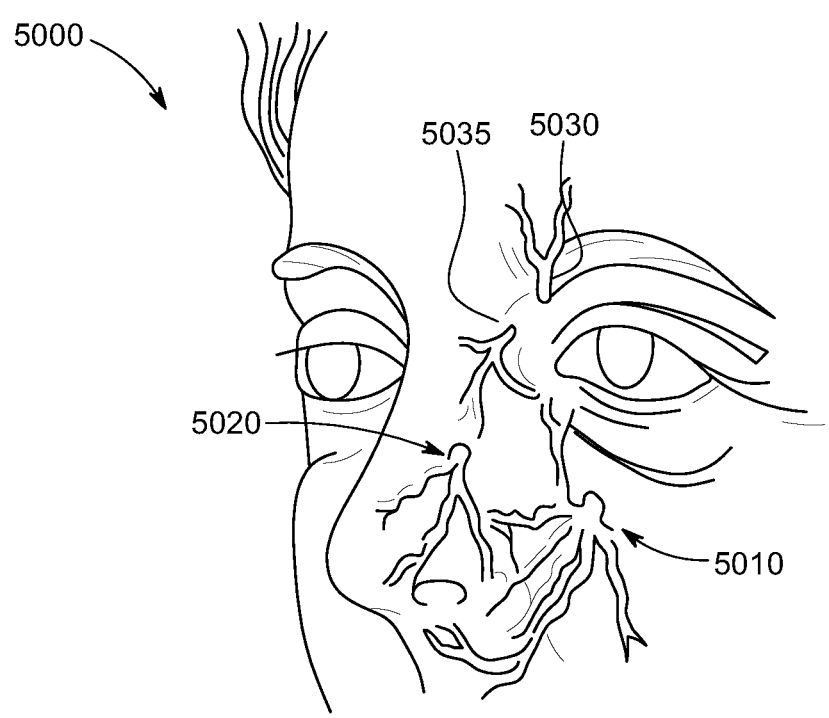
FIG. 31 depicts the nerve anatomy in and around the nose.

FIG. 30 depicts the bony anatomy of the face. FIG. 31 depicts the nervous anatomy of the face. In FIG. 31, at the point where the upper lateral cartilage meets the nasal bone, the external branch of the anterior ethmoidal nerve penetrates the nasal bone is depicted. This location is where the lateral process of the septal nasal cartilage meets the nasal bone (FIG. 30) and 2012 in FIG. 16. This is the location, located on the skin, which has been discovered through experimentation to produce tears when mechanical vibration is applied at a frequency of 50-300 with a vibration amplitude of approximately 0.5 mm to 1.5 mm and/or force of about 0.5 to 1.5N.

Furthermore, it has been discovered that direct stimulation of the infratrochlear and infraorbital nerves with mechanical vibration also induces lacrimation.

Mechanical vibration can also stimulate lacrimation by direct contact with the mucosal surfaces inside the nose.

FIG. 31 depicts the neural anatomy of this region underneath the skin. The anterior ethmoidal nerve, a direct continuation of the nasociliary nerve, splits into two branches to supply the nasal mucosa, medial and lateral, as it enters the nasal cavity where is supplies the nasal mucosa. The nasociliary nerve continues to the caudal region of the nasal bone and appears 6.5 mm to 8.5 mm from the midline as the external nasal nerve (Prendergast in Shaiiman, M A and Giuseppe A D Advanced Aesthetic Rhinoplasty. Springer-Verlag 2013). The infraorbital nerve 5010 exits the bone and travels into the skin approximately 1-2 cm below the lower eyelid. It is the external nasal nerve which has been determined to induce tearing when vibrations at 50-300 Hz are applied. Electrical stimulation (bipolar or monopolar) of the external nasal nerve in this region also can be utilized to induce lacrimation.

A well described pathway for lacrimation is called the nasolacrimal reflex in which stimulation of afferent fibers of the anterior ethmoidal nerve (accessible inside the nose) travel through the ophthalmic nerve to the salivary nucleus in the brain stem (Dart, D A Prog Retin Eye Disease 2009; May 28(3): 155-177), then parasympathetic nerve signals travel via the maxillary branch of the trigeminal synapse in the sphenopalatine ganglia to innervate the lacrimal nerve and stimulate the lacrimal glands. Parasympathetic fibers generally stimulate the lacrimal glands and also partially innervate the Meibomian glands.

In addition to the specific descriptions set forth herein, it has been discovered through extensive experimentation that stimulation of the external nasal nerve achieves lacrimation. As described above, the external nasal nerve 5020 exits deep to the layers of the skin through an orifice 5270 at the junction of the nasal cartilage 5240 and nasal bone 5210. It is not accessible by electrical stimulation. As described herein, certain vibrational parameters result in stimulation of lacrimation similar to the nasolacrimal reflex.

Han et. al (Plast Reconstr Surg 114: 1055, 2004) characterized the anatomy of the external nasal nerve in cadaver specimens. The external nasal nerve is a continuation of the nasociliary nerve which originates from the ophthalmic branch of the trigeminal nerve. Prior to its exit from the inner portion of the nose to the external portion of the nose, it gives off two branches to the inner portion of the nose. The external nasal branch is the terminal nerve of the nasociliary nerve. After exiting the inner portion of the nose between the nasal bone and the upper lateral cartilage (through a notch in the nasal bone), the external nasal nerve dips into the fibrofatty tissue to ultimately branch and supply the skin and fatty tissues of the distal nose. The exit was consistently 6.5-8.5 mm lateral to the nasal midline independent of the width of nose. There were there branching patterns identified. The first was a single nerve exiting the nasal bone. The second pattern was splitting of the nerve upon exit from the nasal bone and the third pattern was splitting of the nerve distal to the exit from the nasal bone close to the cartilage of the distal region of the nose. The nerve size in this study was consistently 0.3 mm to 0.4 mm diameter.

Therefore, in one embodiment, a device is placed approximately 6.5 to 8.5 mm lateral to the nasal midline at the region where the upper lateral cartilage meets the nasal bone. The device is placed unilaterally or bilaterally or unilaterally and then sequentially on the contralateral side for bilateral treatment. The device applies a force over an are of 1-2 mm$^2$ on the nose at frequency of 100-300 Hz. In some embodiments, approximately 0.5 to about 2.0 Newtons (N) of force is applied to the external nasal nerve as it leaves the nasal bone. In other embodiments, a force of approximately 2 to about 5 N is applied to the nose to activate the external nasal nerve.

Figure 15:
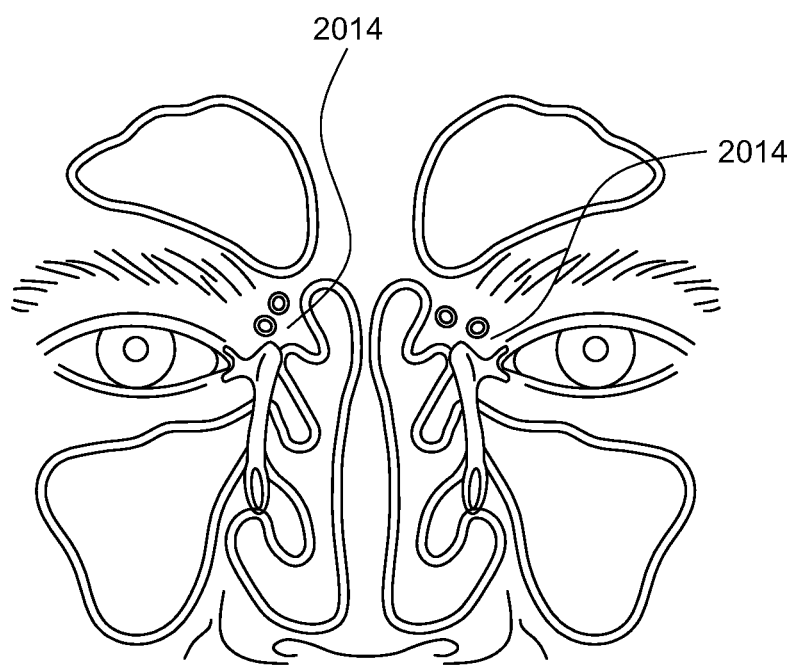
FIG. 15 depicts a coronal section through the face with the tear duct anatomy outlined.

In another embodiment in FIG. 15, the nasolacrimal duct is the target. It has been found in clinical work that stimulation of this duct internally along its length leads to stimulation of tear production. The mechanism is thought to be direct stimulation of the nasolacrimal reflex. In this invention, it has been further discovered that vibration at 100-500 Hz externally through the skin in the region of the bone through which the duct travels (e.g. nasal bone) also stimulates this reflex. Similar to the external nasal nerve, electrical stimulation has been found to be ineffective in the stimulation of the reflex through this anatomy The effector interface with the face of the patient is a very important component of the energy transmission to promote safety and tolerability of the procedure. Through experimentation, the optimal durometer is somewhere between Shore 40 A (pencil eraser) and Shore 80 A (leather). Shore 60 A is about a car tire tread and Shore 70 A is a running shoe sole. With an interface which is too hard, the skin is abraded and with an interface which is too soft, the nerve is not effectively stimulated.

It has been determined that unfocused vibration at 50 Hz to about 300 Hz leads to general activation of the sphenopalatine ganglion, lacrimal nerve, external nasal nerve, infratrochlear nerve, infraorbital nerve, supraorbital nerve, or internal nasal nerve leading to inhibition of rhinitis like symptoms by overstimulation and/or relief from nasal congestion, migraines, narcolepsy, dry mouth, dry eye, and elevated intra-ocular pressure via neuromodulation. Focused, or directed vibration, be it sound in which the vibrating waves are directed toward the skin and bone by way of positioning the probe toward the nasopalatine ganglia, external nasal nerves, or eyelids, or lacrimal nerves have been determined to be more effective in eliciting specific pathways such as lacrimation.

Figure 16:
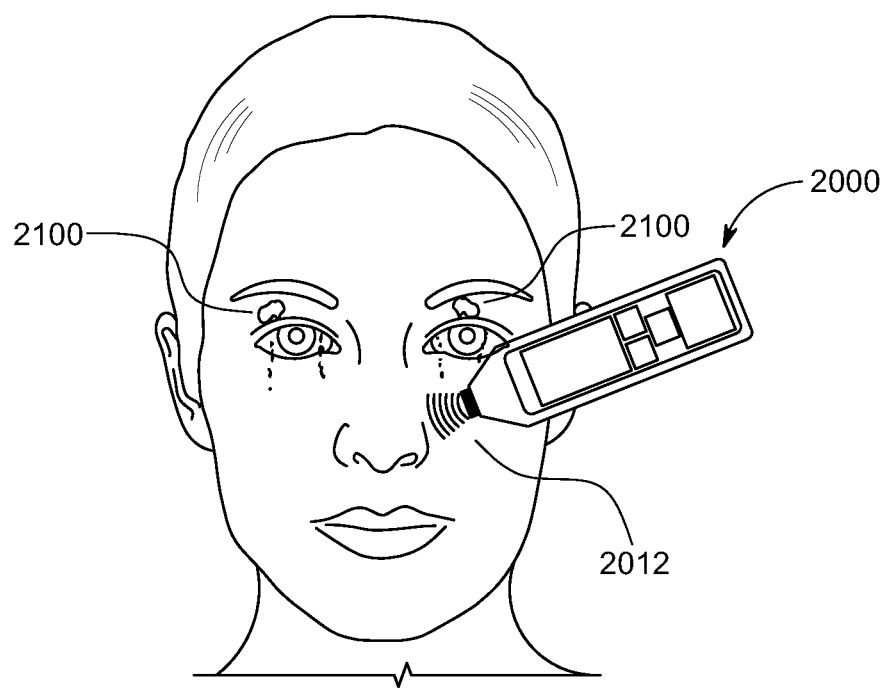
FIG. 16 illustrates an ultrasound transducer adapted to apply ultrasound energy to the tissues of the nasal cavity.

FIG. 16 depicts a device usable to activate the lacrimation pathway by applying vibration to the side of the nose and/or lacrimal pathway to activate the external nasal nerve as it exits the nasal bone onto the skin of the nose. Vibratory energy at 100-300 Hz with 1 mm excursion and 1-4N of force stimulates the external nasal nerve when then energy is applied to the region with a sufficiently rigid biocompatible material.

In another preferred embodiment, the vibration is applied directly to the conjunctival region of the eyelid to stimulate tears directly by stimulating the accessory lacrimal glands in the lower lid and the small muscles that surround each of the Meibomian glands.

In one embodiment, the end effector of device 2000 is applied directly to the lacrimal gland 2100 or to the mucosa of the inner eyelid. Device 2000 is configured in one embodiment to run along the inner eyelid while the eyelid is being retracted to create tears, stimulate Meibomian glands, etc. In one embodiment, device 2000 is depressed against the skin of the nose in the region where the nasal cartilage meets the nasal bone (aka the nasal ala) 2012 where the cartilage and nasal bone meet along the side of the nose of the patient at the region where the external nasal nerve exits the nasal bone.

Therefore, in one embodiment, a vibratory device is applied to the skin/mucosa of the inner eyelid, applying an end effector moving at about 50-300 Hz with the end effector moving approximately 250 microns to 2 mm in excursion with 0.5 to 2N of force, the end effector having a biocompatible material with durometer between about 60 A and 100 A and a tip which applies the force to the skin over an area of about 1 mm$^2$ to 5 mm$^2$. Pulsed frequencies (on-off) can enhance the effect. For example, the vibration can be applied with a 50% duty cycle or a 25% duty cycle with a peak amplitude greater than the base amplitude.

Figure 17:
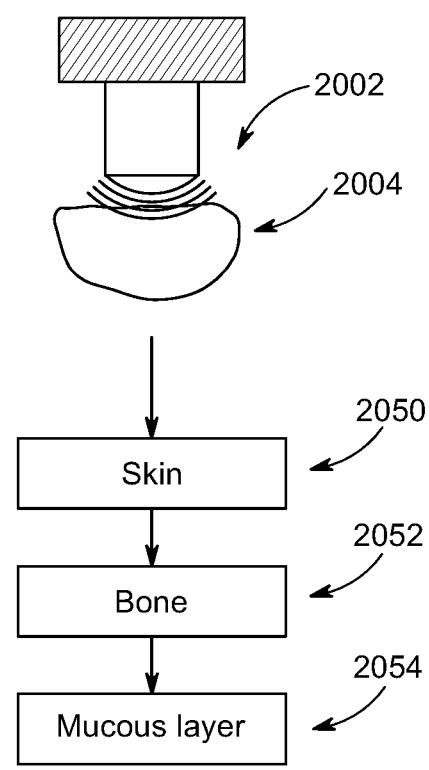
FIG. 17 depicts the interface between an ultrasound device and the tissues of the face.

FIG. 17 depicts the structural details of the ultrasound transmission from the skin through the bone and to the nerves which lie beneath the bones of the face. The end effector 2004 of the device 2002 communicates with the skin 2050 and from there, the vibrations travel through the skin 2050 to the bone 2052 and to the mucous layer 2054 underneath. From the bone, the vibration can be transmitted to the nerves in other regions of the face such as the sphenopalatine ganglia, the infraorbital nerve, the orbital nerve, the facial nerve, the trigeminal nerve, the ethmoidal nerve, and ultimately, the lacrimal nerve.

Direct stimulation of the mucous layer through bone also will accomplish direct treatment of sinus disease in addition to its effect on the nerves. Vibration and/or ultrasound stimulation of the mucosal layers will affect congestion directly by unplugging the outflow pathways and equalizing pressure.

Figure 18:
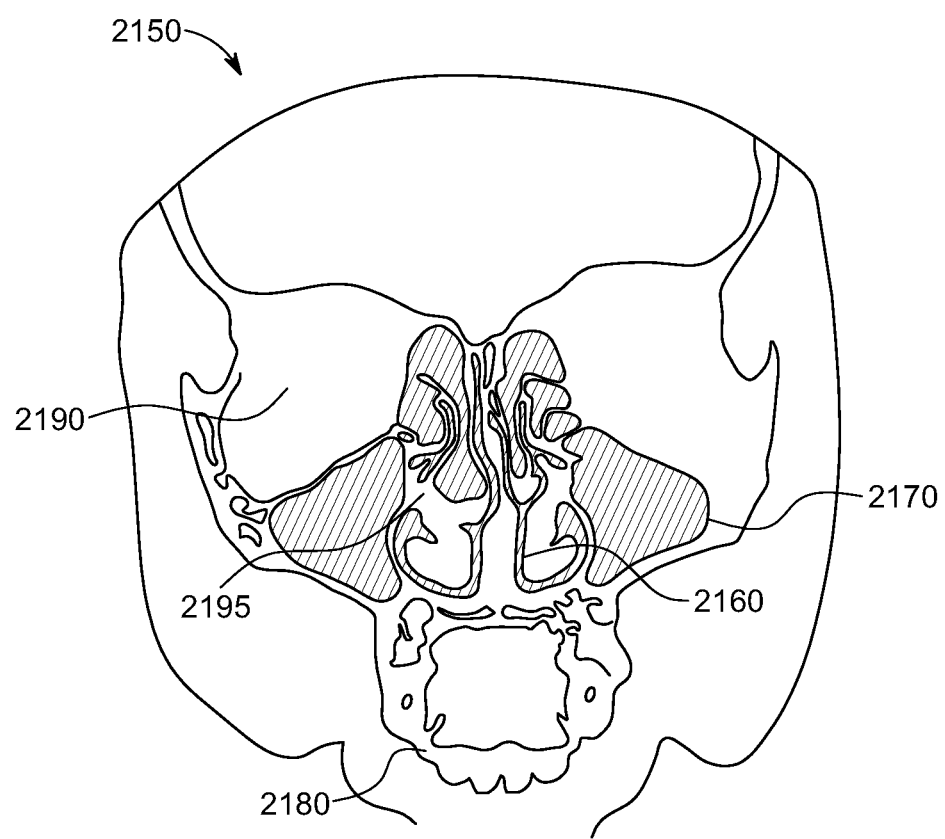
FIG. 18 depicts a coronal view of the sinuses.

FIG. 18 depicts several of the bony pathways which can communicate with nerve pathways via neuroacoustic conduction present inside the cranium 2150 and facial bones. The maxillary sinus and bone 2170 are the predominant pathway for transmission of vibratory energy to the sphenopalatine ganglia and ultimately the lacrimal nerve and gland. The conchae 2195 are folds of the maxillary bone which protrude partially into the nasal cavity. The conchae protect the olfactory bulb as well as the sphenopalatine ganglia but also play a role in transmission of sounds. The maxillary bone and its conchae communicate with the zygomatic bone 2190. The mandible 2180 represents an additional, albeit less direct pathway, for stimulation of the nerves of the facial region. In a preferred embodiment, a resonant frequency for these bones is utilized in order to transmit vibrational energy to the nerves within or below the bone to achieve a clinical end such as generating tears in the eye, stopping cluster headaches, migraines, seizures, rhinitis, and nasal congestion.

Figure 19:
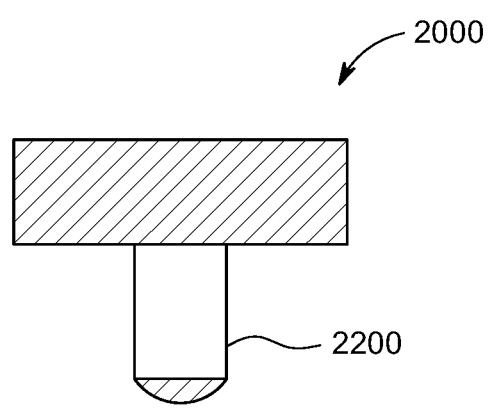
FIGS. 19 and 19A-21 depict variations of the end effector of a device designed to apply vibrational energy to the head and neck.
Figure 20:
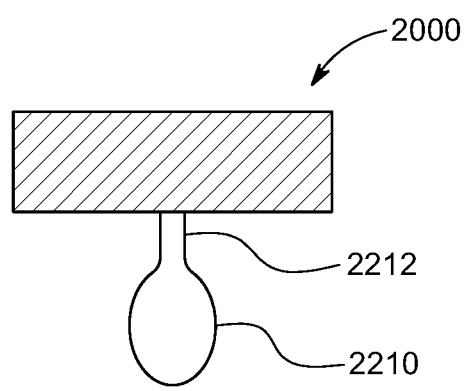
Figure 21:
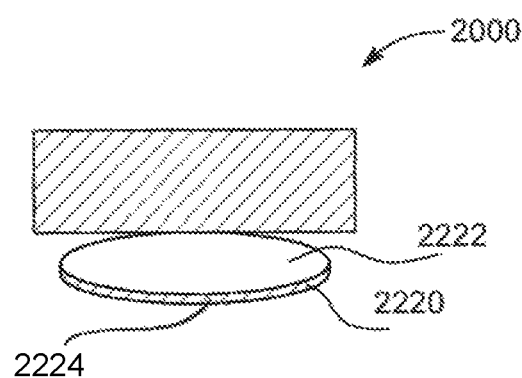

FIGS. 19-21 depict various end effectors 2004 (FIG. 17) of the device 2000 through which the vibratory energy is delivered transcutaneously to stimulate nerves of the facial regions, specifically the external nasal nerve.

FIG. 19 depicts an effector which is approximately 5 mm in diameter and longer than 2 cm. The tip is relatively flat and soft so that it can be depressed against the skin along the side of the nose to couple energy to the bone and the nerves beneath. The tip 2200 is rounded at its end and may be produced from a hydrophilic substance or a hydrogel or a more firm, harder material to facilitate coupling with the skin. A portion of the tip is more firm and rigid than another portion so that vibrational energy has a preferential direction as it is transmitted to and through the skin.

Figure 19A:
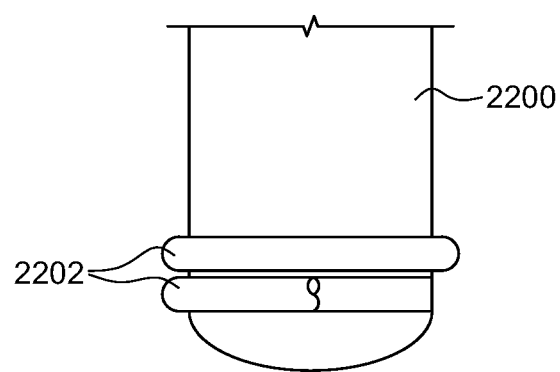

FIG. 19a depicts optional rings 2202 or constraining structures which circumscribe the tissue-engaging end of the tip to further enhance the ability of the tip to transfer vibrational energy into the skin.

FIG. 20 depicts another embodiment of an end effector to transmit energy through the skin to the bones and to the nerves underneath. In this example, the end effector is in the form of a small paddle 2210 with a thin flexible neck 2212 which can be applied to the skin regions which transmit vibratory energy to nerves. This embodiment allows the user to apply a variable pressure to the skin to modulate the vibration through the skin and bone to the nerve.

FIG. 21 is another embodiment of an end effector. In this example, the end effector 2222 is soft and compliant with an outer layer 2220 made from a hydrogel or other slippery material. A backing layer is disposed outside the slippery material so that the end effector can be depressed against the skin. The end effector may have an edge between 1 and 5 mm thick, the end 2224 (edge radius) being rigid so it may be depressed in the ridge on the side of the nose where the nasal cartilage meets the bone. The end 2224 can be rounded in some embodiments with a radius of curvature of 0.5 mm to 5 mm. The lateral curvature of the edge 2224 determines the sharpness of the tip, a key factor in the stimulation of the external nasal nerve. The smaller the radius and more severe the drop off along the radius to the outermost edge of the tip, the sharper the tip becomes.

In another embodiment, a method is described in which a location of maximal tear activity is determined by moving the applicator tip to different positions and angles.

Figure 22:
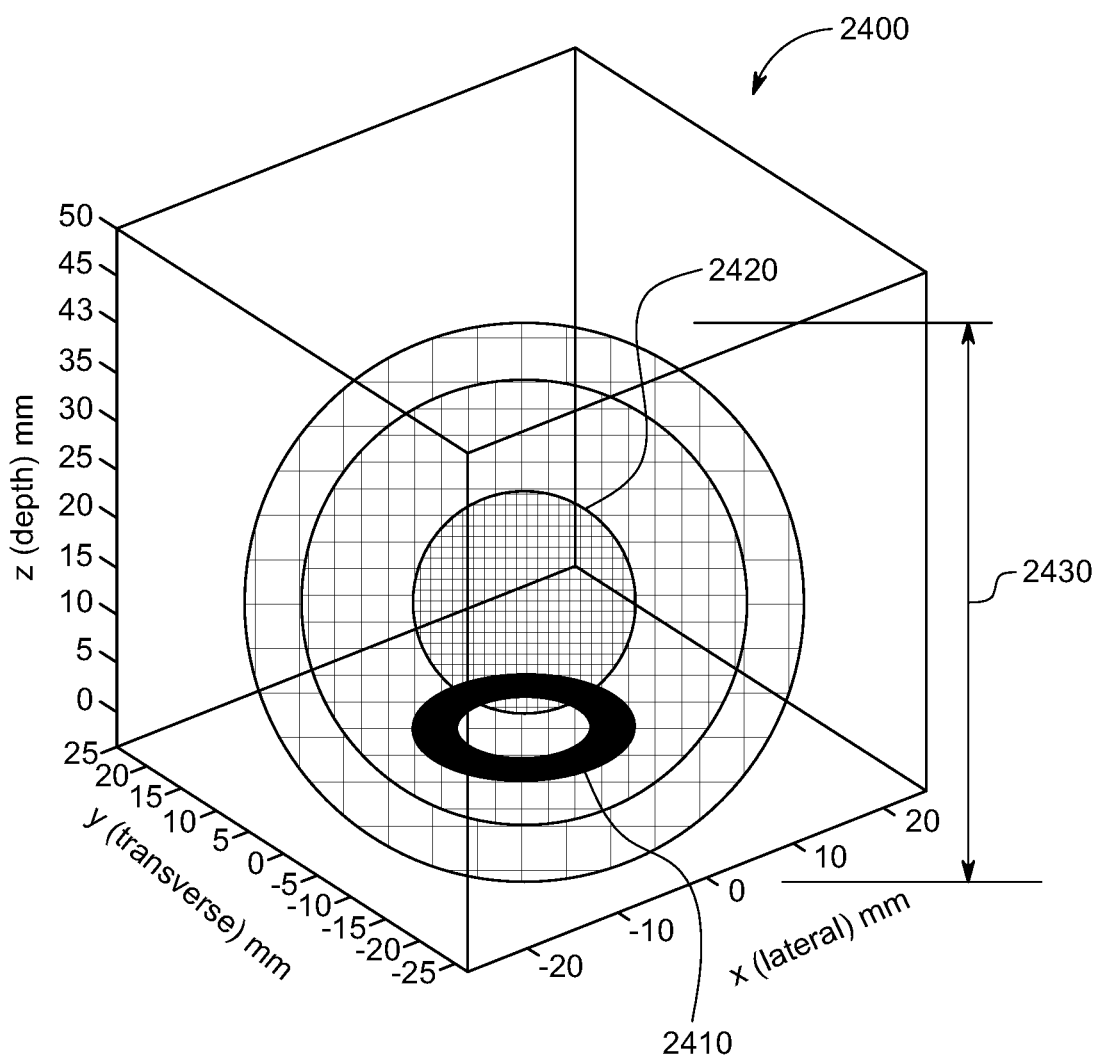
FIGS. 22-23 depict devices and simulation of devices to apply focused ultrasound to the retina.
Figure 23:
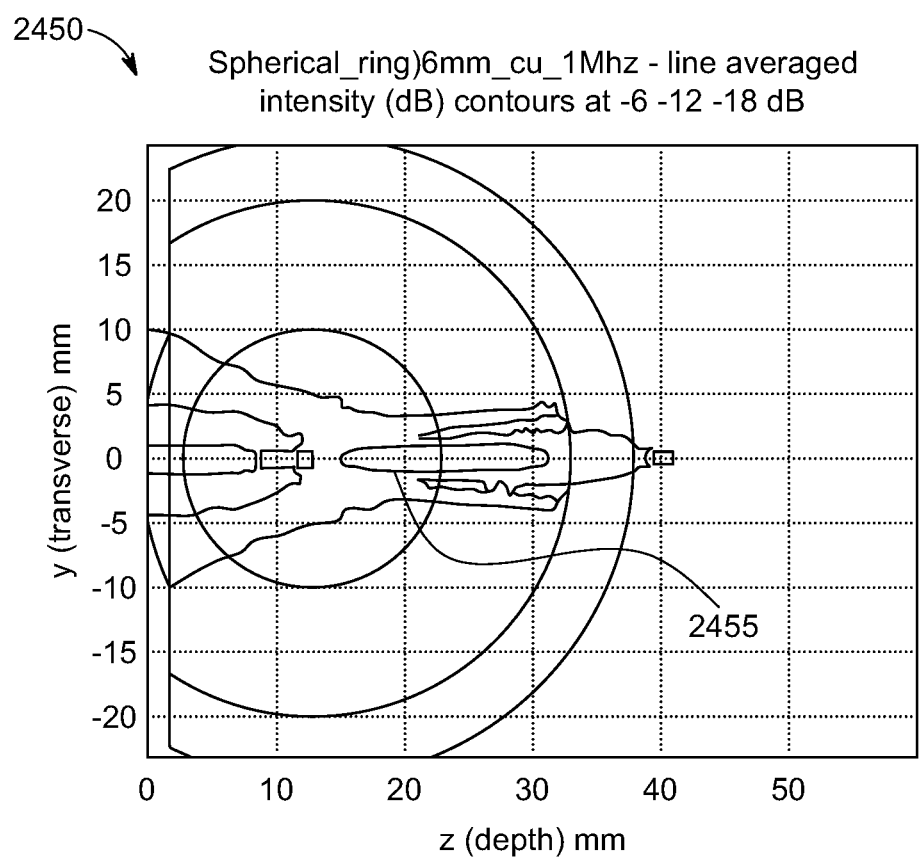

FIGS. 22-23. In another embodiment, a device is depicted which is designed to deliver focused ultrasound energy to the retina of an eye. FIGS. 22 and 23 depict a device and simulation respectively of the device on the tissues of the eye. Device 2410 is a ring shaped focused ultrasound transducer which is applied to the scleral region around the pupil 2420. FIG. 23 depicts the ultrasound field 2455 created by the transducer design. Ultrasound is focused at the back of the eye on the retina in this embodiment. The field is produced such that lens is spared and the surface intensity of the design is minimized so as to prevent damage to the sclera, trabecular meshwork, ciliary bodies, etc.

Figure 24:
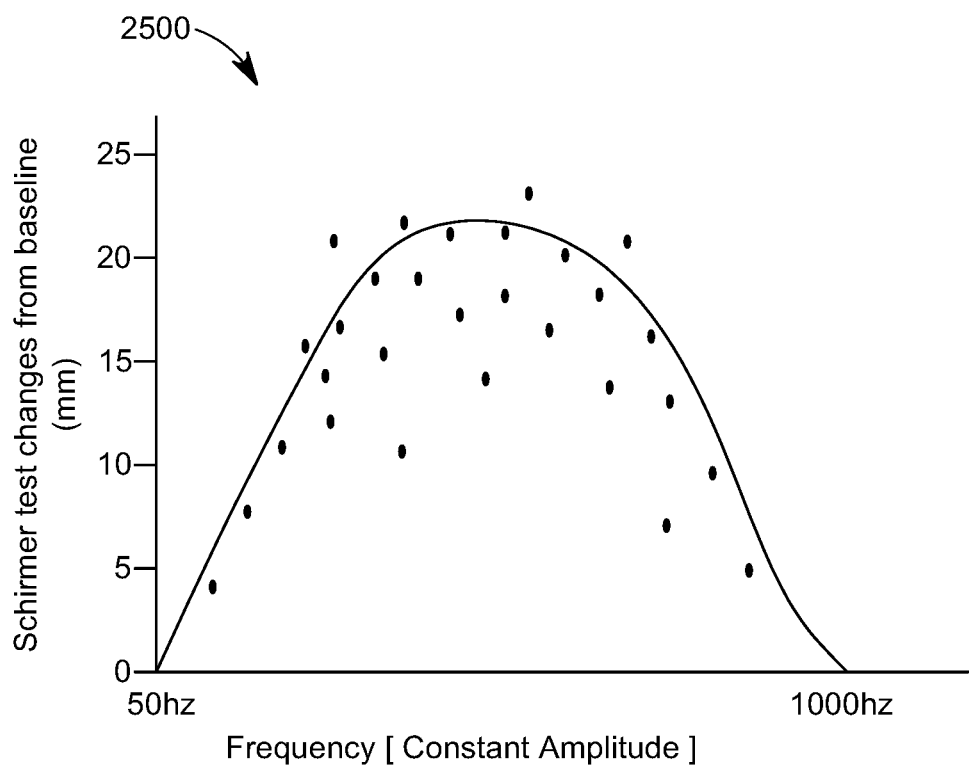
FIG. 24 depicts a graph of clinical data related to frequency vs response.

FIG. 24 depicts an experiment 2500 on human subjects performed with an embodiment of the current invention. With a constant amplitude of approximately 1 mm, a variable frequency was applied to the tear generation regions in and around the eye discussed herein. Tear generation was measured with a Schirmer test in which volume of tears is quantified with a test strip. It was found that at the extremes of the frequency (e.g. 50 Hz and 1000 Hz), there is very little response as far as tear generation and that tear generation peaked (using a Schirmer test to quantify the volume to tears) at about between 200 and 300 Hz. Furthermore, outside of the tear generation points on the face, there was no generation of tears in the patients. For example, application of the device to the lips, the distal edge of the nose, the forehead above the eyebrows, and the teeth did not result in tear generation showing that indeed it is frequency and position which are most important to stimulating the lacrimal glands. The external nasal nerve was directly stimulated when the device was compressed against the nasal bone where the upper lateral nasal cartilage meets the nasal bone and a frequency of about 200-300 Hz is applied using amplitude of about 1-2 mm.

Figure 25:
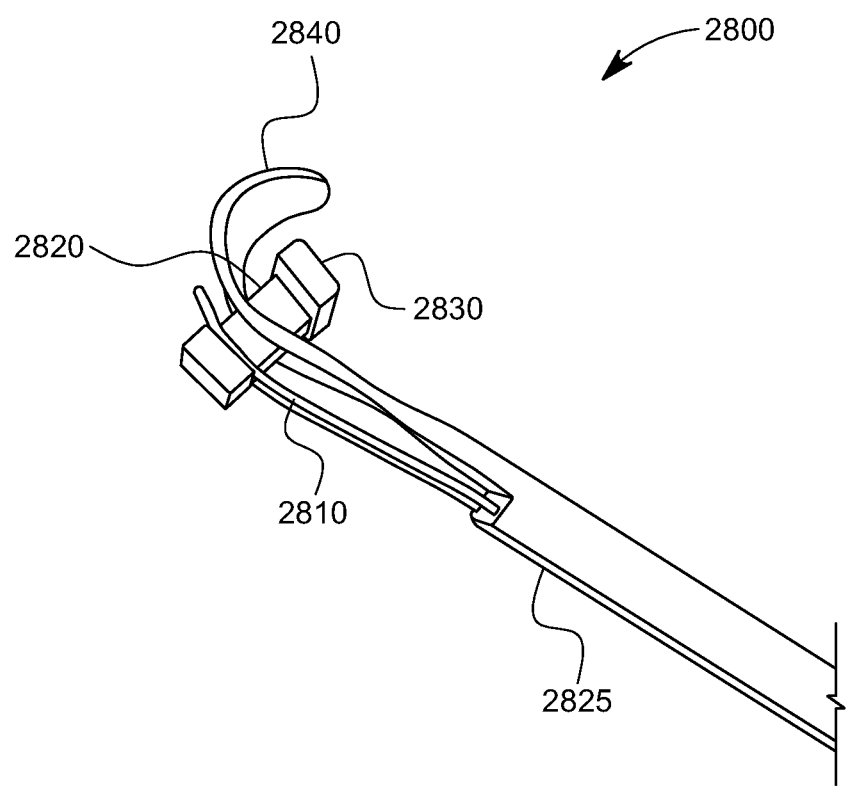
FIG. 25 depicts a handheld device to apply pressure and heat to the eyelid.

FIG. 25 depicts a close up configuration of a device 2800 to treat Meibomiam gland disease in dry eye. An eyelid region between 2830 and 2840 is depicted between an end of a lid retractor edge 2840 and a flexible component of the retractor 2830 which is configured to enable pressure to the eyelid which is sandwiched between the flexible component 2830 and the tip of the retractor 2840. Element 2810 is a lever for the user to control the pressure and manipulate flexible component 2820 and 2830. In another embodiment, component 2820 and 2830 are not flexible but is a vibrating element such as a linear resonant actuator (LRA) which can vibrate at the optimal frequencies determined by the experiment shown in FIG. 24. In some embodiments, element 2820 and 2830 are flexible and vibrate.

This device 2800 combines pressure along with the ability of the user to "milk" the glands while the eyelid is being retracted away from the sclera. Vibration and heat are also optionally provided by the device so as to create synergistic effects on the glands and lids.

Figure 26:
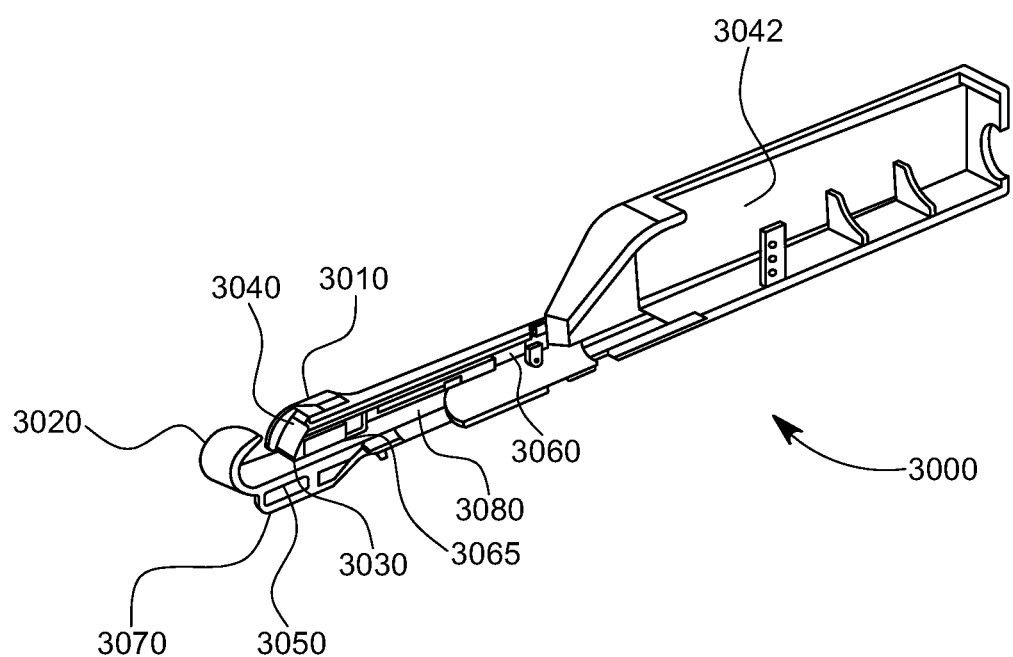
FIG. 26 depicts a view of a handheld device to apply energy to the eyelid.

FIG. 26 depicts an embodiment of a device to apply several forms of energy to an eyelid. The eyelid is positioned between a retractor member 3020 and a pushrod member 3010. Inner shaft 3060 slides along outer shaft 3080 to move the pusher member 3010 so it applies pressure to the eyelid between the inside of the retractor member 3020 and the pushable member 3040. Inner member 3060 is attached to housing 3042 by a spring which retracts the inner member when the operator of the device releases the inner member 3060. Without operator application of force to the inner member, the inner member springs back to the baseline state where no pressure is applied to the eyelid. Such design is created for safety. Without operator force, the inner member is harmless because it retracts into the housing 3042. The spring on the inner member can also be used to measure or quantify the force being applied to the eyelid so that the operator of the device will have a sense of how much pressure he or she is applying. The force which is applied can be signaled to the user of the device with vibration or sound to indicate when a safe and proper force is being applied to the eyelid.

The device in FIG. 26 optionally contains an ultrasound element 3030 on the inner shaft 3010 and/or the outer shaft 3020 which can generate ultrasound at frequencies from between 20 KHz to 30 MHz. In a preferred embodiment, the frequency is between 3 MHz and 10 MHz or between 500 kHz and 3 MHz depending on the desired effect. Ultrasound at these frequencies efficiently generates heat into the eyelid and can also break up the inspissation in the blocked ducts. Importantly, heat is delivered to the inside of the eyelid via ultrasound which penetrates the eyelid and effectively heats at tissue planes inside the lid. Heat is not delivered via conduction from the outer or inner lid to the glands as it is in all devices in widespread use today. Rather, heat is applied to and through the eyelid via a non-conductive process. The surface and skin of the eyelid remain at body temperature (38-40 C) or slightly above while the inner eyelid is heated to over 42 C (42-48 C). Furthermore, vibratory devices 3050, 3065 are incorporated into the outer shaft 308 or inner shaft 3060 respectively which can add additional mechanical energy to the eyelid. The vibration frequency can range anywhere from about 50 Hz to about 500 Hz with an amplitude of anywhere from about 100 microns to 3 mm as depicted in FIG. 24 and described above. Either the inner member 3010 and/or the outer member 3020 optionally contain a temperature sensing element such as a thermistor as well as closed loop control of the heating based on the temperature. In one embodiment, a control circuit is integrated into device 3000.

In another embodiment, element 3030 is a light emitting diode or similar heat generating element. An infrared diode will generate infrared energy through the eyelid and also heat the glands non-invasively.

Device 3000 preferably contains self-contained power supply which is rechargeable. A base can be provided which contains a power supply is to recharge the device 3000. In some embodiments, the rechargeable power supply is built into device 3000 and the entire unit is rechargeable.

Figure 27:
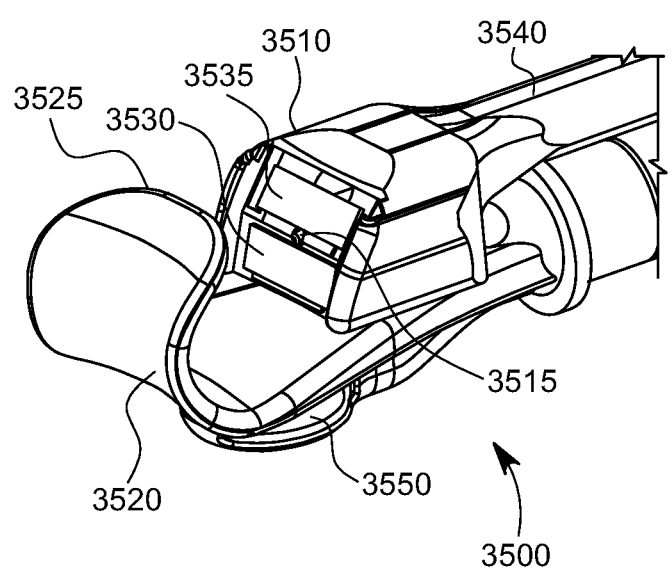
FIG. 27 depicts a close-up of a handheld device to apply ultrasound to an eyelid.

FIG. 27 depicts a larger view of the retractor device 3500 with the inner pushrod 3540 and outer retractor 3520 along with the vibratory element 3550. Ultrasound elements 3530 and 3535 are configured to deliver ultrasonic energy to the eyelid which is compressed between the inner pushrod 3540 and the outer lid retractor element 3520. Element 3515 is a connector to enable the inner pushrod to spring back automatically to the home position (shown in FIG. 27). Because element 3515 in some embodiments is elastic, it enables quantification of the force applied to the eyelid and/or springs back during application for quick release if there is patient discomfort.

Vibrating element 3550 transmits vibration to the tip through the curved portion of the retractor 3520. The tip 3525 contacts the conjunctiva at the mucocutaneous junction of the inner eyelid to create tears, stimulate the Meibomian glands to open and to induce secretion of lipids and oils from the glands to produce a long lasting tear film. Additionally, the embodiment in FIG. 27 comprises range finding elements such as a camera, laser, or ultrasound range finder which can be utilized to mark the distance of the device from the surface of the eye so that it is considered a safe device and procedure. In this embodiment, when the vibrating tip is placed too close to the eye without retraction of the eyelid away from the sclera of the eye, a shutdown occurs and the device does not operate.

Device 3500 enables a method whereby the eyelid is retracted with retractor 3525, push rod 3540 is pressed against the outer eyelid and the eyelid is compressed between retractor 3520 and pushrod 3540, the pressure optionally measured by elastic recoil element 3515. Heat and vibration from ultrasound element 3535 is applied to the eyelid to create tearing, break up inspissations in the Meibomian glands, and stimulate the glands to secrete oils and proteinaceous materials. Pressure can be quantified and controlled using elastic element 3515. The eyeball, sclera, cornea, etc. are protected from heat, ultrasound, and pressure via the retractor which pulls away the lower eyelid. Thermistor 3535 allows for temperature measurement and control of the ultrasound power so that the element does not overheat and the tissue is not burned. The operator can set the temperature limit within a specified range, for example, 42 C to 48 C.

Further treatment effect can be achieved in one embodiment with mechanical vibration using linear resonant actuators or similar vibrating elements on the implement 3550 and 3510. These mechanical vibrators which vibrate at between 200 and 300 Hz can be used alone or in combination with the rest of the device to open Meibomian glands and stimulate nerves to secrete tears, oils, and proteinaceous materials.

Figure 28:
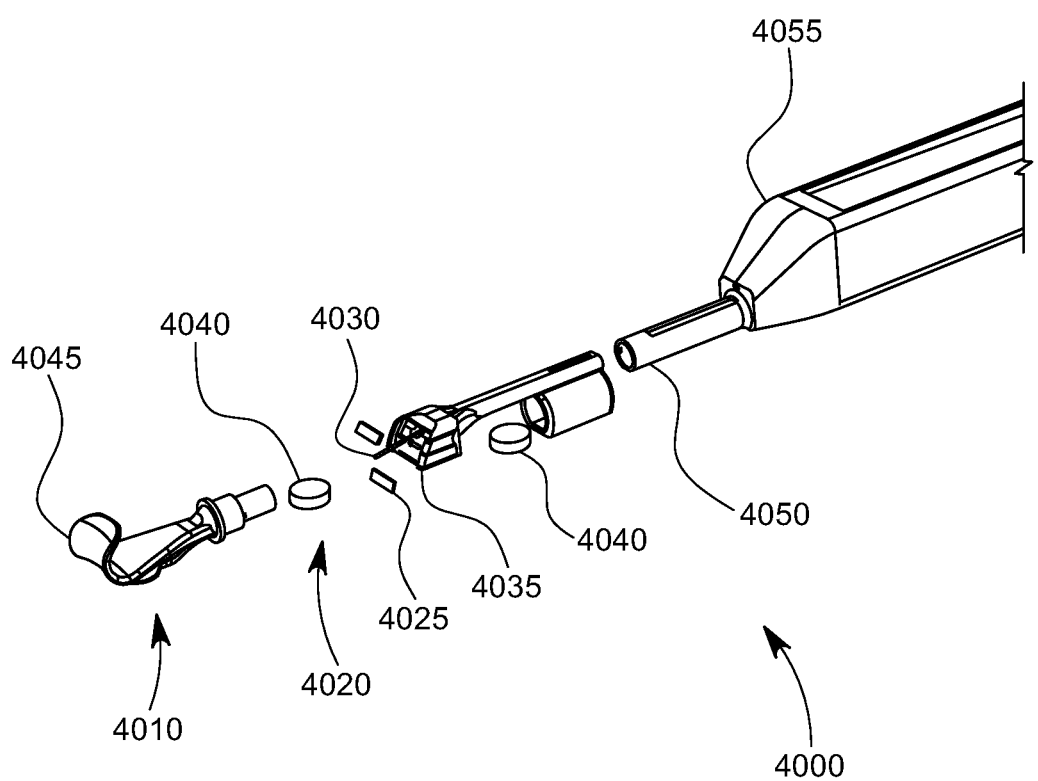
FIG. 28 depicts an exploded view of a handheld device to apply several forms of energy to the eyelid.

FIG. 28 is an expanded view of the device with the ultrasound element 4025 on the inside 4035. "Inside" refers to the pushrod 4035 which contacts the outer portion of the eyelid. In this embodiment, the ultrasound element contacts the outer portion of the eyelid but in other embodiments, the ultrasound element contacts the inside of the eyelid in which case it is placed on the retractor portion 4045 of the device 4000. In some embodiments, the ultrasound elements 4025 are placed such that they contact both the inside and outside of the eyelid. Linear resonant actuators (LRA) 4040 can be similarly placed on both the outer and inner components or just one or the other components. In some embodiments, a voice coil is used and actuated via portable battery. Wire 4030 may carry current or is flexible or both. It is connected to the inner pushrod 4035 to stabilize it, retract it, or carry electrical current to the tip of device 4000. If flexible, it can be attached to a strain gauge or pressure sensor. In one embodiment, the flexible wire is configured such that it retracts the inner pushrod back from the position in which the eyelid is pressurized by the inner and outer pushrods. Through hole 4050 houses the elastic band or wire 4030 through which it anchors in housing 4055. Housing 4055 may contain a DC battery and circuitry to drive the LRA. Outer retractor 4045 is composed of a comfortable and biocompatible material to retract the eyelid. For example, outer retractor 4045 is made from a hydrogel or a PTFE material. In another embodiment, outer retractor 4045 is made from a spongy material with some compliance when depressed against a lid. An advantage of placing the ultrasound transducers on pushrod 4035 to contact the outer portion of the lid is that the outer retractor 4045 may be optimized for comfort without the additional compromise of having piezoelectric materials for ultrasound generation embedded inside.

Figure 29:
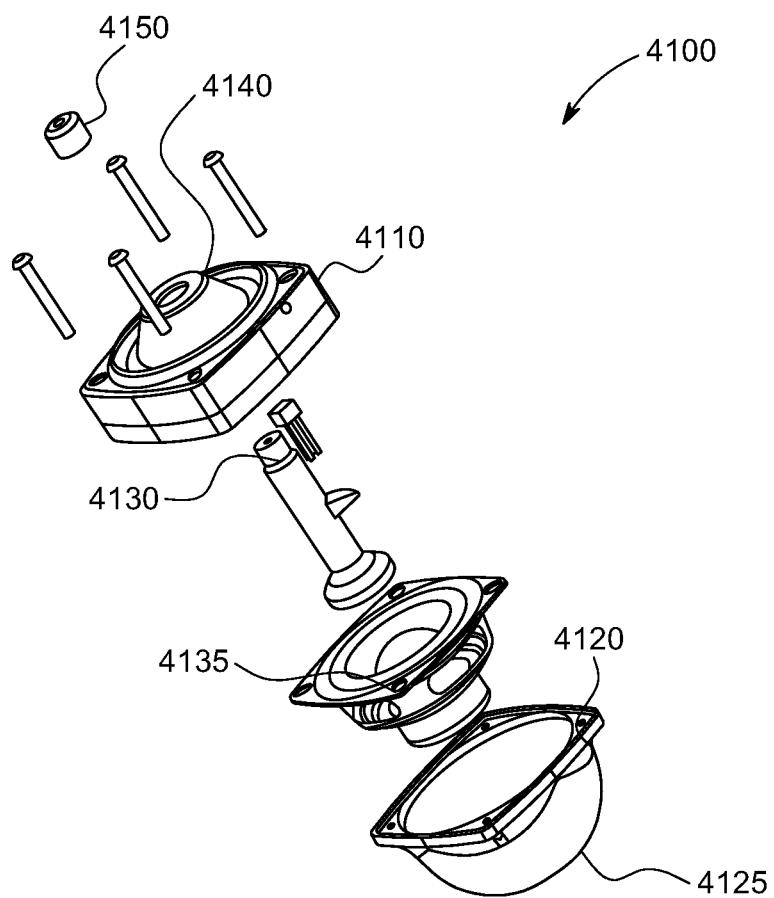
FIG. 29 depicts an assembly schematic for a device to apply vibrating energy to nerve trigger points on a face.

FIG. 29 depicts the expanded components of one embodiment of a device to stimulate tears 4100. 4120 is the housing with an advanced user interface to allow for gripping the device and then applying to the external nasal nerve of a patient. Grip 4125 is a user interface for the device which contacts the palm of the user to allow for manipulation of the device while the biocompatible tip 4150 is manipulated and applied to the skin of the patient. The material is biocompatible and firm. Speaker or voice coil 4135 is the heart of the system, allowing for a continuous spectrum of frequencies, from 50 Hz all the way to kHz frequency as well as modulation of driving amplitude. Skin interface 4150 is stabilized by frame 4110. Frame 4110 also enables finger grips for further manipulation of the device. The skin interface 4150 is a biocompatible skin interface which allows for the application of cyclic force to the external nasal nerve, compressing the nerve against the nasal bone at a frequency of approximately 175 Hz to stimulate the nerve to generate tears. Shaft 4130 underneath the end effector is driven by the speaker to then drive the end effector element 4150. Interface 4140 provides the transduction interface between the speaker 4135 and the end effector 4150.

FIG. 30 depicts nasal anatomy. The frontal bone 5150 forms the upper boundary of the orbit and maxillary bone 5205 forms the medial boundary of the orbit. The frontal bone forms the roof of the frontal sinus. Maxillary bone forms the roof of the maxillary sinus 5260. The nares 5310 is the communication between the outside and the internal mucosa of the nose. The external nasal nerve 5215 leaves the nasal cavity through an orifice 5215 between the nasal bone 5200 and the lateral processes of the septal nasal cartilage 5210. It has been discovered that stimulation of the external nasal nerve in this region 5215 with force between 1-4 N using vibration at 100-300 Hz results in several clinical effects including creation of tears, abrogation of allergic and vasomotor rhinitis, relief from sinusitis, stimulation of Meibomian glands, treatment of headaches, and narcolepsy.

FIG. 31 depicts the cutaneous nervous anatomy 5000 in and around the nasal cavity. Cutaneous, or subcutaneous, generally refers to nerves covered by skin, dead stratified squamous, keratinized epithelial cells. In contrast, mucosa or sub-mucosal, nerves are covered by non-keratinized mucosal epithelial cells which are generally ciliated and columnar. Cutaneous nerves are more difficult to reach with certain energy forms (e.g. electrical stimulation) because the dead stratified layers broadly diffuse the current. However, vibratory stimulation can be directed to the nerves underlying the skin by transmission of pressure waves. The external branch of the anterior ethmoidal nerve 5020, also referred to as the external nasal nerve, exits at the caudal portion of the nasal bone and supplies the ipsilateral side of the nose with cutaneous nerve fibers. Infraorbital nerve 5010 supplies cutaneous fibers to the lower eyelid, upper lip, and a portion of the nasal vestibule; the vestibule is the most anterior part of the nose, lined by the same epithelium as the skin. Its epithelium transitions to the respiratory epithelium of the nasal cavity proper. The infratrochlear nerve 5035 supplies the skin of the upper eyelids, bridge of the nose, the conjunctiva, lacrimal sac, and the caruncle (small, pink, globular nodule at the inner corner of the eye made of skin covering the sebaceous and sweat glands). The supratrochlear nerve 5030 supplies the skin of the lower forehead, the conjunctiva and the skin of the upper eyelid. It has been discovered through experimentation described herein that vibratory stimuli (e.g. 50 Hz to approximately 300 Hz) of these nerves and nerve endings stimulate the lacrimal nerve to secrete tears. In these embodiments, the vibratory stimuli contact the stratified epithelium of the skin not the mucosa and energy is transferred by mechanical waves.

In one embodiment, the lacrimal gland is activated by stimulating the infraorbital nerve, the infratrochlear nerve, the supratrochlear nerve, the caruncle or the conjunctiva inside the eyelids. Indeed, the conjunctiva inside the eyelids or on the surface of the eye is mucosa and the upper layers are non-keratinized. Stimulation of these tissues is optionally performed with vibratory energy including sound, ultrasound, mechanical vibration, electrical sparking, puff of air, puff or water or other liquid, or other mechanically sharp stimulation impulse. In the mucosal tissues, electrical stimulation is also more possible because of the lack of stratified epidermis diffusing the current. Therefore, in one embodiment, current is passed through the conjunctiva of the eye to stimulate tears.

Figure 32:
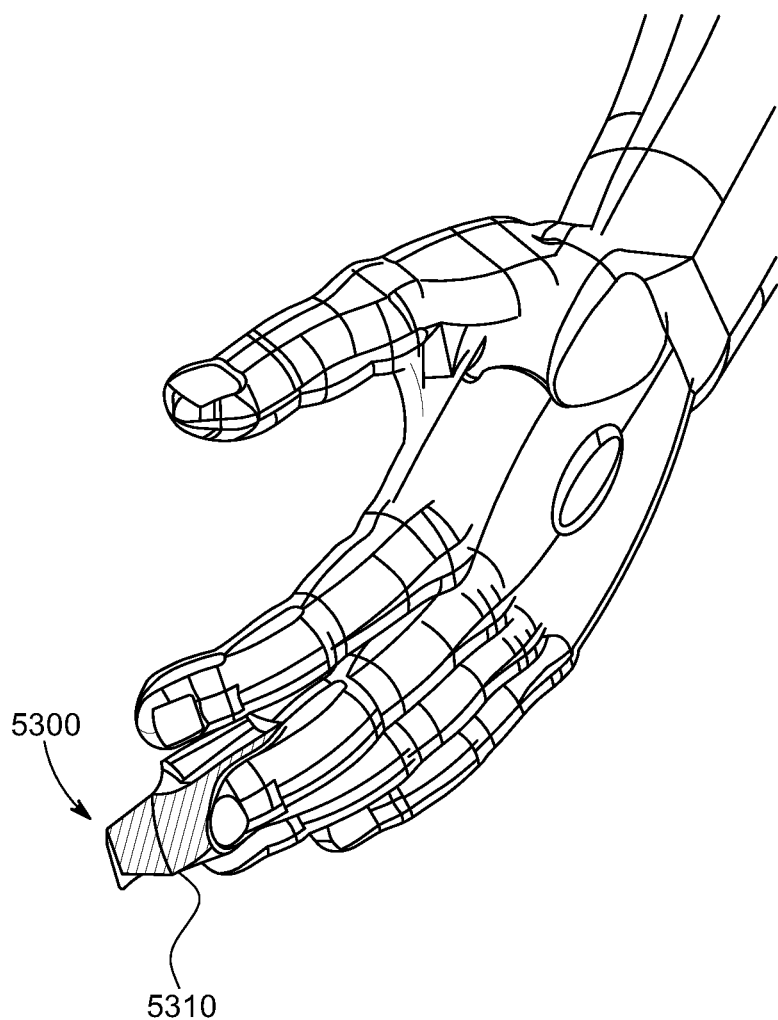
FIG. 32 depicts an embodiment of a tear stimulator

FIG. 32 depicts an embodiment of the current invention 5300. Stimulation device 5310 couples to the finger of a subject. In this embodiment, the patient or the user retracts their eyelid with his or her finger and applies the stimulation to the eyelid with another finger. In one example, this embodiment incorporates a linear resonant actuator with an edge configured for application to the eyelid. In another embodiment, electrodes on the device deliver current across the mucosa. The fingertip is chosen in this embodiment as it affords the user to finely manipulate the vibration or other energy which is very important when applying energy around the eyelid.

Figure 33:
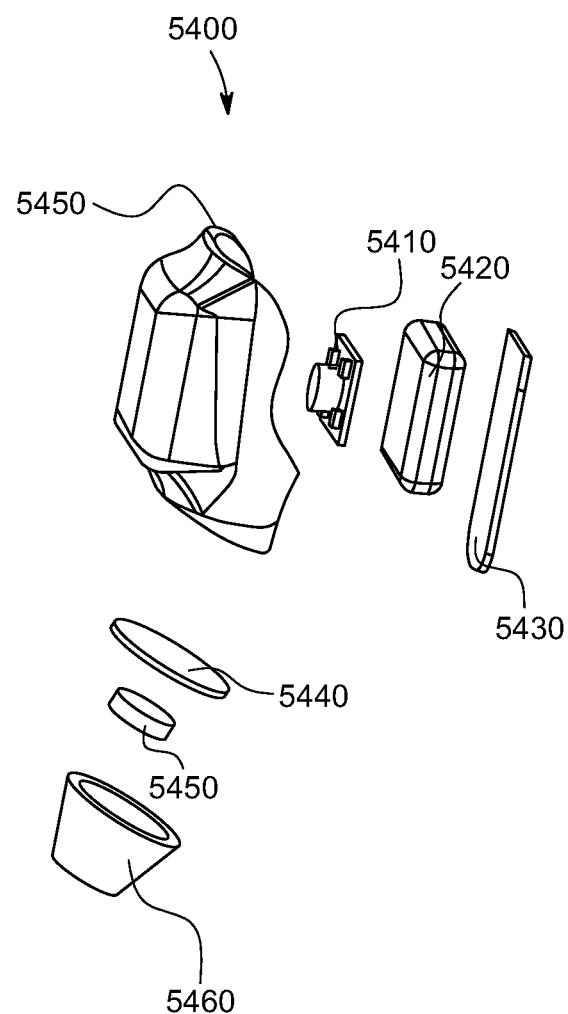
FIG. 33 depicts a detailed drawing of a tear stimulator

FIG. 33 depicts the components of the finger stimulation device 5400 shown in FIG. 32. Linear resonant actuator (LRA) 5450 couples to end effector 5460 which contacts the caudal portion of the nasal bone at the exit of the external nasal nerve. The linear resonance actuator is configured to generate linear motion and apply a force of between 1 and 5 Newtons or 2-5 lbs. Backing 5440 directs the LRA 5450 and biocompatible interface 5460 to a predominantly linear direction to maximize the energy applied against the nerve. The power button and driving circuit 5410 is powered by a rechargeable battery 5420.

Figure 34:
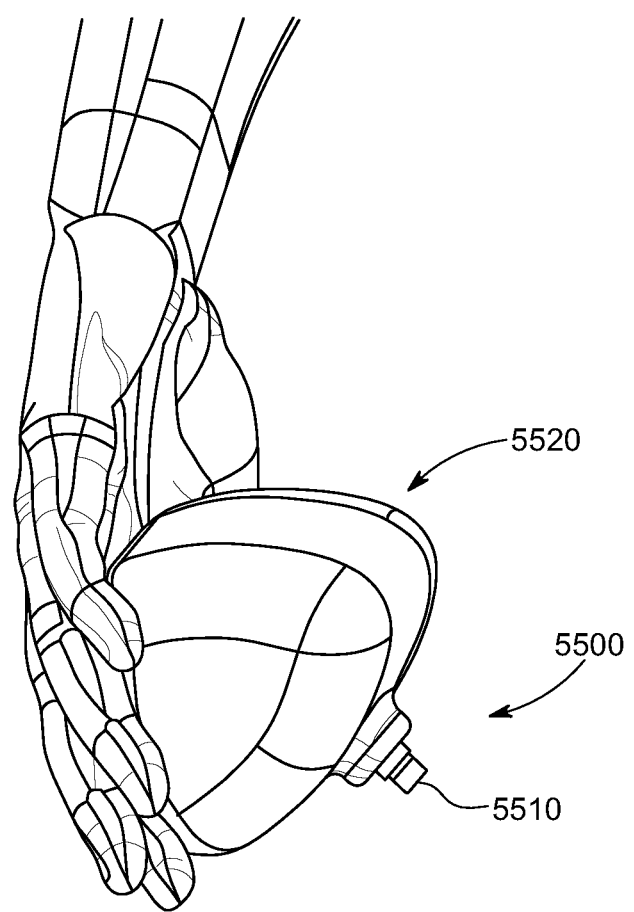
FIG. 34 depicts an embodiment of a handheld tear stimulator.

FIG. 34 depicts a handheld embodiment of a device 5500 to apply vibrational energy to the facial region in which there is an underlying parasympathetic nerve or a circuit which ultimately results in stimulation of a parasympathetic nerve. Interface 5510 moves with linear excursion substantially perpendicular to the housing 5520. Housing 5520 is configured to be handheld and self-contained, produced from a comfortable, biocompatible plastic or aluminum material. Interface 5510 is fairly rigid with a rounded yet firm tip. The radius of curvature of the tip is such that it can firmly push into the junction of the nasal cartilage and nasal bone, vibrate a 100-300 Hz, preferably between 180 and 220 Hz or at least between 75 Hz and 300 Hz with maintenance of a constant speed despite the force being applied by the user to the nerve.

Figure 35:
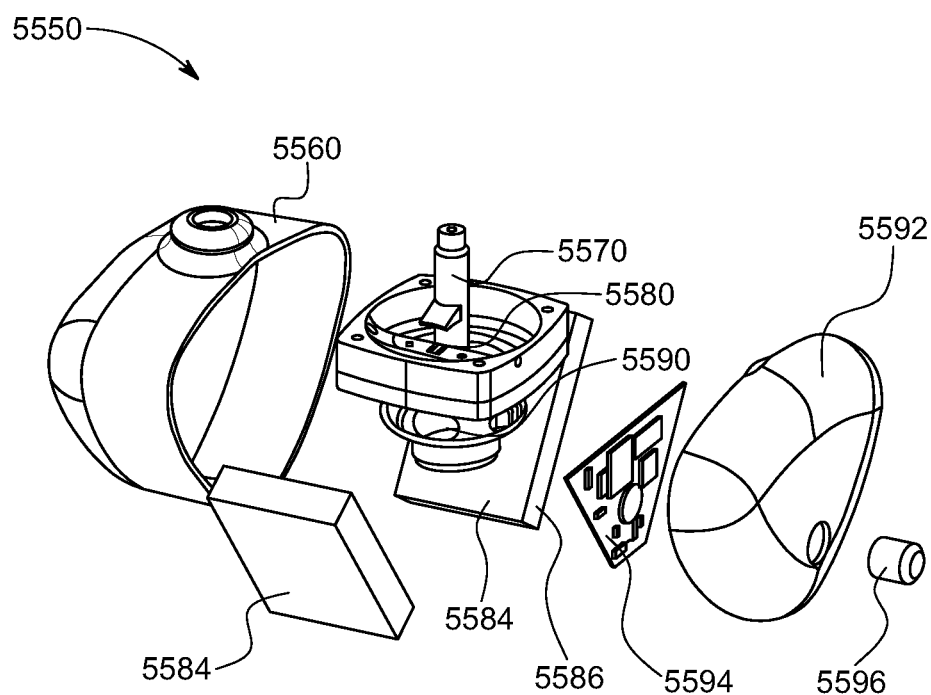
FIG. 35 depicts an expanded view of a handheld neurostimulator to create tears.

FIG. 35 depicts a detailed view of the handheld device in FIG. 34. The basic mechanism of this device is a voice coil 5590 which provides for a linear driving motion of the tip 5570. Plastic body 5560, 5592 surrounds the device. An optical distance sensor 5580 is calibrated to detect movement of the linear vibrating component 5570. Printed circuit board assembly 5594 comprises an amplifier and battery charging circuitry as well as an optional control system so that the tip 5570 vibrates at a near constant frequency. Power button 5596 and cover 5592 as well as lithium ion batteries 5584 and 5586 complete the unit. This unit is self-contained and the lithium ion batteries are rechargeable.

Figure 36:
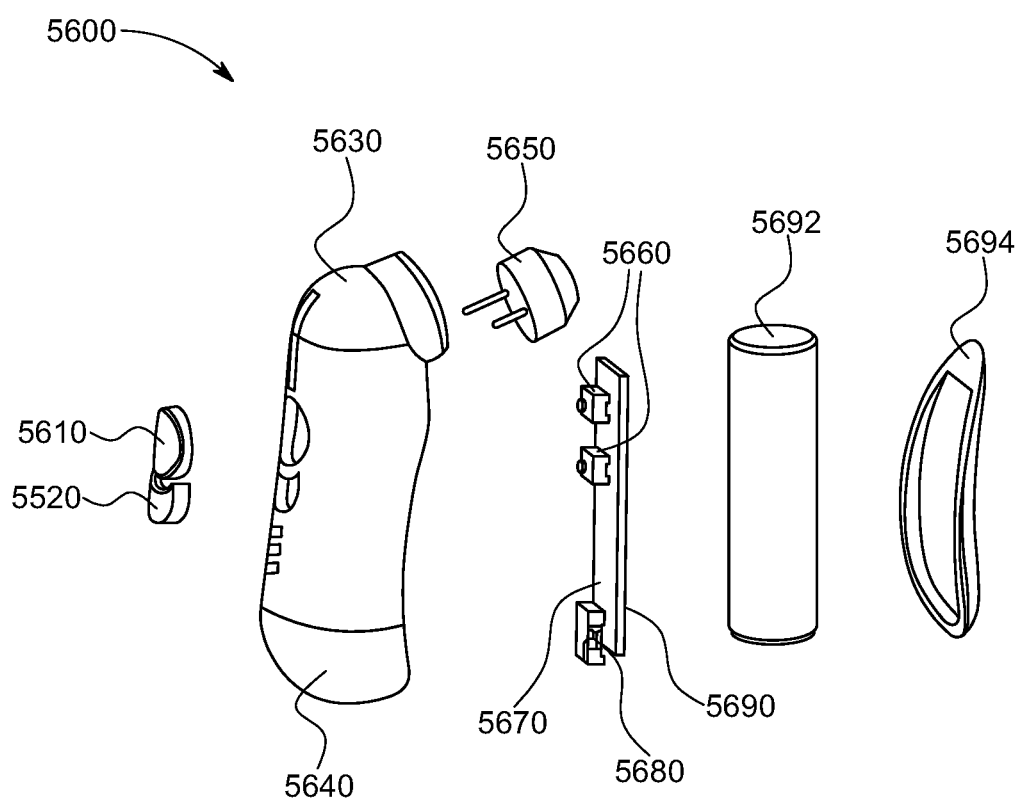
FIG. 36 depicts an expanded view of a neurostimulator device.

FIG. 36 depicts the components of a vibratory device 5600 which is configured to be held in the palm of the hand of the user with an interface with the tip of a finger of a user. Body surface interface 5650 is configured to be handheld and comfort grip 5694 is configured from a biocompatible material. Lithium ion 5692 battery is inserted into the main body housing 5640. Linear vibration motor 5650 travels with linear motion and is connected to the body surface interface to create linear motion as well. The surface interface is applied to the skin with perpendicular application to the skin to stimulate the external nasal nerve and the parasympathetic nervous system to open Meibomian glands, create secretions of oils, and produce tears from the lacrimal glands, treat migraines, epilepsy, narcolepsy, headaches, open blood brain barrier, equalize pressure, treat rhinitis and sinusitis, and nasal polyps. Tactile switches 5660 enable user guided feedback to increase or decrease stimulation level, either by signaling adjustment of the vibration amplitude and/or frequency.

Figure 37:
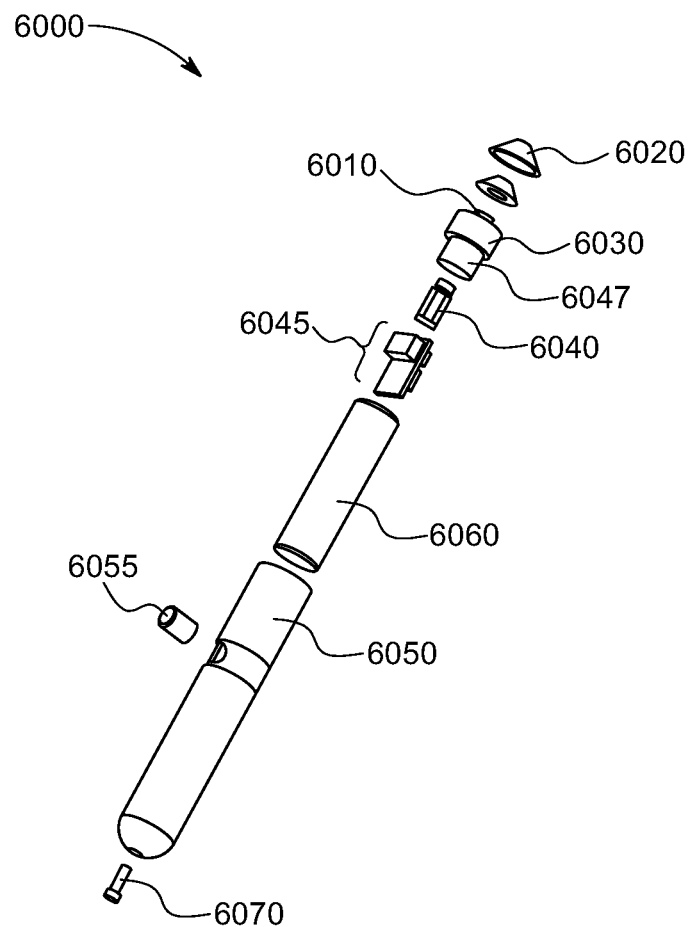
FIG. 37 depicts an expanded view of another neurostimulator device.

FIG. 37 depicts another embodiment of a device 6000 configured to apply vibrational energy to a nerve overlying a parasympathetic nerve of the face. Interface 6020 is a biocompatible skin interface designed to transfer force from the vibratory element to the skin overlying the bone of the patient and to the nerve underlying the bone. A snap element 6010 allows for quick placement and removal of the skin interface 6020. The vibration is generated by eccentric motor 6040 which vibrates the biocompatible interface with an approximately planar and perpendicular vibratory direction to the long axis of the device 6000. Switch 6055 powers the device on and off. Rechargeable battery 6060 and electrical access port 6070 enable power delivery to the device 6000. Additional electronics 6045 may include a lockout timer so that a user does not over use the device. A control system to maintain a pre-specified motor and vibration speed is also an optional feature of the circuitry. The electronics are housed in shell 6050.

Figure 38:
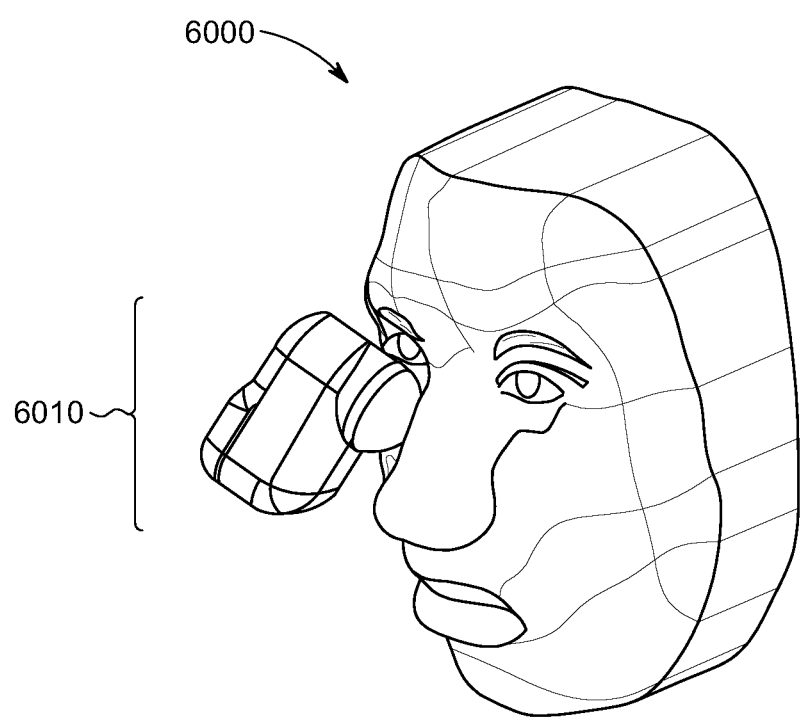
FIG. 38 depicts another embodiment of an external nasal neurostimulator

FIG. 38 depicts an embodiment of a vibratory device 6000 in which vibratory energy is applied to the mucocutaneous junction where the skin of the eyelid meets the conjunctiva. The nerve endings of the eyelid are stimulated in this embodiment and energy is applied to the mucocutaneous junction to create tears and unblock and stimulate Meibomian glands. Device 6000 comprises a vibratory, sound, or ultrasound generating component which can be coupled to the eyelid. In one embodiment, the device further incorporates suction to grab on to the eyelid during the treatment. In another embodiment, the device incorporates a grip like a pair of tweezers or forceps to hold the eyelid while the energy is applied.

Figure 39:
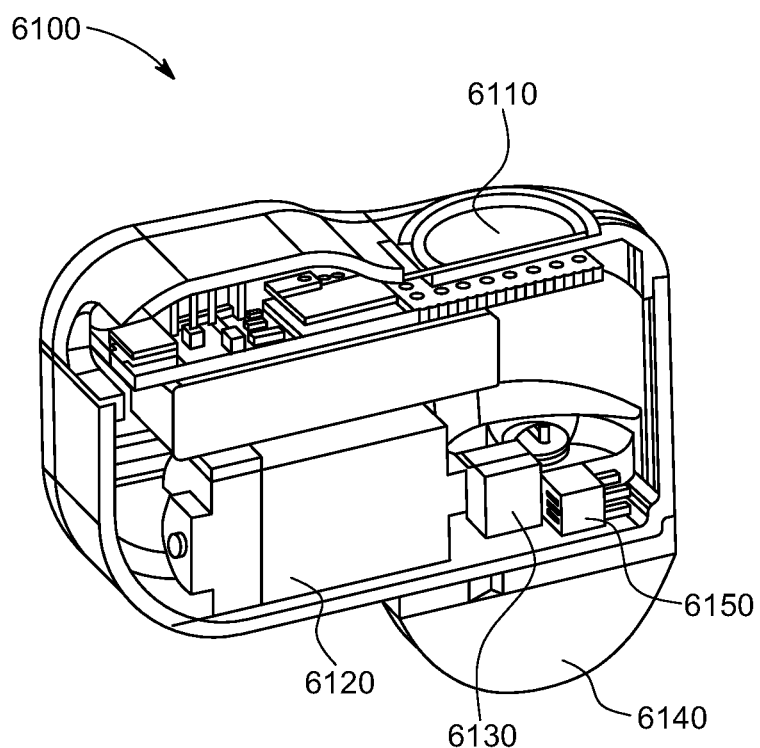
FIG. 39 depicts a schematic of the inner workings of the device shown in FIG. 38.

FIG. 39 depicts the inner workings 6100 of the device in FIG. 38 which applies vibrational energy to the mucocutaneous junction of the eyelid. Pressure sensitive switch 6110 controls the vibrational energy with pressure. Importantly, eyelid interface 6140 in configured to interface with the eyelid. It is comprised of a biocompatible material and comprises a mechanism to pull away the eyelid while applying vibration or ultrasound so as to protect the sclera and cornea. A standard motor 6120 drives the device 6100. Optionally, the motor 6120 is connected to a weight 6130 to create eccentricity and vibration. Elastomer pad 6150 is a biocompatible interface with the skin of the patient or device user. The pad is characterized by a shore durometer of between 20 A and 50 A. In another embodiment, a linear resonant actuator is utilized to couple vibration to the mucocutaneous junction of the eyelid. In this embodiment, vibrations of about 50 to 300 Hz have been found to be optimal to stimulate the nerve endings in the conjunctiva present on the eyelid. The pathway in this embodiment is presumed to be both a neural reflex pathway and mechanical pathway in which the glands are stimulated.

Figure 40:
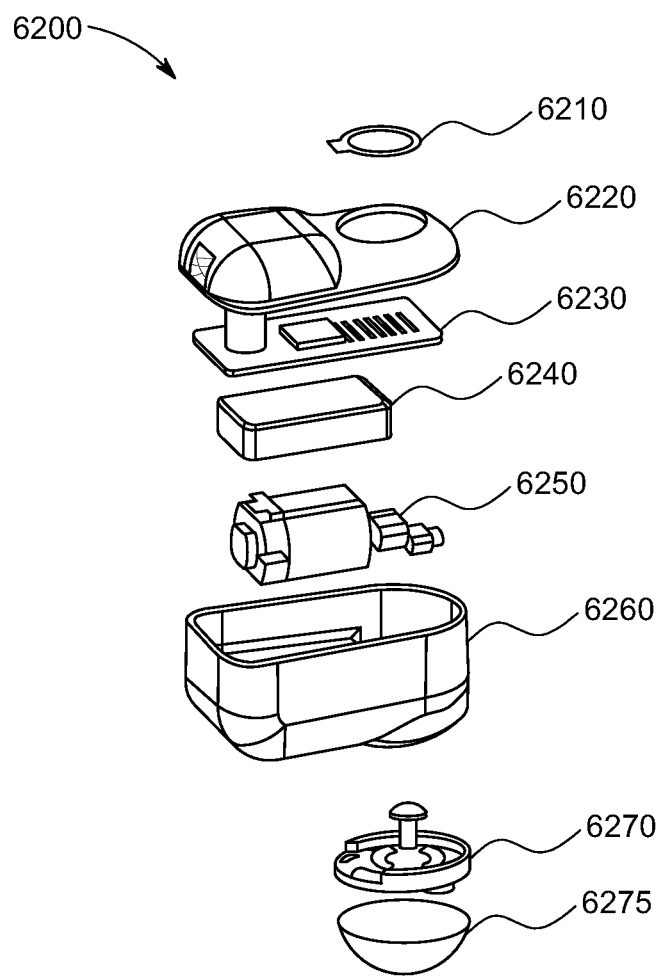
FIG. 40 is an exploded view of FIG. 39.

FIG. 40 depicts a component break out of the device in FIGS. 38 and 39. 6210 is a pressure sensitive switch which when depressed creates a larger vibration excursion or less excursion depending on what the user prefers. 6220 is a top cover for the device and 6250 is an eccentrically weighted motor. The motor is connected to the drive shaft 6270 to move the biocompatible patient interface 6275. The device is housed with aluminum 6260 or plastic with smooth edges. Rechargeable battery 6240 is regulated by voltage regulator 6230 to supply DC motor 6250. DC motor 6250 almost might be linked to a rotating cam to move a piston in a direction perpendicular to the motor to then be applied to the skin of a patient to activate a nerve through the skin.

Figure 41:
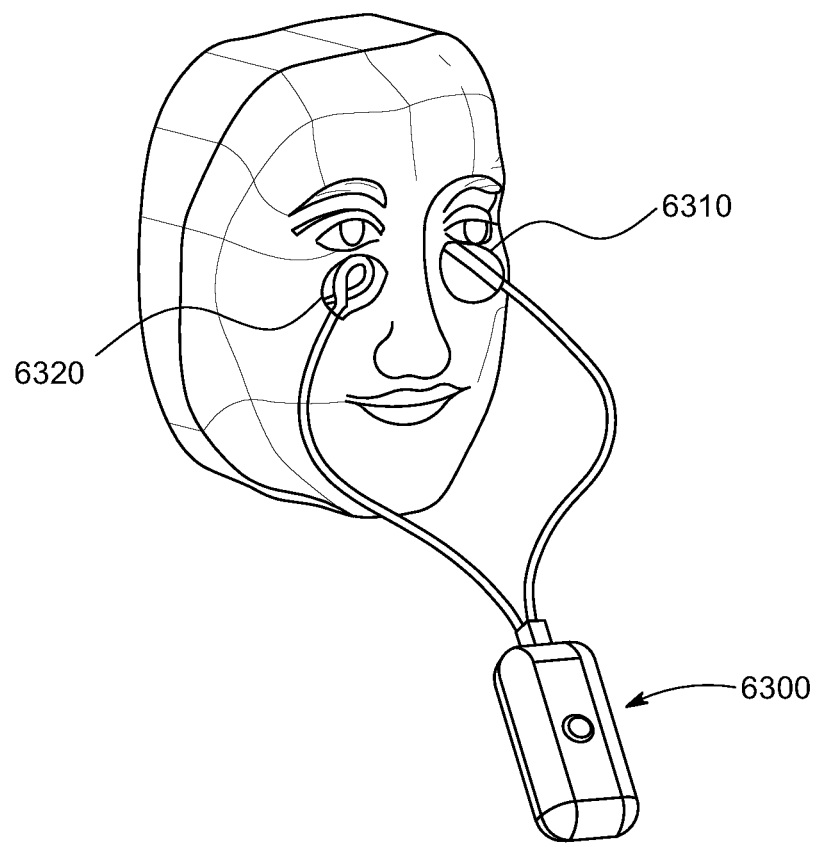
FIG. 41 is an embodiment in which vibration is applied to the lateral aspect of the nose.
Figure 42:
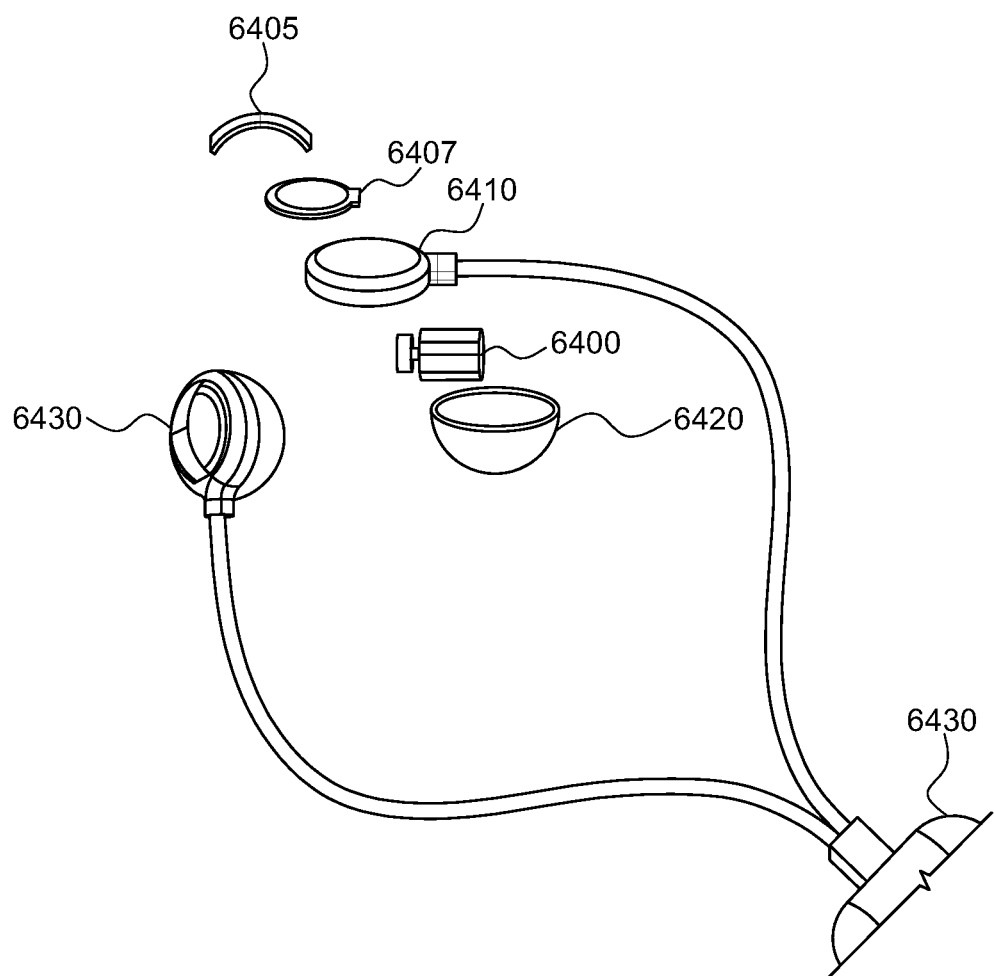
FIG. 42 is detailed schematic of the device in FIG. 41.

FIGS. 41-42 depict an embodiment wherein the vibrating elements are attached to the fingertips of the patient. Linear resonant actuators or eccentric motors are utilized in the fingertip devices. Fingerband 6405 allows the user's finger to be attached to the device. Biocompatible coupling 6420, 6430 facilitates the user application of the device to the skin of the user. Pressure sensor 6407 allows pressure controlled modulation of the frequency or amplitude of the end effectors which provide the energy to the skin of the user.

Figure 43:
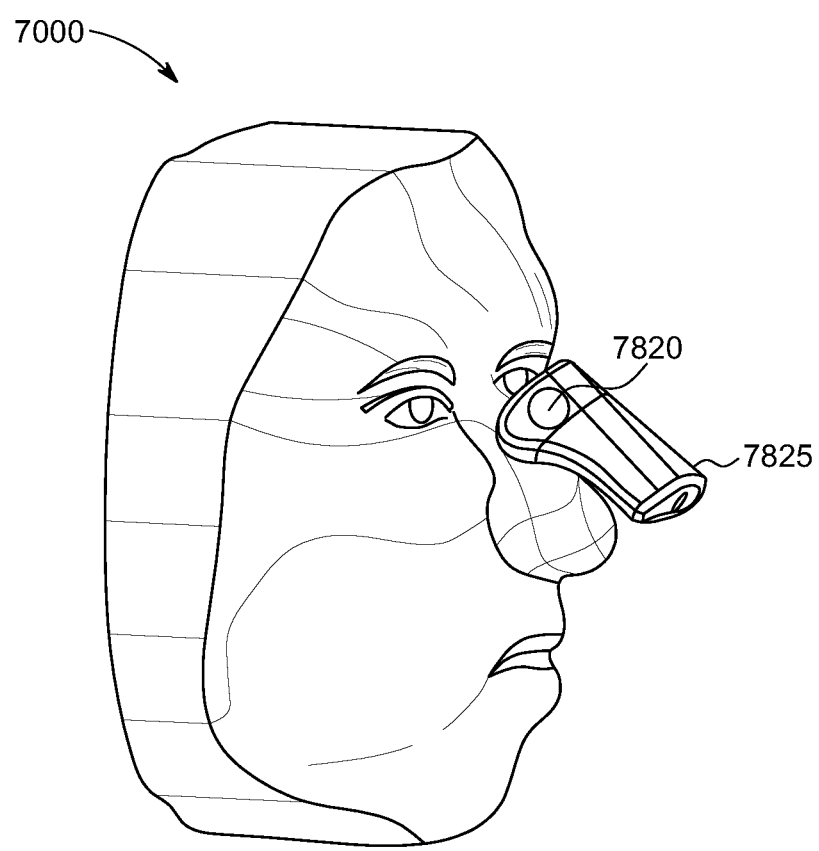
FIG. 43 depicts a device which applies mechanical vibration bilaterally to a patient.

FIG. 43 depicts a device 7000 which can be applied bilaterally to the nose of a patient to stimulate the external nasal nerve simultaneously or individually depending on patient preference. A feature of this device is that it has haptic feedback such that as the patient presses down on the device and on the nose, the device responds by applying a greater force or displacement to ensure nerve stimulation.

Figure 44:
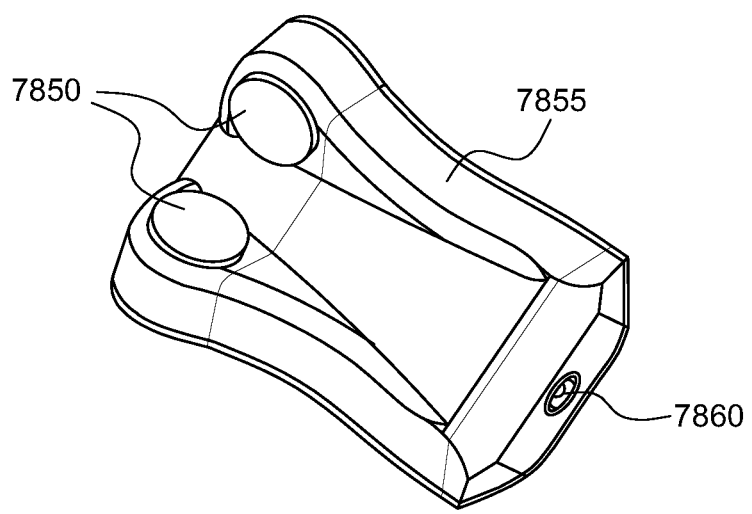
FIG. 44 depicts the device in FIG. 43 in more detail.

FIG. 44 depicts the underside of the device shown in FIG. 43. Pressure sensors 7850 sense the force being applied by the user. Material 7855 is preferably flexible so that the user can squeeze the device and compress the external nasal nerve and apply increasing vibrational force, the degree of which is dictated by the force the pressure sensor senses on the skin. The device Is rechargeable via port 7860 which can also potentially serve as a data port.

Figure 45:
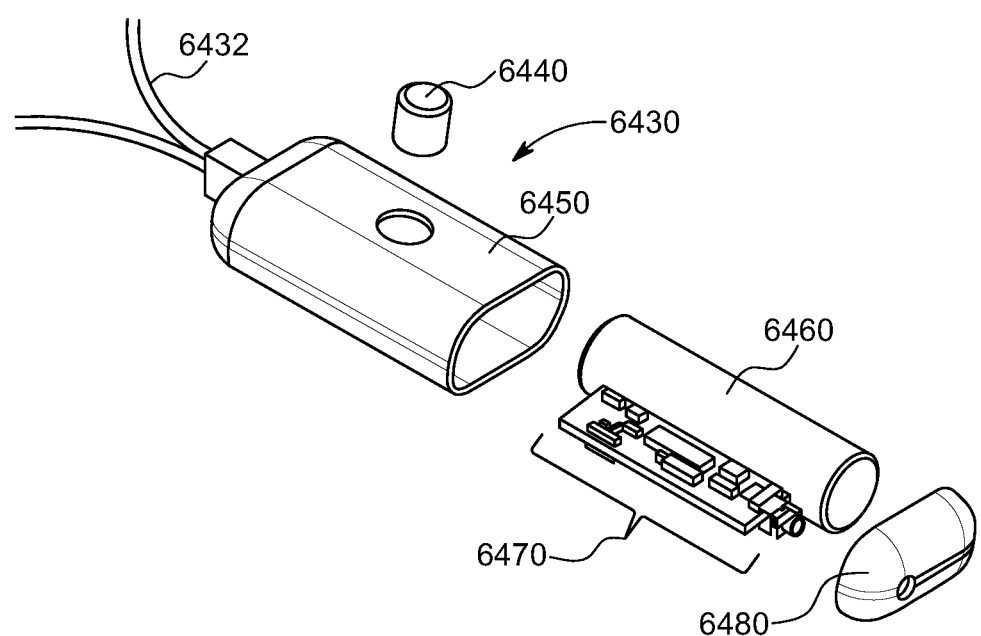
FIG. 45 depicts the inner mechanism of a device to create tears in a patient

FIG. 45 depicts a schematic of a portion of the device shown in FIG. 42. The drive electronics and programming are contained in this component of the device from FIG. 42 and is designed to fit in the palm of the hand of the user. Cables 6432 extend to the finger effectors and finger straps shown in FIG. 42. Lithium ion battery allows for recharging of the unit. Switch 6440 is a voice activated switch or simple toggle on-off which is activated by the user. Plastic body 6450 houses the circuitry and battery and is comprised of aluminum of plastic. Circuit board assembly 6470 contains control circuitry including voltage regulator and optionally feedback so that the motors can operate continuously.

Figure 46:
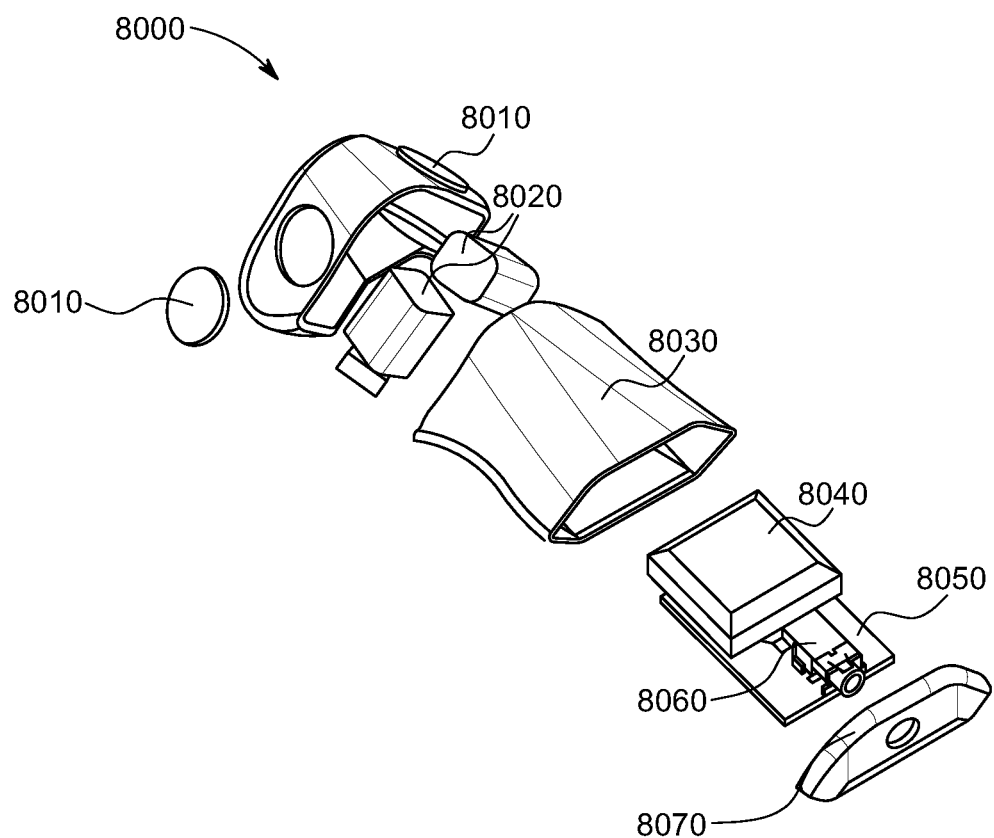
FIG. 46 depicts the inner mechanism of a device to create tears in a patient.

FIG. 46 depicts a schematic of the individual components of the device shown in FIG. 43. Pressure sensors 8010 enable coupling between the force applied by the user and the speed, torque, and force of the eccentric motors 8020 which create the vibratory effect to stimulate the external nasal nerve and parasympathetic pathway. Element 8030 is a housing for electronics and for the patient to grip while applying the vibration to the external nasal nerve and parasympathetic pathway. Battery 8040 is preferably rechargeable but also may be a replaceable battery. Cover 8070 seals the electronic circuit board 8050 and charge port 8060.

Figure 47:
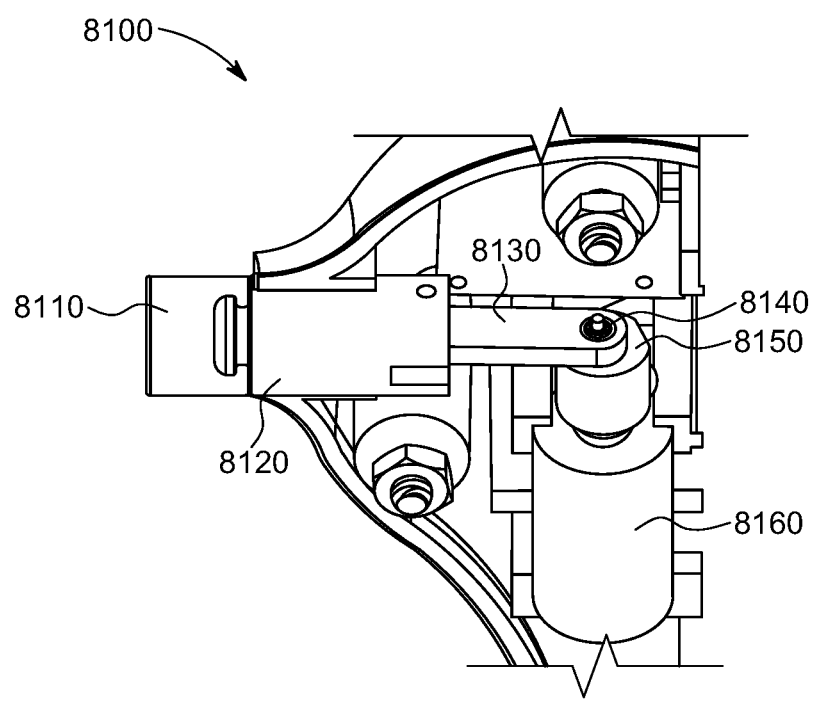
FIG. 47 depicts a device which generates linear vibratory motion to be applied to the skin of the face of a patient.

FIG. 47 depicts a preferred embodiment 8100 in which the end effector interface 8110 moves in a linear direction, actuated by a cam 8150 mechanically connected 8140 to an electric motor 8160. Rotation of the motor linked to the cam 8150 drives a piston 8120 with an end 8110 which also serves as the biocompatible interface with an edge adapted to activate a nerve such as the external nasal nerve. The piston 8120 and biocompatible interface 8110 move at an optimal frequency between 100 and 300 Hz or between 50 Hz and 400 Hz. The cam 8150 can be offset from the central axis 8140 to determine the excursion of the piston (e.g. 1 mm) and interface which then applies force to the skin of the patient and then to the nerve to be stimulated. In some embodiments, a governor is included to ensure that the frequency that is set by the user or pre-determined before delivery to the user is the actual frequency of the piston excursion. For example, in one embodiment, a photodiode or other detector is utilized to detect motion of the electric motor, linkages, or the piston; if the revolutions per minute (RPM) are not as pre-specified, additional current is added or subtracted from the motor. Electronic circuitry is also included which enables the device to record the time of treatment, time between treatments as well as a lock out time in between treatments (e.g. to ensure that the device is not overused or underused). Such data is stored in memory and is downloadable offline to a PC as a record of usage and compliance with the device in real world practice or in a clinical trial setting. The circuit further controls the voltage to ensure a constant power to the motor and constant rotation which can be pre-set or varied by the user.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following clauses define the scope of the invention and that methods and structures within the scope of these clauses and their equivalents be covered thereby.

What is claimed is:

1. A device configured to stimulate an external nasal nerve at the junction of an upper lateral nasal cartilage and a nasal bone of a patient to activate the patient's lacrimal glands at the junction of the upper lateral nasal cartilage and the nasal bone, said device comprising:
    an applicator having a handle and a skin interface, said skin interface having a thickness in a lateral direction between 0.5 mm and 5 mm and a skin contact surface comprising an edge which is curved in a medial direction and rounded in the lateral direction, said edge having a lateral radius in a range from 0.5 mm to 5 mm and a skin contact area in a range from 0.5 mm$^2$ to 10 mm$^2$, wherein the skin interface is configured to be depressed in the ridge at the junction of the nasal bone and nasal cartilage; and
    an actuator coupled to the skin interface and configured to vibrate the skin contact surface in an axial direction with a linear displacement in a range from 0.1 mm to 3 mm, wherein the handle is configured to allow the patient to manually press the skin interface in the axial direction to advance the lateral radius of the edge of the skin interface perpendicularly against the junction of the upper lateral nasal cartilage and nasal bone of the patient, at a frequency in a range from 100 Hz to 500 Hz, and with a force in a range from 0.5N to 5N to induce lacrimation.

2. The device of claim 1, wherein skin contact surface comprises a compliant member configured to be pressed against the junction of the upper lateral nasal cartilage and nasal bone of the patient to transmit a variable amount of user controlled vibratory energy to the patient's external nasal nerve.

3. The device of claim 2, wherein the compliant surface has a hardness in a range from Shore A40 to Shore A80.

4. The device of claim 2, wherein the device is further configured to apply the skin interface to the skin at difference angles and positions to maximize activation of the lacrimal glands.

5. The device of claim 1, wherein the actuator comprises a linear resonance actuator.

6. The device of claim 1, wherein the actuator comprises an eccentrically weighted motor.

7. The device of claim 1, wherein the actuator comprises a voice coil.

8. The device of claim 1, wherein the actuator comprises an electromagnet.

9. The device of claim 1, wherein the actuator comprises a piezoelectric crystal.

10. The device of claim 1, wherein the lateral curvature determines a sharpness of the rounded edge, wherein the sharpness is configured to activate an external nasal nerve when pressed against the junction.

11. The device of claim 1, wherein the actuator comprises a variable frequency and an application angle and position which are configured to be adjustable by the patient to optimize stimulation of the lacrimal gland.

12. The device of claim 1, wherein the actuator is configured to create a user defined variation in excursion.

13. The device of claim 1, further comprising an eccentrically weighted motor coupled to the actuator configured to allow the patient to vary a vibrational force to optimize stimulation of the lacrimal gland.

* * * * *